(12) United States Patent
Drummer et al.

(10) Patent No.: US 12,162,906 B2
(45) Date of Patent: Dec. 10, 2024

(54) METHOD FOR PREPARING MULTIMERIC FORMS OF THE HEPATITIS C VIRUS (HCV) ENVELOPE GLYCOPROTEIN 2 (HCV E2)

(71) Applicant: MACFARLANE BURNET INSTITUTE FOR MEDICAL RESEARCH AND PUBLIC HEALTH LIMITED, Melbourne (AU)

(72) Inventors: Heidi Drummer, Melbourne (AU); Pantelis Poumbourios, Melbourne (AU); Robert Center, Melbourne (AU)

(73) Assignee: Macfarlane Burnet Institute for Medical Research and Public Health Limited, Melbourne (AU)

( * ) Notice: Subject to any disclaimer, the term of this patent is extended or adjusted under 35 U.S.C. 154(b) by 263 days.

(21) Appl. No.: 16/337,900

(22) PCT Filed: Sep. 22, 2017

(86) PCT No.: PCT/AU2017/051037
§ 371 (c)(1),
(2) Date: Mar. 28, 2019

(87) PCT Pub. No.: WO2018/058177
PCT Pub. Date: Apr. 5, 2018

(65) Prior Publication Data
US 2019/0284230 A1    Sep. 19, 2019

(30) Foreign Application Priority Data

Sep. 29, 2016  (AU) ................................ 2016903961

(51) Int. Cl.
| | |
|---|---|
| *C07K 1/113* | (2006.01) |
| *A61K 39/12* | (2006.01) |
| *A61K 39/29* | (2006.01) |
| *A61P 31/14* | (2006.01) |
| *C07K 1/13* | (2006.01) |
| *C07K 1/22* | (2006.01) |
| *C07K 14/005* | (2006.01) |
| *C07K 14/18* | (2006.01) |
| *G01N 33/50* | (2006.01) |
| *G01N 33/569* | (2006.01) |

(Continued)

(52) U.S. Cl.
CPC ............ *C07K 1/1133* (2013.01); *A61K 39/12* (2013.01); *A61K 39/29* (2013.01); *A61P 31/14* (2018.01); *C07K 1/1136* (2013.01); *C07K 1/13* (2013.01); *C07K 1/22* (2013.01); *C07K 14/005* (2013.01); *C07K 14/1833* (2013.01); *G01N 33/5047* (2013.01); *G01N 33/5052* (2013.01); *G01N 33/56966* (2013.01); *G01N 33/5767* (2013.01); *A61K 2039/645* (2013.01); *C07K 16/109* (2013.01); *C07K 2317/33* (2013.01); *C07K 2317/76* (2013.01); *C12N 2770/24222* (2013.01); *C12N 2770/24234* (2013.01)

(58) Field of Classification Search
CPC ................ C07K 1/1133; C07K 1/1136; C07K 14/1833
See application file for complete search history.

(56) References Cited

U.S. PATENT DOCUMENTS

| | | | | |
|---|---|---|---|---|
| 6,150,134 | A  * | 11/2000 | Maertens ............... | A61K 39/12 435/69.3 |
| 9,598,467 | B2 * | 3/2017 | McCaffrey ............. | A61K 39/29 |
| 2013/0224246 | A1 * | 8/2013 | Drummer ............... | A61K 39/12 435/69.3 |

FOREIGN PATENT DOCUMENTS

| | | |
|---|---|---|
| WO | WO 1996/004385 A2 | 2/1996 |
| WO | WO 03/051912 A2 * | 6/2003 |

(Continued)

OTHER PUBLICATIONS

International Search Report and Written Opinion mailed Dec. 22, 2017 for International Patent Application No. PCT/AU2017/051037.
Alhammad Y. et al., "Monoclonal Antibodies Directed toward the Hepatitis C Virus Glycoprotein E2 Detect Antigenic Differences Modulated by the N-Terminal Hypervariable Region 1 (HVR1), HVR2, and Intergenotypic Variable Region", Journal of Virology, Dec. 2015, vol. 89, No. 24, pp. 12245-12261.

(Continued)

*Primary Examiner* — Jeffrey S Parkin
(74) *Attorney, Agent, or Firm* — Knobbe, Martens, Olson & Bear, LLP

(57) ABSTRACT

A method of preparing extracellularly assembled higher order antigen from a native lower order antigen the method comprising the following steps: (i) contacting lower order antigen with a solution comprising a reducing agent for a time and under 5 conditions sufficient to reduce one or more native cysteines; and (ii) removing or diluting the reducing agent or contacting the reduced lower order antigen with an oxidising agent, to elicit assembly of lower order antigen from (i) into an assembled higher order antigen; wherein at least 10% of the lower order antigen is converted to higher order antigen in step (ii) and whereby the assembled higher order antigen 10 displays at least reduced binding to non-neutralizing antibodies compared to the lower order antigen and retains binding to at least one neutralizing antibody. A method of producing a vaccine composition comprising following the steps of the method and then mixing the assembled higher order antigen with a pharmaceutically or physiologically acceptable diluent, carrier or adjuvant. A composition comprising a 15 higher order extracellularly assembled antigen, wherein the assembled antigen displays at least reduced binding to a non-neutralizing antibody compared to a native control higher order antigen. Use of the assembled higher order antigen to stimulate an immune response or for the detection and/or isolation of an immune cell such as a B-cell specific for the antigen.

8 Claims, 43 Drawing Sheets
Specification includes a Sequence Listing.

(51) Int. Cl.
G01N 33/576 (2006.01)
A61K 39/00 (2006.01)
C07K 16/10 (2006.01)

(56) References Cited

FOREIGN PATENT DOCUMENTS

| WO | WO 2003/051912 A2 | 6/2003 |
|---|---|---|
| WO | WO 2003/052122 A2 | 6/2003 |
| WO | WO 2008/022401 A1 | 2/2008 |
| WO | WO 2012/016290 A1 | 2/2012 |
| WO | WO 2012/068637 A1 | 5/2012 |

OTHER PUBLICATIONS

Drummer H.E., "Challenges to the development of vaccines to hepatitis C virus that elicit neutralizing antibodies", Frontiers in Microbiology, 2014, vol. 5, Article 329.
McCaffrey K. et al., "Expression and Characterization of a Minimal Hepatitis C Virus Glycoprotein E2 Core Domain That Retains CD81 Binding", Journal of Virology, Sep. 2007, vol. 81, No. 17, pp. 9584-9590.
McCaffrey K. et al., "Role of Conserved Cysteine Residues in Hepatitis C Virus Glycoprotein E2 Folding and Function", Journal of Virology, 2012, vol. 86, No. 7, pp. 3961-3974.
Moody M.A. et al., "Antigen-Specific B Cell Detection Reagents: Use and Quality Control", Cytometry A, Nov. 2008, vol. 73, No. 11, pp. 1086-1092.
Rodríguez-Rodríguez M. et al., "Structural properties of the ectodomain of hepatitis C virus E2 envelope protein", Virus Research, 2009, vol. 139, No. 1, pp. 91-99.
Extended European Search Report dated May 6, 2020 for European Patent Application No. 17854239.5.
Martinez-Donato et al., "Multimeric HCV E2 Protein Obtained From *Pichia pastoris* Cells Induces a Strong Immune Response in Mice", *Molecular Biotechnology*, vol. 35, Mar. 1, 2007, pp. 225-235.
Krey et al., "Structural Basis of HCV Neutralization by Human Monoclonal Antibodies Resistant to Viral Neutralization Escape", *PLOS Pathogens*, vol. 9, No. 5, May 16, 2013.
Altman et al., "Phenotypic Analysis of Antigen-Specific T Lymphocytes", (1996) *Science* 274(5284):94-96.
Broering et al, "Identification and Characterization of Broadly Neutralizing Human Monoclonal Antibodies Directed against the E2 Envelope Glycoprotein of Hepatitis C Virus", (2009) *J Virol.* 2009;83(23):12473-82.
Connor et al, "Vpr Is Required for Efficient Replication of Human Immunodeficiency Virus Type-1 in Mononuclear Phagocytes", (1995) *Virology.* 206(2):935-44.
De Taeye et al, "Immunogenicity of Stabilized HIV-1 Envelope Trimers with Reduced Exposure of Non-neutralizing Epitopes" (2015) *Cell*;163(7):1702-15.

Dolton et al, "More tricks with tetramers: a practical guide to staining T cells with peptide-MHC multimers" (2015) *Immunology* 146(1):11-22.
Flint et al, "Characterization of hepatitis C virus E2 glycoprotein interaction with a putative cellular receptor, CD81" (1999) *J Virol.* 73(8):6235-44.
He et al, "Use of a novel human immunodeficiency virus type I reporter virus expressing human placental alkaline phosphatase to detect an alternative viral receptor" (1995) *J Virol.* 69(7):4587-92.
Keck et al, "Human Monoclonal Antibodies to a Novel Cluster of Conformational Epitopes on HCV E2 with Resistance to Neutralization Escape in a Genotype 2a Isolate", (2012) *PLoS Pathog.* 8(4):e1002653.
Khan et al, "Molecular drivers and cortical spread of lateral entorhinal cortex dysfunction in preclinical Alzheimer's disease" (2014) *Nature.* 2014.
Keck et al, "Cooperativity in virus neutralization by human monoclonal antibodies to two adjacent regions located at the amino terminus of hepatitis C virus E2 glycoprotein", (2013) *J Virol.* 2013;87(1):37-51.
Law et al, "Broadly neutralizing antibodies protect against hepatitis C virus quasispecies challenge", (2008) *Nat Med.* 2008;14(1):25-7.
Morin et al, "Human monoclonal antibody HCV1 effectively prevents and treats HCV infection in chimpanzees", (2012) *PLoS Pathog.* 8(8):e1002895.
Owsianka et al, "Functional analysis of hepatitis C virus E2 glycoproteins and virus-like particles reveals structural dissimilarities between different forms of E2", (2001) *J Gen Virol.*82(Pt 8):1877-83.
Owsianka et al, "Monoclonal antibody AP33 defines a broadly neutralizing epitope on the hepatitis C virus E2 envelope glycoprotein" (2005) *J Virol.* 79(17):11095-104.
Pantua et al, "Glycan Shifting on Hepatitis C Virus (HCV) E2 Glycoprotein Is a Mechanism for Escape from Broadly Neutralizing Antibodies", (2013) *J Mol Biol.* 2013;425(11):1899-914.
Petrovsky et al, "Vaccine adjuvants: current state and future trends", (2004) *Immunol Cell Biol.* Oct;82(5):488-96.
Sabo et al, "Neutralizing monoclonal antibodies against hepatitis C virus E2 protein bind discontinuous epitopes and inhibit infection at a postattachment step", (2011) *J Virol.* 2011;85(14):7005-19.
Tarr et al, "Characterization of the hepatitis C virus E2 epitope defined by the broadly neutralizing monoclonal antibody AP33", (2006) *Hepatology.* 43(3):592-601.
Vietheer et al, "The core domain of hepatitis C virus glycoprotein E2 generates potent cross-neutralizing antibodies in guinea pigs", (2017) *Hepatology.* 2017;65(4):1117-31.
Vollers et al, "Class II major histocompatibility complex tetramer staining: progress, problems, and prospects", (2008) *Immunology.* 123(3):305-313.
Wilson-Welder et al, "Vaccine adjuvants: current challenges and future approaches", (2009) *J Pharm Sci.* Apr;98(4):1278-316.
Zhang et al, "Depletion of interfering antibodies in chronic hepatitis C patients and vaccinated chimpanzees reveals broad cross-genotype neutralizing activity", (2009) *Proc Natl Acad Sci U S A.* 106(18):7537-41.

\* cited by examiner

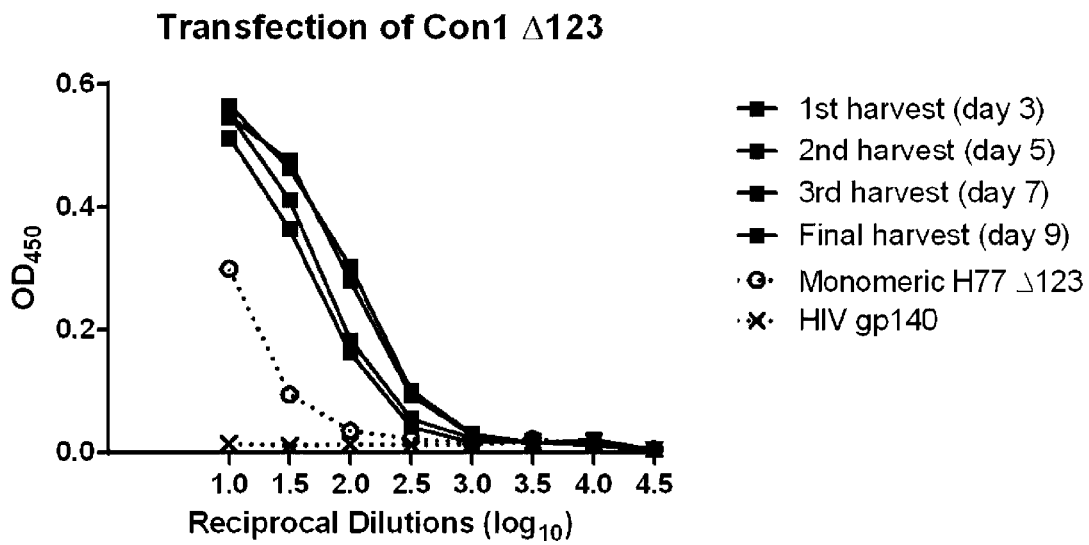
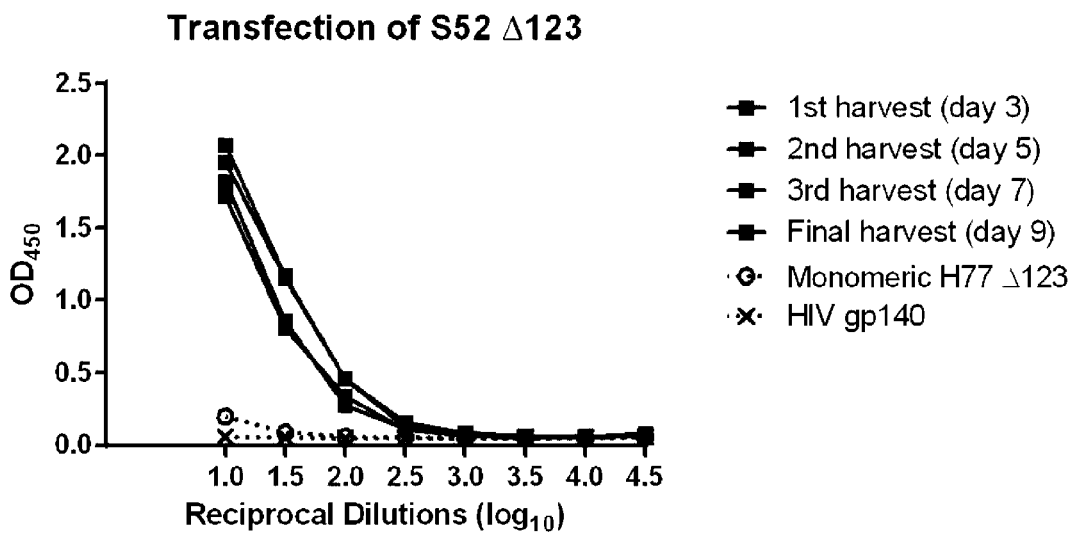
FIG. 2

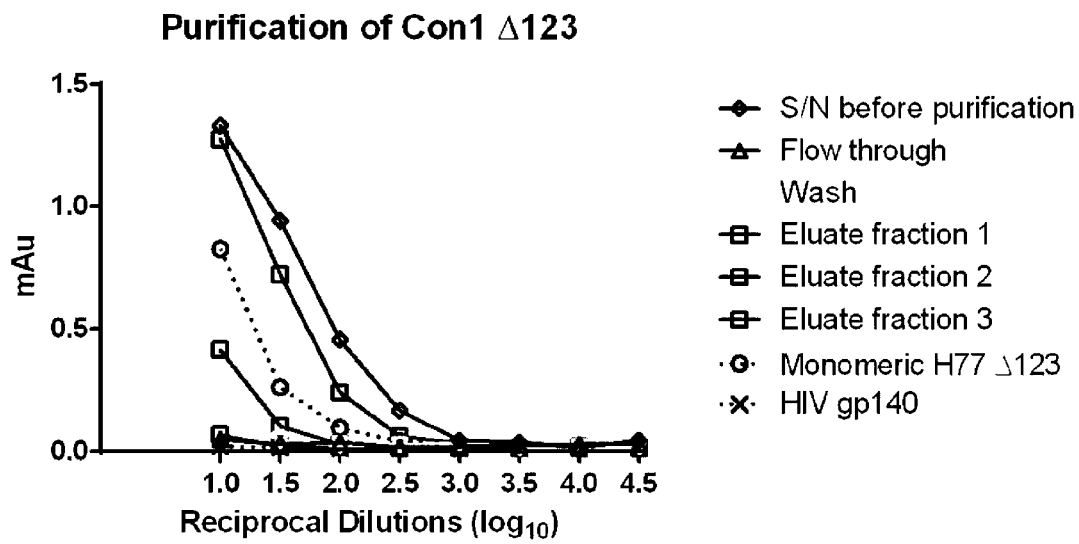
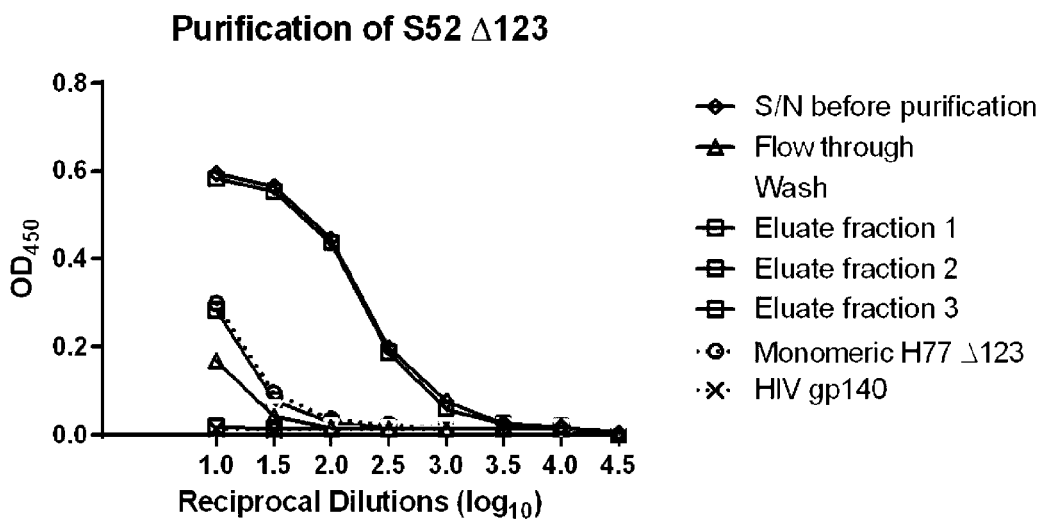
FIG. 2 (CONTINUED)

A
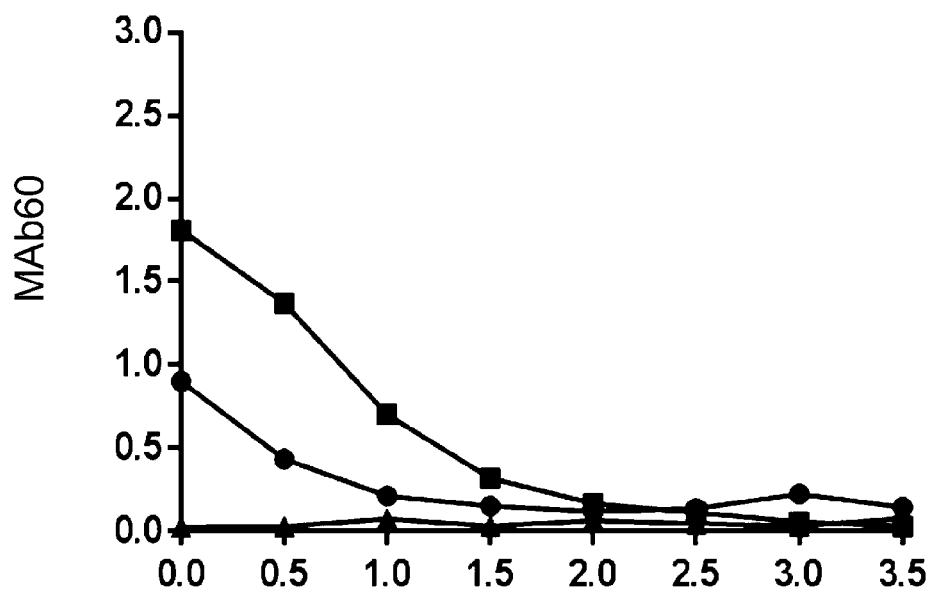
H77c
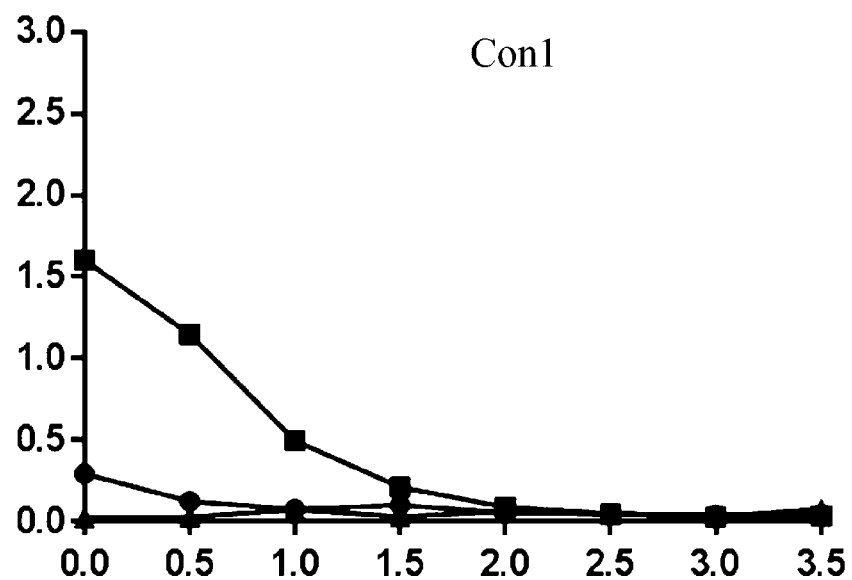
Con1
FIG. 5

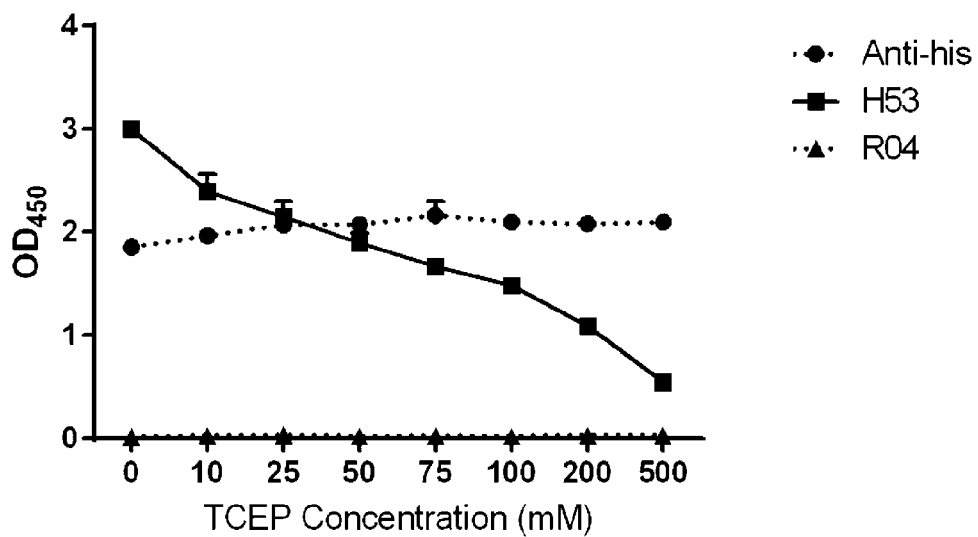
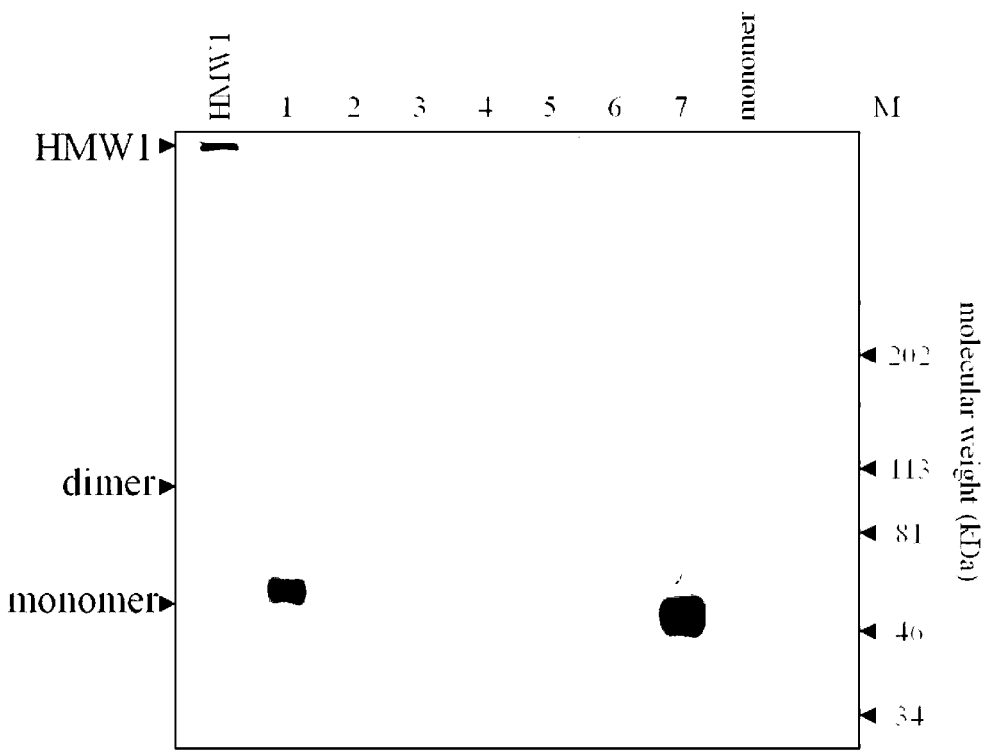
FIG. 6

B
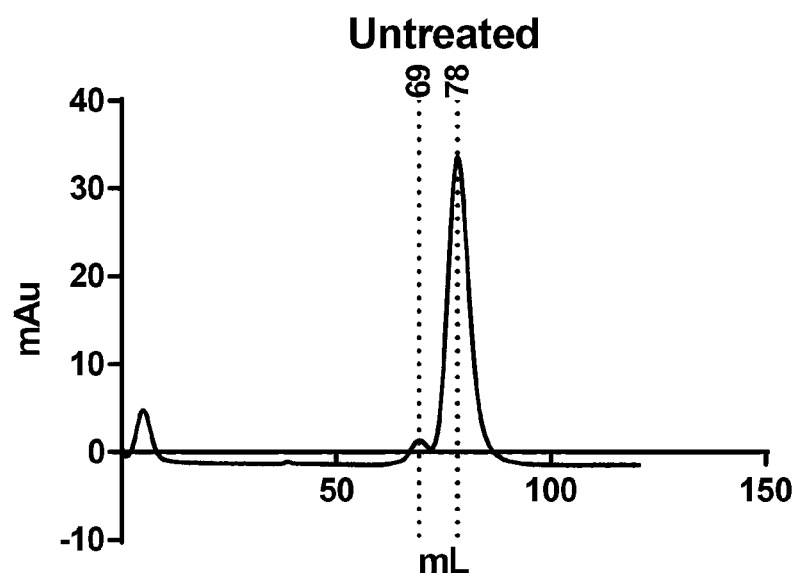
C
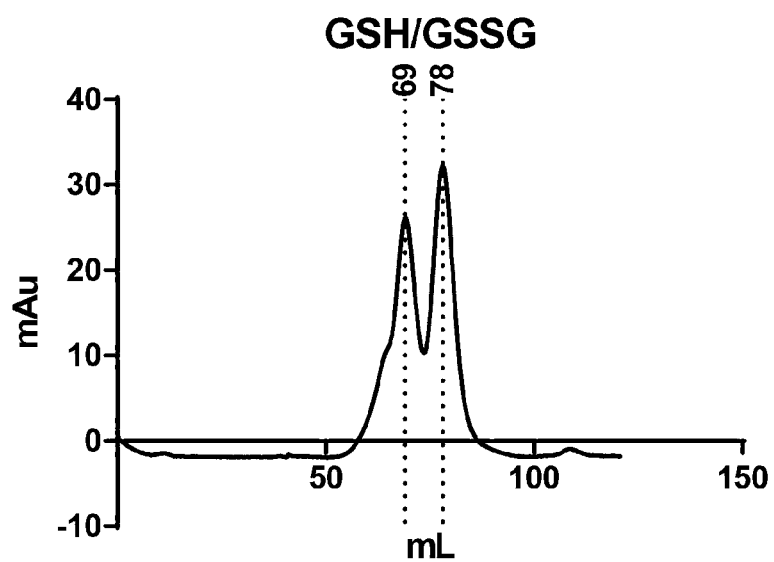
FIG. 7 (CONTINUED)

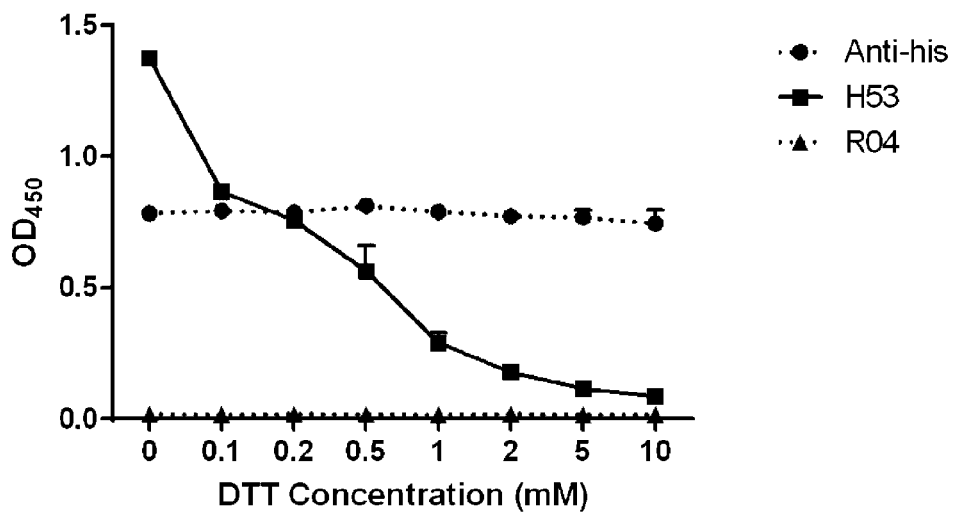
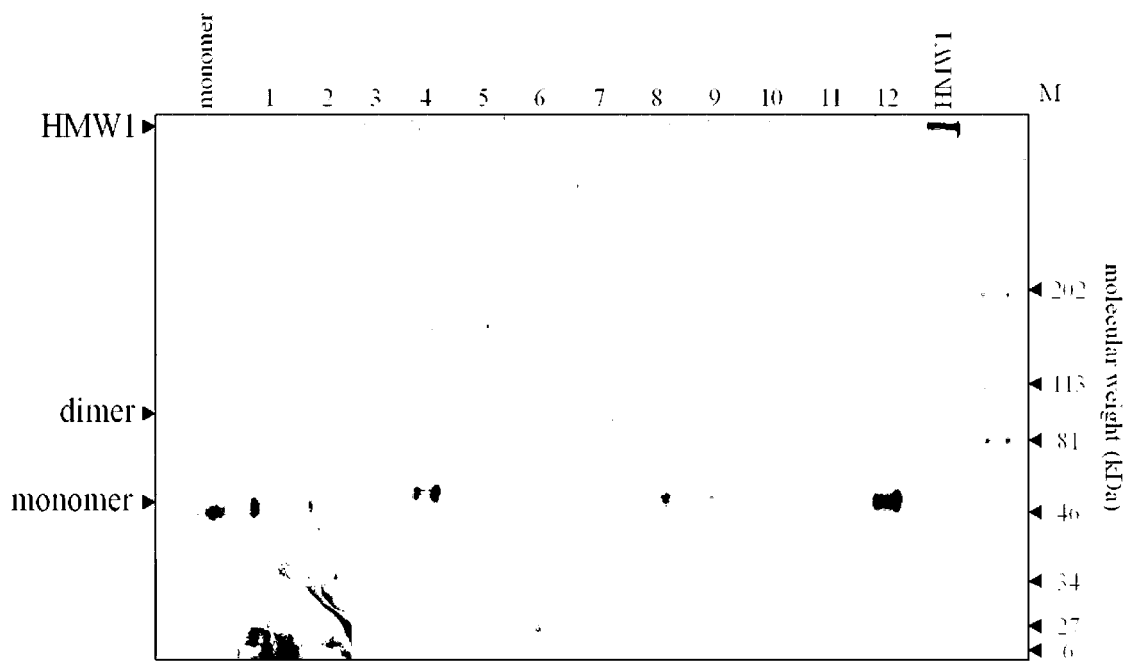
FIG. 8

C
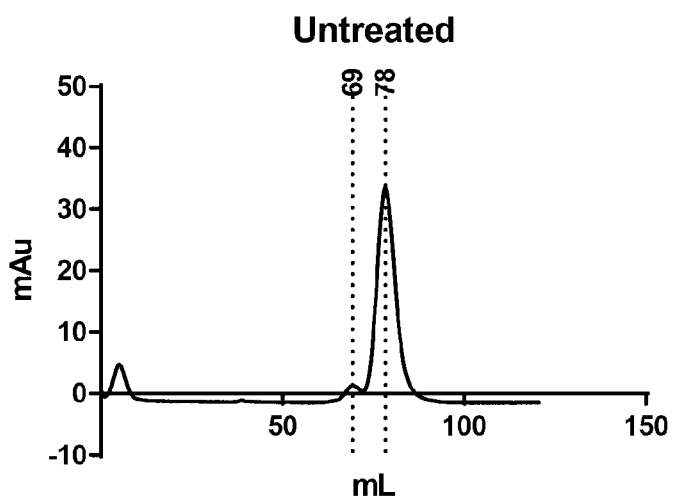
D
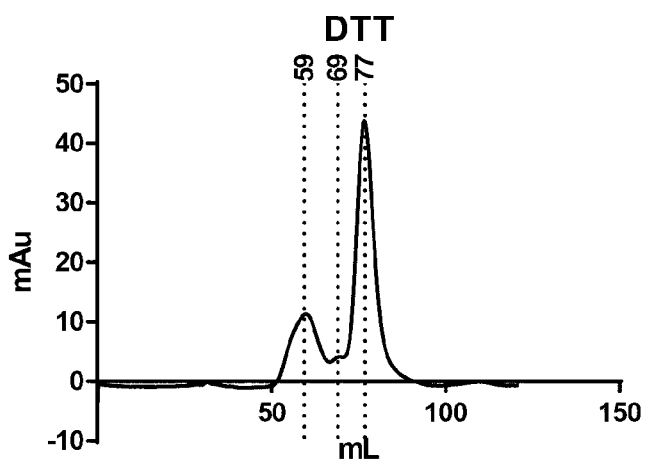
FIG. 8 (CONTINUED)

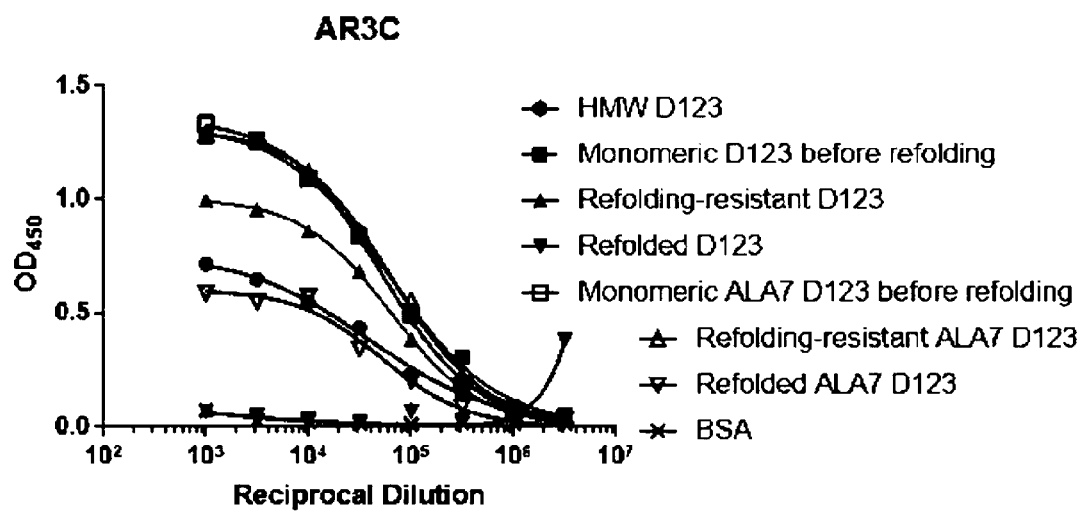
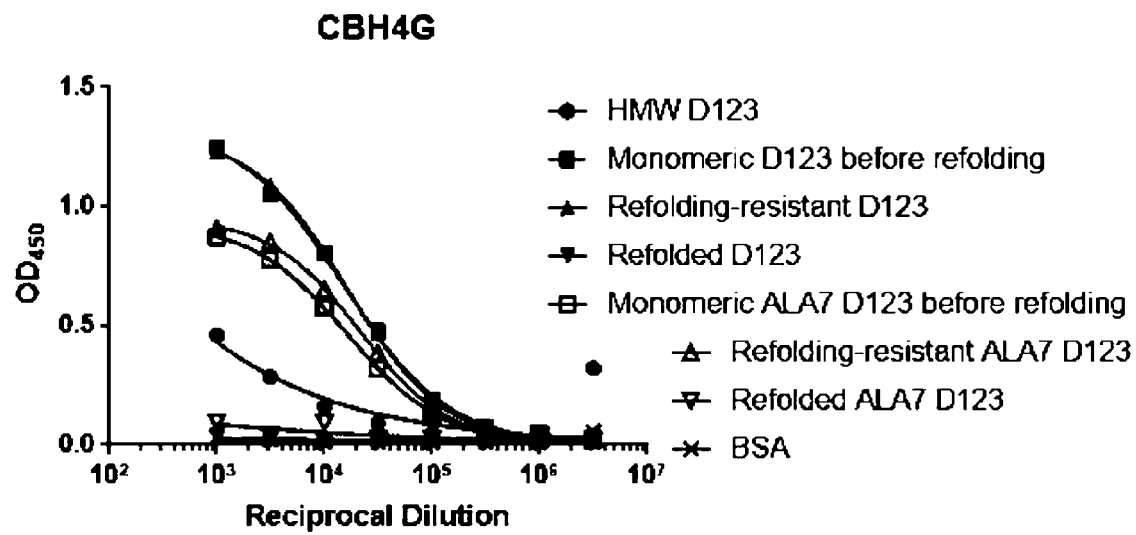
FIG. 9

C
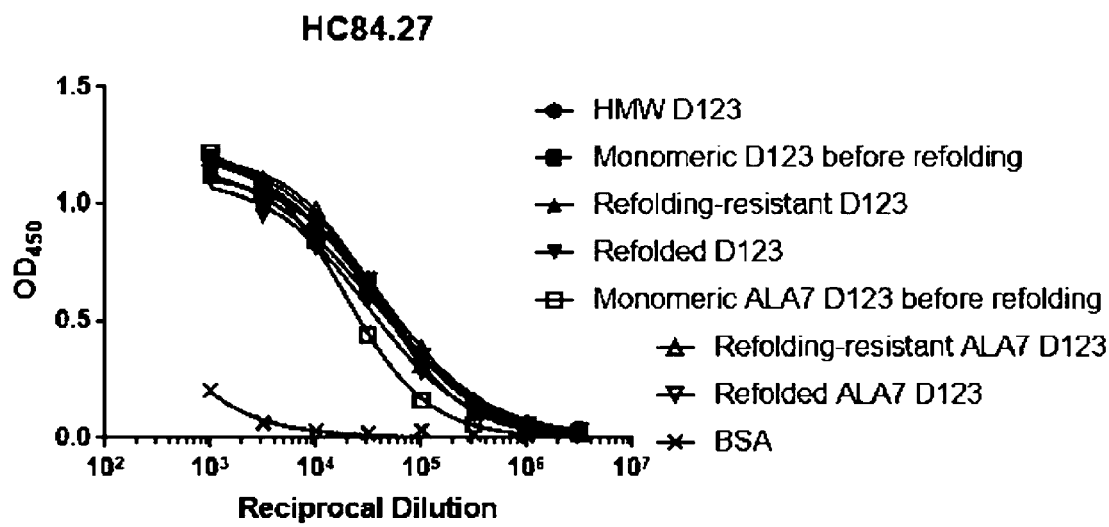
D
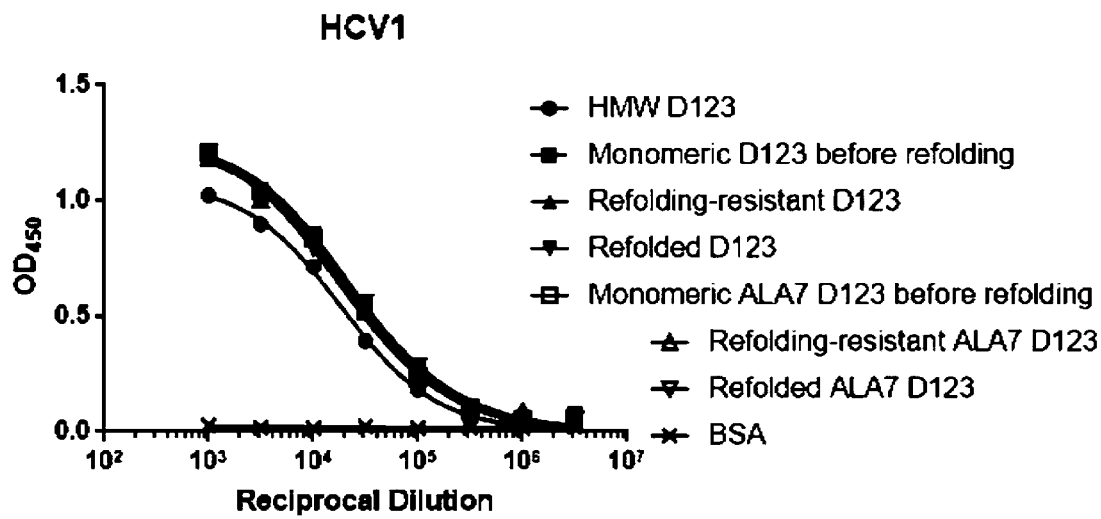
FIG. 9 (CONTINUED)

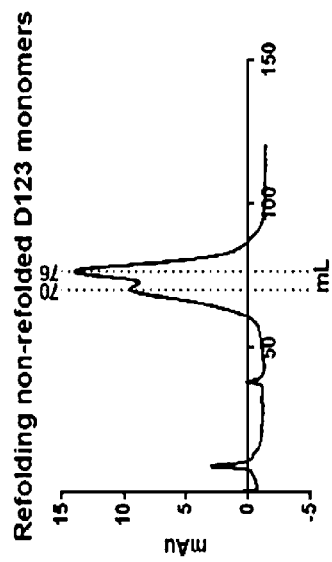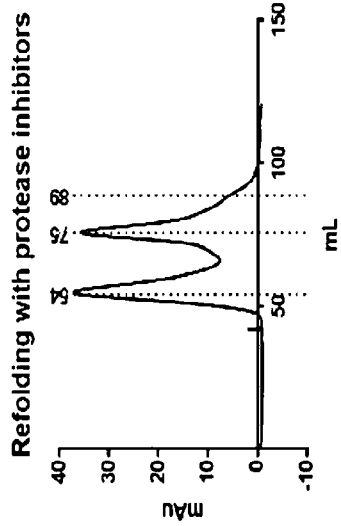
FIG. 11

```
                                                       HVR1
ED43      YFSMQANWAKVILVLFLFAGVDAETHVSGAAVGRSTAGLANLFSSGSKQNLQLINSNGSW
H77c      YFSMVGNWAKVLVVLLLFAGVDAETHVTGGNAGRTTAGLVGLLTPGAKQNIQLINTNGSW
SA13      YYASAANWAKVVLVLFLFAGVDANTRTVGGSAAQGARGLASLFTPGPQQNLQLINTNGSW
S52       YYSMQGNWAKVAIVMIMFSGVDAETYVTGGSVAHSARGLTSLFSMGAKQKLQLVNTNGSW
EUHK2     YFGMAGNWLKVLAVLFLFAGVEAQTMIAHG-VSQTTSGFASLLTPGAKQNIQLINTNGSW
QC69      YFGMAGNWAKVILIMLLMSGVDAETMAVGARAAHTTGALVSLLNPGPSQRLQLINTNGSW
J6        YFSMQGAWAKVVVILLLAAGVDARTHTVGGSAAQTTGRLTSLFDMGPRQKIQLVNTNGSW
          *:.   . *  ** :::::**:*.*         . ...:   :...*: *..*:**:;****
                                                              HVR2
ED43      HINRTALNCNDSLNTGFLASLFYTHKFNSSGCSERLACCKSLDSYGQGWGPLGVA-NISG
H77c      HINSTALNCNESLNTGWLAGLFYQHKFNSSGCPERLASCRRLTDFAQGWGPISYA-NGSG
SA13      HINRTALNCNDSLQTGFVAGLLYYHKFNSTGCPQRMASCRPLAAFDQGWGTISYA-AVSG
S52       HINSTALNCNESINTGFIAGLFYYHKFNSTGCPQRLSSCKPIISFRQGWGPLTDA-NITG
EUHK2     HINRTALNCNDSLQTGFLASLFYTHKFNSSGCPERMAACKPLARFRQGWGQITHK-WVSG
QC69      HINRTALNCNDSLQTGFIAALFYTHRFNSSGCPERMASCKPLSDPDQGWGPLWYN-STER
J6        HINRTALNCNDSLHTGFIASLFYTHSFNSSGCPERMSACRSIEAFRVGRGALQYEDNVTN
          *** ******:*::**::*.*:*  * ***:**.:*::.*:  :  :  *** :

ED43      SSDDRPYCWHYAPRPCGIVPASSVCGPVYCFTPSPVVVGTTDHVGVPTYTWGENETDVFL
H77c      L-DERPYCWHYPPRPCGIVPAKSVCGPVYCFTPSPVVVGTTDRSGAPTYSWGANDTDVFV
SA13      PSDDKPYCWHYPPRPCGIVPARGVCGPVYCFTPSPVVVGTTDRKGNPTYSWGENETDIFL
S52       PSDDRPYCWHYAPRPCSVVPASSVCGPVYCFTPSPVVVGTTDIKGRPTYNWGENETDVFL
EUHK2     PSDDRPYCWHYAPRPCEVVPARSVCGPVYCFTPSPVVVGTTDKRGNPTYTWGENETDVFM
QC69      PSDQRPYCWHYAPSPCGIVPAKDVCGPVYCFTPSPVVVGTTDRRGVPTYTWGENESDVFL
J6        PEDMRPYCWHYPPRQCGVVSAKTVCGPVYCFTPSPVVVGTTDRLGAPTYTWGENETDVFL
            * :******.*   *  :*.*  ******************   * ***.** *::*:*:
                                        igVR/VR3
ED43      LNSTRPPHGAWFGCVWMNSTGFTKTCGAPPCEV-----N-TNNGTWHCPTDCFRKHPETT
H77c      LNNTRPPLGNWFGCTWMNSTGFTKVCGAPPCVI-----GGVGNNTLLCPTDCFRKHPEAT
SA13      LNNTRPPTGNWFGCTWMNSTGFVKTCGAPPCNL-----GPTGNNSLKCPTDCFRKHPDAT
S52       LESLRPPSGRWFGCAWMNSTGFLKTCGAPPCNIYGGEGDPENETDLFCPTDCFRKHPEAT
EUHK2     LESLRPPTGGWFGCTWMNSTGFTKTCGAPPCQIVPGNYN-SSANELLCPTDCFRKHPEAT
QC69      LNSTRPPQGSWFGCSWMNTTGFTKTCGGPPCKIRP--QGAQSNTSLTCPTDCFRKHPRAT
J6        LNSTRPPLGSWFGCTWMNSSGYTKTCGAPPCRTRA---DFNASTDLLCPTDCFRKHPDTT
          *:. *** * **** ***::*: *.**.***                  ********** :*

ED43      YAKCGSGPWITPRCLIDYPYRLWHFPCTANFSVFNIRTFVGGIEHRMQAACNWTRGEVCG
H77c      YSRCGSGPWITPRCMVDYPYRLWHYPCTINYTIFKVRMYVGGVEHRLEAACNWTRGERCD
SA13      YTKCGSGPWLTPRCLVHYPYRLWHYPCTLNYTIFKVRMYIGGLEHRLEVACNWTRGERCD
S52       YSRCGAGPWLTPRCMVDYPYRLWHYPCTVNFTLFKVRMFVGGFEHRFTAACNWTRGERCN
EUHK2     YQRCGSGPWVTPRCLVDYAYRLWHYPCTVNFTLHKVRMFVGGTEHRFDVACNWTRGERCE
QC69      YSACGSGPWLTPRCMVHYPYRLWHYPCTVNFTIHKVRLYIGGVEHRLDAACNWTRGERCD
J6        YLKCGSGPWLTPRCLIDYPYRLWHYPCTVNYTIFKIRMYVGGVEHRLTAACNFTRGDRCN
          *  **:***:*****::.*.*****:*** *:::.::* ::** ***: .***:***: *

ED43      LEHRDRVELSPLLLTTTAWQILPCSFTTLPALSTGLIHLHQNIVDVQYLYGVGSAVVSWA
H77c      LEDRDRSELSPLLLSTTQWQVLPCSFTTLPALSTGLIHLHQNIVDVQYLYGVGSSIASWA
SA13      LEDRDRAELSPLLHTTTQWAILPCSFTPTPALSTGLIHLHQNIVDTQYLYGLSSSIVSWA
S52       IEDRDRSEQHPLLHSTTELAILPCSFTPMPALSTGLIHLHQNIVDVQYLYGVGSDMVGWA
EUHK2     LHDRNRIEMSPLLFSTTQLSILPCSFSTMPALSTGLIHLHQNIVDVQYLYGVSTNVTSWV
QC69      LEDRDRVDMSPLLHSTTELAILPCSFVPLPALSTGLIHLHQNIVDAQYLYGLSPAIISWA
J6        LEDRDRSQLSPLLHSTTEWAILPCSYSDLPALSTGLLHLHQNIVDVQFMYGLSPALTKYI
          :..*:*  :  ***  :**   :****: *******:********.*::**:..   :  :
```

FIG. 12

Δ123Ala7 codon optimised nucleotide sequence
GGTACCGCTAGCGCCACCATGAACCCCCTGCTGATCCTGACCTTTGTGGCCGCTGCCCTGGCCGAGACAC
ACCAGAACATCCAGCTGATCAACACCAACGGCAGCTGGCACATCAACAGCACCGCCCTGAACTGCAACG
AGAGCCTGAACACAGGCTGGCTGGCCGGCCTGTTCTACCAGCACAAGTTCAACAGCAGCGGAGCCCCCG
AGAGACTGGCCTCTTGTGGATCTTCTGGCGCCTGGCACTACCCCCCTAGACCTTGTGGAATCGTGCCCGC
CAAGAGCGTGTGCGGCCCTGTGTACTGCTTCACCCCTAGCCCTGTGGTCGTGGGCACCACCGATAGATCT
GGCGCCCCTACCTATTCCTGGGGCGCCAACGACACCGACGTGTTCGTGCTGAACAACACCCGGCCACCCC
TGGGCAATTGGTTCGGCTGCACCTGGATGAACTCCACCGGCTTCACCAAAGTGTGCGGCGCTCCTCCTGC
CGGATCCAGCGGAGCACCTACCGACGCCTTCAGAAAGCACCCCGAGGCCACCTACTCTAGAGCCGGATC
TGGCCCCTGGATCACCCCCAGATGCATGGTGGACTACCCCTACCGGCTGTGGCACTATCCCTGCACCATC
AACTACACCATCTTCAAAGTGCGGATGTACGTGGGCGGCGTGGAACACAGACTGGAAGCCGCCTGCAAC
TGGACCAGAGGCGAGAGAGCCGACCTGGAAGATCGGGACAGAAGCGAGCACCACCACCATCACCACTG
ATGACTCGAG

Δ123Ala7 protein sequence

ETHQNIQLIN TNGSWHINST ALNCNESLNT GWLAGLFYQH KFNSSGAPER LASCGSSGAW
HYPPRPCGIV PAKSVCGPVY CFTPSPVVVG TTDRSGAPTY SWGANDTDVF VLNNTRPPLG
NWFGCTWMNS TGFTKVCGAP PAGSSGAPTD AFRKHPEATY SRAGSGPWIT PRCMVDYPYR
LWHYPCTINY TIFKVRMYVG GVEHRLEAAC NWTRGERADL EDRDRSE

FIG. 13

```
AF009606               MSTNPKPQRKTKRNTNRRPQDVKFPGGGQIVGGVYLLPRRGPRLGVRATRKTSERSQPRG   60
AF009606_FulllengthE2  ------------------------------------------------------------   0
AF009606_E2661         ------------------------------------------------------------   0
WT_E2661               ------------------------------------------------------------   0
Delta123               ------------------------------------------------------------   0

AF009606               RRQPIPKARRPEGRTWAQPGYPWPLYGNEGCGWAGWLLSPRGSRPSWGPTDPRRRSRNLG   120
AF009606_FulllengthE2  ------------------------------------------------------------   0
AF009606_E2661         ------------------------------------------------------------   0
WT_E2661               ------------------------------------------------------------   0
Delta123               ------------------------------------------------------------   0

AF009606               KVIDTLTCGFADLMGYIPLVGAPLGGAARALAHGVRVLEDGVNYATGNLPGCSFSIFLLA   180
AF009606_FulllengthE2  ------------------------------------------------------------   0
AF009606_E2661         ------------------------------------------------------------   0
WT_E2661               ------------------------------------------------------------   0
Delta123               ------------------------------------------------------------   0

AF009606               LLSCLTVPASAYQVRNSSGLYHVTNDCPNSSIVYEAADAILHTPGCVPCVREGNASRCWV   240
AF009606_FulllengthE2  ------------------------------------------------------------   0
AF009606_E2661         ------------------------------------------------------------   0
WT_E2661               ------------------------------------------------------------   0
Delta123               ------------------------------------------------------------   0

AF009606               AVTPTVATRDGKLPTTQLRRHIDLLVGSATLCSALYVGDLCGSVFLVGQLFTFSPRRHWT   300
AF009606_FulllengthE2  ------------------------------------------------------------   0
AF009606_E2661         ------------------------------------------------------------   0
WT_E2661               ------------------------------------------------------------   0
Delta123               ------------------------------------------------------------   0
```

FIG. 14

| | | |
|---|---|---|
| AF009606_FulllengthE2 | TQDCNCSIYPGHITGHRMAWDMMMNWSPTAALVVAQLLRIPQAIMDMIAGAHWGVLAGIA | 360 |
| AF009606_E2661 | ------------------------------------------------------------ | 0 |
| AF009606_E2661 | ------------------------------------------------------------ | 0 |
| WT_E2661 | ------------------------------------------------------------ | 0 |
| Delta123 | ------------------------------------------------------------ | 0 |
| | | |
| AF009606_FulllengthE2 | YFSMVGNWAKVLVVLLFAGVDAETHVTGGSAGRTTAGLVGLLTPGAKQNIQLINTNGSW | 420 |
| AF009606_E2661 | ------------------ETHVTGGSAGRTTAGLVGLLTPGAKQNIQLINTNGSW | 37 |
| AF009606_E2661 | ------------------ETHVTGGSAGRTTAGLVGLLTPGAKQNIQLINTNGSW | 37 |
| WT_E2661 | ------------------ETHVTGGNAGRTTAGLVGLLTPGAKQNIQLINTNGSW | 37 |
| Delta123 | ------------------ETH---------------------QNIQLINTNGSW | 15 |
| | ***    *********** | |
| | | |
| AF009606_FulllengthE2 | HINSTALNCNESLNTGWLAGLFYQHKFNSSGCPERLASCRRLTDFAQGWGPISYANGSGL | 480 |
| AF009606_E2661 | HINSTALNCNESLNTGWLAGLFYQHKFNSSGCPERLASCRRLTDFAQGWGPISYANGSGL | 97 |
| AF009606_E2661 | HINSTALNCNESLNTGWLAGLFYQHKFNSSGCPERLASCRRLTDFAQGWGPISYANGSGL | 97 |
| WT_E2661 | HINSTALNCNESLNTGWLAGLFYQHKFNSSGCPERLASCRRLTDFAQGWGPISYANGSGL | 97 |
| Delta123 | HINSTALNCNESLNTGWLAGLFYQHKFNSSGCPERLASCGS------------------- | 56 |
| | ***************************************    | |
| | | |
| AF009606_FulllengthE2 | DERPYCWHYPPRPCGIVPAKSVCGPVYCFTPSPVVVGTTDRSGAPTYSWGANDTDVFVLN | 540 |
| AF009606_E2661 | DERPYCWHYPPRPCGIVPAKSVCGPVYCFTPSPVVVGTTDRSGAPTYSWGANDTDVFVLN | 157 |
| AF009606_E2661 | DERPYCWHYPPRPCGIVPAKSVCGPVYCFTPSPVVVGTTDRSGAPTYSWGANDTDVFVLN | 157 |
| WT_E2661 | DERPYCWHYPPRPCGIVPAKSVCGPVYCFTPSPVVVGTTDRSGAPTYSWGANDTDVFVLN | 157 |
| Delta123 | ---SGCWHYPPRPCGIVPAKSVCGPVYCFTPSPVVVGTTDRSGAPTYSWGANDTDVFVLN | 113 |
| | *********************************************** | |
| | | |
| AF009606_FulllengthE2 | NTRPPLGNWFGCTWMNSTGFTKVCGAPPCVIGGVGNNTLLCPTDCFRKHPEATYSRCGSG | 600 |
| AF009606_E2661 | NTRPPLGNWFGCTWMNSTGFTKVCGAPPCVIGGVGNNTLLCPTDCFRKHPEATYSRCGSG | 217 |
| AF009606_E2661 | NTRPPLGNWFGCTWMNSTGFTKVCGAPPCVIGGVGNNTLLCPTDCFRKHPEATYSRCGSG | 217 |
| WT_E2661 | NTRPPLGNWFGCTWMNSTGFTKVCGAPPCVIGGVGNNTLLCPTDCFRKHPEATYSRCGSG | 217 |
| Delta123 | NTRPPLGNWFGCTWMNSTGFTKVCGAPPCGSS--------GCPTDCFRKHPEATYSRCGSG | 166 |
| | *****************************        ********************* | |

FIG. 14 (CONTINUED)

```
AF009606              PWITPRCMVDYPYRLWHYPCTINYTIFKVRMYVGGVEHRLEAACNWTRGERCDLEDRDRS  660
AF009606_FulllengthE2 PWITPRCMVDYPYRLWHYPCTINYTIFKVRMYVGGVEHRLEAACNWTRGERCDLEDRDRS  277
AF009606_E2661        PWITPRCMVDYPYRLWHYPCTINYTIFKVRMYVGGVEHRLEAACNWTRGERCDLEDRDRS  277
WT_E2661              PWITPRCMVDYPYRLWHYPCTINYTIFKVRMYVGGVEHRLEAACNWTRGERCDLEDRDRS  277
Delta123              PWITPRCMVDYPYRLWHYPCTINYTIFKVRMYVGGVEHRLEAACNWTRGERCDLEDRDRS  226
                      ************************************************************

AF009606              ELSPLLLSTTQWQVLPCSFTTLPALSTGLIHLHQNIVDVQYLYGVGSSIASWAIKWEYVV  720
AF009606_FulllengthE2 ELSPLLLSTTQWQVLPCSFTTLPALSTGLIHLHQNIVDVQYLYGVGSSIASWAIKWEYVV  337
AF009606_E2661        E-----------------------------------------------------------  278
WT_E2661              E-----------------------------------------------------------  278
Delta123              *                                                             227

AF009606              LLFLLLADARVCSCLWMMLLISQAEAALENLVILNAASLAGTHGLVSFLVFFCFAWYLKG  780
AF009606_FulllengthE2 LLFLLLADARVCSCLWMMLLISQAEA----------------------------------  363
AF009606_E2661        ------------------------------------------------------------  278
WT_E2661              ------------------------------------------------------------  278
Delta123                                                                            227

AF009606              RWVPGAVYAFYGMWPLLLLLLALPQRAYALDTEVAASCGGVVLVGLMALTLSPYYKRYIS  840
AF009606_FulllengthE2 ------------------------------------------------------------  363
AF009606_E2661        ------------------------------------------------------------  278
WT_E2661              ------------------------------------------------------------  278
Delta123                                                                            227
```

FIG. 14 (CONTINUED)

```
AF009606               WCMWWLQYFLTRVEAQLHVWVPPLNVRGGRDAVILLMCVVHPTLVFDITKLLLAIFGPLW   900
AF009606_FulllengthE2  ------------------------------------------------------------   363
AF009606_E2661         ------------------------------------------------------------   278
WT_E2661               ------------------------------------------------------------   278
Delta123               ------------------------------------------------------------   227

AF009606               ILQASLLKVPYFVRVQGLLRICALARKIAGGHYVQMAIIKLGALTGTYVYNHLTPLRDWA   960
AF009606_FulllengthE2  ------------------------------------------------------------   363
AF009606_E2661         ------------------------------------------------------------   278
WT_E2661               ------------------------------------------------------------   278
Delta123               ------------------------------------------------------------   227

AF009606               HNGLRDLAVAVEPVVFSRMETKLITWGADTAACGDIINGLPVSARRGQEILLGPADGMVS   1020
AF009606_FulllengthE2  ------------------------------------------------------------   363
AF009606_E2661         ------------------------------------------------------------   278
WT_E2661               ------------------------------------------------------------   278
Delta123               ------------------------------------------------------------   227

AF009606               KGWRLLAPITAYAQQTRGLLGCIITSLTGRDKNQVEGEVQIVSTATQTFLATCINGVCWT   1080
AF009606_FulllengthE2  ------------------------------------------------------------   363
AF009606_E2661         ------------------------------------------------------------   278
WT_E2661               ------------------------------------------------------------   278
Delta123               ------------------------------------------------------------   227

AF009606               VYHGAGTRTIASPKGPVIQMYTNVDQDLVGWPAPQGSRSLTPCTCGSSDLYLVTRHADVI   1140
AF009606_FulllengthE2  ------------------------------------------------------------   363
AF009606_E2661         ------------------------------------------------------------   278
WT_E2661               ------------------------------------------------------------   278
Delta123               ------------------------------------------------------------   227
```

FIG. 14A

| | | |
|---|---|---|
| AF009606 | PVRRRGDSRGSLLSPRPISYLKGSSGGPLLCPAGHAVGLFRAAVCTRGVAKAVDFIPVEN | 1200 |
| AF009606_FulllengthE2 | ------------------------------------------------------------ | 363 |
| AF009606_E2661 | ------------------------------------------------------------ | 278 |
| WT_E2661 | ------------------------------------------------------------ | 278 |
| Delta123 | ------------------------------------------------------------ | 227 |
| | | |
| AF009606 | LETTMRSPVFTDNSSPPAVPQSFQVAHLHAPTGSGKSTKVPAAYAAQGYKVLVLNPSVAA | 1260 |
| AF009606_FulllengthE2 | ------------------------------------------------------------ | 363 |
| AF009606_E2661 | ------------------------------------------------------------ | 278 |
| WT_E2661 | ------------------------------------------------------------ | 278 |
| Delta123 | ------------------------------------------------------------ | 227 |
| | | |
| AF009606 | TLGFGAYMSKAHGVDPNIRTGVRTITTGSPITYSTYGKFLADGGCSGGAYDIIICDECHS | 1320 |
| AF009606_FulllengthE2 | ------------------------------------------------------------ | 363 |
| AF009606_E2661 | ------------------------------------------------------------ | 278 |
| WT_E2661 | ------------------------------------------------------------ | 278 |
| Delta123 | ------------------------------------------------------------ | 227 |
| | | |
| AF009606 | TDATSILGIGTVLDQAETAGARLVVLATATPPGSVTVSHPNIEEVALSTTGEIPFYGKAI | 1380 |
| AF009606_FulllengthE2 | ------------------------------------------------------------ | 363 |
| AF009606_E2661 | ------------------------------------------------------------ | 278 |
| WT_E2661 | ------------------------------------------------------------ | 278 |
| Delta123 | ------------------------------------------------------------ | 227 |
| | | |
| AF009606 | PLEVIKGGRHLIFCHSKKKCDELAAKLVALGINAVAYYRGLDVSVIPTSGDVVVVSTDAL | 1440 |
| AF009606_FulllengthE2 | ------------------------------------------------------------ | 363 |
| AF009606_E2661 | ------------------------------------------------------------ | 278 |
| WT_E2661 | ------------------------------------------------------------ | 278 |
| Delta123 | ------------------------------------------------------------ | 227 |

FIG. 14A (CONTINUED)

| | | |
|---|---|---|
| AF009606_FulllengthE2 | MTGFTGDFDSVIDCNTCVTQTVDFSLDPTFTIETTLPQDAVSRTQRRGRTGRGKPGIYR | 1500 |
| AF009606_E2661 | ------------------------------------------------------------ | 363 |
| AF009606_ | ------------------------------------------------------------ | 278 |
| WT_E2661 | ------------------------------------------------------------ | 278 |
| Delta123 | ------------------------------------------------------------ | 227 |

| | | |
|---|---|---|
| AF009606_FulllengthE2 | FVAPGERPSGMFDSSVLCECYDAGCAWYELTPAETTVRLRAYMNTPGLPVCQDHLEFWEG | 1560 |
| AF009606_E2661 | ------------------------------------------------------------ | 363 |
| AF009606_ | ------------------------------------------------------------ | 278 |
| WT_E2661 | ------------------------------------------------------------ | 278 |
| Delta123 | ------------------------------------------------------------ | 227 |

| | | |
|---|---|---|
| AF009606_FulllengthE2 | VFTGLTHIDAHFLSQTKQSGENFPYLVAYQATVCARAQAPPSWDQMWKCLIRLKPTLHG | 1620 |
| AF009606_E2661 | ------------------------------------------------------------ | 363 |
| AF009606_ | ------------------------------------------------------------ | 278 |
| WT_E2661 | ------------------------------------------------------------ | 278 |
| Delta123 | ------------------------------------------------------------ | 227 |

| | | |
|---|---|---|
| AF009606_FulllengthE2 | PTPLLYRLGAVQNEVTLTHPITKYIMTCMSADLEVVTSTWVLVGGVLAALAAYCLSTGCV | 1680 |
| AF009606_E2661 | ------------------------------------------------------------ | 363 |
| AF009606_ | ------------------------------------------------------------ | 278 |
| WT_E2661 | ------------------------------------------------------------ | 278 |
| Delta123 | ------------------------------------------------------------ | 227 |

FIG. 14A (CONTINUED)

| | | |
|---|---|---|
| AF009606 | VIVGRIVLSGKPAIIPDREVLYQEFDEMEECSQHLPYIEQGMMLAEQFKQKALGLLQTAS | 1740 |
| AF009606_FulllengthE2 | ------------------------------------------------------------ | 363 |
| AF009606_E2661 | ------------------------------------------------------------ | 278 |
| WT_E2661 | ------------------------------------------------------------ | 278 |
| Delta123 | ------------------------------------------------------------ | 227 |

| | | |
|---|---|---|
| AF009606 | RQAEVITPAVQTNWQKLEVFWAKHMWNFISGIQYLAGLSTLPGNPAIASLMAFTAAVTSP | 1800 |
| AF009606_FulllengthE2 | ------------------------------------------------------------ | 363 |
| AF009606_E2661 | ------------------------------------------------------------ | 278 |
| WT_E2661 | ------------------------------------------------------------ | 278 |
| Delta123 | ------------------------------------------------------------ | 227 |

| | | |
|---|---|---|
| AF009606 | LTTGQTLLFNILGGWVAAQLAAPGAATAFVGAGLAGAAIGSVGLGKVLVDILAGYGAGVA | 1860 |
| AF009606_FulllengthE2 | ------------------------------------------------------------ | 363 |
| AF009606_E2661 | ------------------------------------------------------------ | 278 |
| WT_E2661 | ------------------------------------------------------------ | 278 |
| Delta123 | ------------------------------------------------------------ | 227 |

| | | |
|---|---|---|
| AF009606 | GALVAFKIMSGEVPSTEDLVNLLPAILSPGALVVGVVCAAILRRHVGPGEGAVQWMNRLI | 1920 |
| AF009606_FulllengthE2 | ------------------------------------------------------------ | 363 |
| AF009606_E2661 | ------------------------------------------------------------ | 278 |
| WT_E2661 | ------------------------------------------------------------ | 278 |
| Delta123 | ------------------------------------------------------------ | 227 |

| | | |
|---|---|---|
| AF009606 | AFASRGNHVSPTHYVPESDAAARVTAILSSLTVTQLLRRLHQWISSECTTPCSGSWLRDI | 1980 |
| AF009606_FulllengthE2 | ------------------------------------------------------------ | 363 |
| AF009606_E2661 | ------------------------------------------------------------ | 278 |
| WT_E2661 | ------------------------------------------------------------ | 278 |
| Delta123 | ------------------------------------------------------------ | 227 |

FIG. 14B

```
AF009606              WDWICEVLSDFKTWLKAKLMPQLPGIPFVSCQRGYRGVWRGDGIMHTRCHCGAEITGHVK   2040
AF009606_FulllengthE2 ------------------------------------------------------------    363
AF009606_E2661        ------------------------------------------------------------    278
WT_E2661              ------------------------------------------------------------    278
Delta123              ------------------------------------------------------------    227

AF009606              NGTMRIVGPRTCRNMWSGTFPINAYTTGPCTPLPAPNYKFALWRVSAEEVEIRRVGDFH     2100
AF009606_FulllengthE2 ------------------------------------------------------------    363
AF009606_E2661        ------------------------------------------------------------    278
WT_E2661              ------------------------------------------------------------    278
Delta123              ------------------------------------------------------------    227

AF009606              YVSGMTTDNLKCPCQIPSPEFFTELDGVRLHRFAPPCKPLLREEVSFRVGLHEYPVGSQL     2160
AF009606_FulllengthE2 ------------------------------------------------------------    363
AF009606_E2661        ------------------------------------------------------------    278
WT_E2661              ------------------------------------------------------------    278
Delta123              ------------------------------------------------------------    227

AF009606              PCEPEPDVAVLTSMLTDPSHITAEAAGRRLARGSPPSMASSSASQLSAPSLKATCTANHD    2220
AF009606_FulllengthE2 ------------------------------------------------------------    363
AF009606_E2661        ------------------------------------------------------------    278
WT_E2661              ------------------------------------------------------------    278
Delta123              ------------------------------------------------------------    227

AF009606              SPDAELIEANLLWRQEMGGNITRVESENKVVILDSFDPLVAEEDEREVSVPAEILRKSRR    2280
AF009606_FulllengthE2 ------------------------------------------------------------    363
AF009606_E2661        ------------------------------------------------------------    278
WT_E2661              ------------------------------------------------------------    278
Delta123              ------------------------------------------------------------    227
```

FIG. 14B (CONTINUED)

```
AF009606                  FARALPVWARPDYNPPLVETWKKPDYEPPVVHGCPLPPPRSPPVPPPRKKRTVVLTESTL  2340
AF009606_FulllengthE2     ------------------------------------------------------------   363
AF009606_E2661            ------------------------------------------------------------   278
WT_E2661                  ------------------------------------------------------------   278
Delta123                  ------------------------------------------------------------   227

AF009606                  STALAELATKSFGSSSTSGITGDNTTSSEPAPSGCPPDSDVESYSSMPPLEGEPGDPDL  2400
AF009606_FulllengthE2     ------------------------------------------------------------   363
AF009606_E2661            ------------------------------------------------------------   278
WT_E2661                  ------------------------------------------------------------   278
Delta123                  ------------------------------------------------------------   227

AF009606                  SDGSWSTVSSGADTEDVVCCSMSYSWTGALVTPCAAEEQKLPINALSNSLLRHHNLVYST  2460
AF009606_FulllengthE2     ------------------------------------------------------------   363
AF009606_E2661            ------------------------------------------------------------   278
WT_E2661                  ------------------------------------------------------------   278
Delta123                  ------------------------------------------------------------   227

AF009606                  TSRSACQRQRKKVTFDRLQVLDSHYQDVLKEVKAAASKVKANLLSVEEACSLTPPHSAKSK  2520
AF009606_FulllengthE2     ------------------------------------------------------------   363
AF009606_E2661            ------------------------------------------------------------   278
WT_E2661                  ------------------------------------------------------------   278
Delta123                  ------------------------------------------------------------   227
```

FIG. 14B (CONTINUED)

```
AF009606_FulllengthE2    FGYGAKDVRCHARKAVAHINSVWKDLLEDSVTPIDTTIMAKNEVFCVQPEKGGRKPARLI   2580
AF009606_FulllengthE2    ------------------------------------------------------------   363
AF009606_E2661           ------------------------------------------------------------   278
WT_E2661                 ------------------------------------------------------------   278
Delta123                 ------------------------------------------------------------   227

AF009606_FulllengthE2    VFPDLGVRVCEKMALYDVVSKLPLAVMGSSYGFQYSPGQRVEFLVQAWKSKKTPMGFSYD   2640
AF009606_FulllengthE2    ------------------------------------------------------------   363
AF009606_E2661           ------------------------------------------------------------   278
WT_E2661                 ------------------------------------------------------------   278
Delta123                 ------------------------------------------------------------   227

AF009606_FulllengthE2    TRCFDSTVTESDIRTEEAIYQCCDLDPQARVAIKSLTERLYVGGPLTNSRGENCGYRRCR   2700
AF009606_FulllengthE2    ------------------------------------------------------------   363
AF009606_E2661           ------------------------------------------------------------   278
WT_E2661                 ------------------------------------------------------------   278
Delta123                 ------------------------------------------------------------   227

AF009606_FulllengthE2    ASGVLTTSCGNTLTCYIKARAACRAAGLQDCTMIVGDDLVVICESAGVQEDAASLRAFT   2760
AF009606_FulllengthE2    ------------------------------------------------------------   363
AF009606_E2661           ------------------------------------------------------------   278
WT_E2661                 ------------------------------------------------------------   278
Delta123                 ------------------------------------------------------------   227

AF009606_FulllengthE2    EAMTRYSAPPGDPPQPEYDLELITSCSSNVSVAHDGAGKRVYYLTRDPTTPLARAAWETA   2820
AF009606_FulllengthE2    ------------------------------------------------------------   363
AF009606_E2661           ------------------------------------------------------------   278
WT_E2661                 ------------------------------------------------------------   278
Delta123                 ------------------------------------------------------------   227
```

FIG. 14C

```
AF009606             RHTPVNSWLGNIIMFAPTLWARMIMTHFFSVLIARDQLEQALNCEIYGACYSIEPLDLP   2880
AF009606_FulllengthE2 ------------------------------------------------------------   363
AF009606_E2661       ------------------------------------------------------------   278
WT_E2661             ------------------------------------------------------------   278
Delta123             ------------------------------------------------------------   227

AF009606             PIIQRLHGLSAFSLHSYSPGEINRVAACLRKLGVPPLRAWHRARSVRARLLSRGGRAAI   2940
AF009606_FulllengthE2 ------------------------------------------------------------   363
AF009606_E2661       ------------------------------------------------------------   278
WT_E2661             ------------------------------------------------------------   278
Delta123             ------------------------------------------------------------   227

AF009606             CGKYLFNWAVRTKLKLTPIAAAGRLDLSGWFTAGYSGGDIYHSVSHARPRWFWFCLLLLA   3000
AF009606_FulllengthE2 ------------------------------------------------------------   363
AF009606_E2661       ------------------------------------------------------------   278
WT_E2661             ------------------------------------------------------------   278
Delta123             ------------------------------------------------------------   227

AF009606             AGVGIYLLPNR   3011
AF009606_FulllengthE2 -----------   363
AF009606_E2661       -----------   278
WT_E2661             -----------   278
Delta123             -----------   227
```

FIG. 14C (CONTINUED)

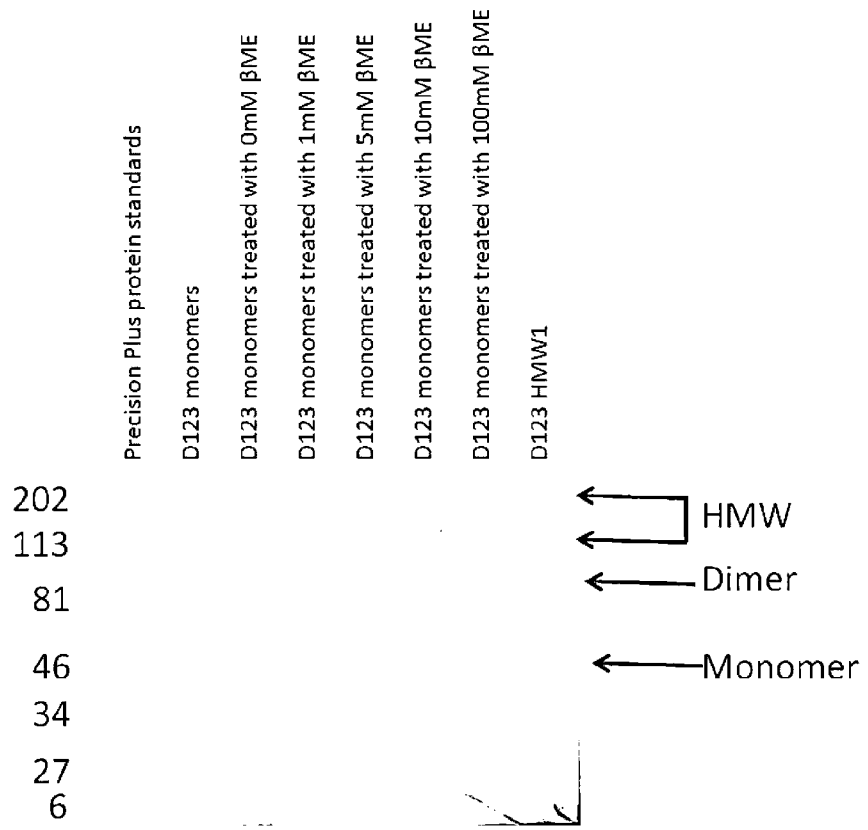
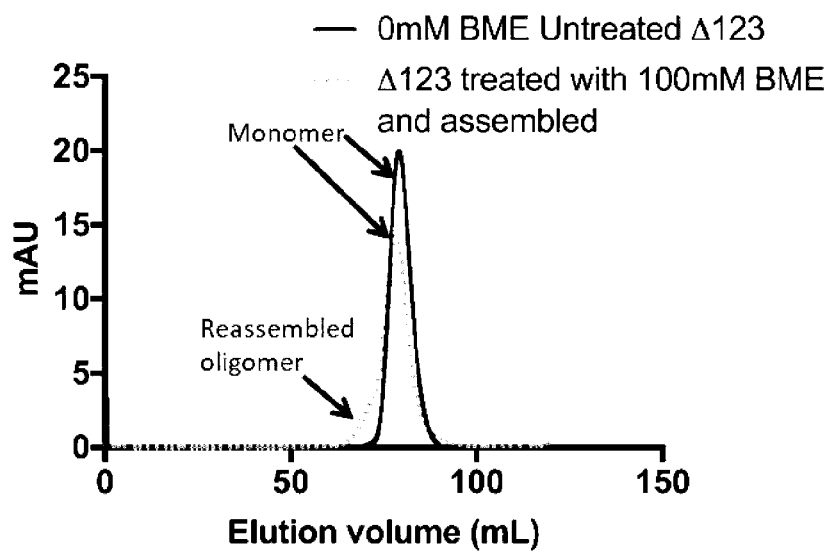
FIG. 15

A.
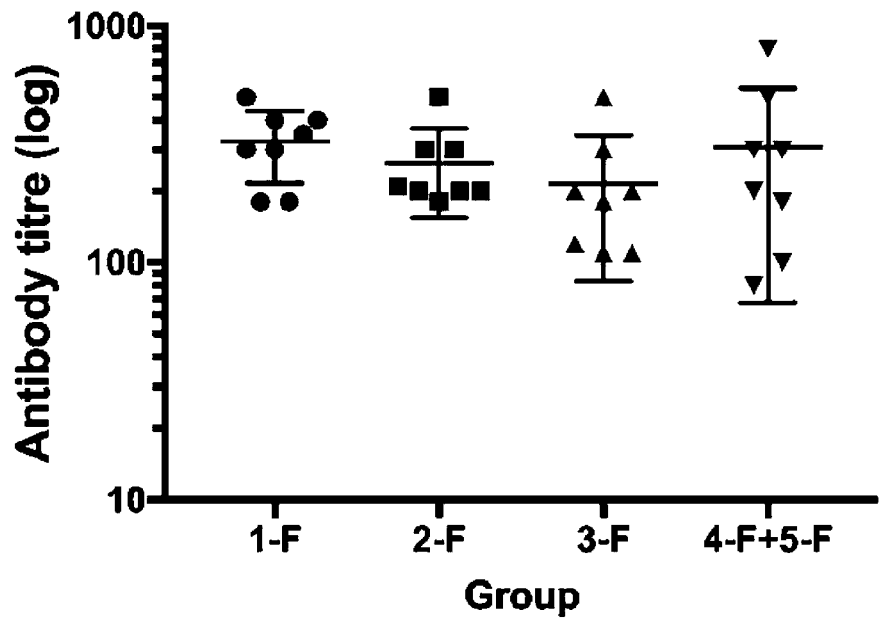
B.
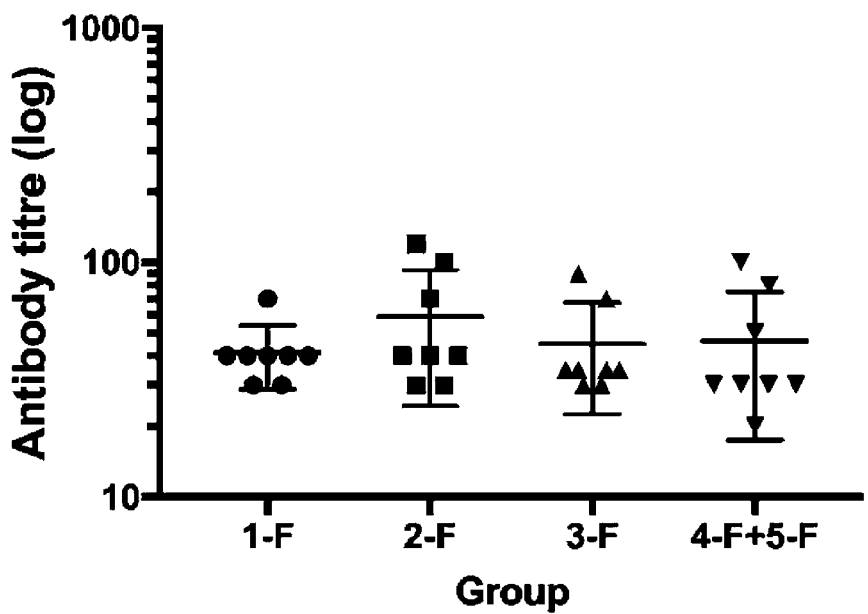
FIG. 20

SEQUENCE LISTING

```
<160> NUMBER OF SEQ ID NOS: 24

<210> SEQ ID NO 1
<211> LENGTH: 774
<212> TYPE: DNA
<213> ORGANISM: Artificial Sequence
<220> FEATURE:
<223> OTHER INFORMATION: Modified viral sequence

<400> SEQUENCE: 1
ggtaccgcta gcgccaccat gaaccccctg ctgatcctga cctttgtggc cgctgccctg      60
gccgagacac accagaacat ccagctgatc aacaccaacg gcagctggca catcaacagc     120
accgccctga actgcaacga gagcctgaac acaggctggc tggccggcct gttctaccag     180
cacaagttca acagcagcgg agcccccgag agactggcct cttgtggatc ttctggcgcc     240
tggcactacc cccctagacc ttgtggaatc gtgcccgcca gagcgtgtg cggccctgtg      300 tactgcttca cccctagccc tgtggtcgtg ggcaccaccg atagatctgg cgcccctacc     360
tattcctggg gcgccaacga caccgacgtg ttcgtgctga caacacccg gccacccctg      420 ggcaattggt tcggctgcac ctggatgaac tccaccggct tcaccaaagt gtgcggcgct     480
cctcctgccg gatccagcgg agcacctacc gacgccttca gaaagcaccc cgaggccacc     540
tactctagag ccggatctgg ccctggatc accccccagat gcatggtgga ctaccctac      600 cggctgtggc actatccctg caccatcaac tacaccatct tcaaagtgcg gatgtacgtg     660
ggcggcgtgg aacacagact ggaagccgcc tgcaactgga ccagaggcga gagagccgac     720
ctggaagatc gggacagaag cgagcaccac caccatcacc actgatgact cgag           774

<210> SEQ ID NO 2
<211> LENGTH: 747
<212> TYPE: DNA
<213> ORGANISM: Artificial Sequence
<220> FEATURE:
<223> OTHER INFORMATION: Modified viral sequence

<400> SEQUENCE: 2
atgaaccccc tgctgatcct gacctttgtg gccgctgccc tggccgagac acaccagaac      60
atccagctga tcaacaccaa cggcagctgg cacatcaaca gcaccgccct gaactgcaac     120
gagagcctga acacaggctg gctggccggc ctgttctacc agcacaagtt caacagcagc     180
ggagcccccg agagactggc ctcttgtgga tcttctggcg cctggcacta ccccctaga     240 ccttgtggaa tcgtgcccgc caagagcgtg tgcggccctg tgtactgctt cacccctagc     300
cctgtggtcg tgggcaccac cgatagatct ggcgcccta cctattcctg gggcgccaac     360
gacaccgacg tgttcgtgct gaacaacacc cggccacccc tgggcaattg gttcggctgc     420
acctggatga actccaccgg cttcaccaaa gtgtgcggcg ctcctcctgc cggatccagc     480
ggagcaccta ccgacgcctt cagaaagcac cccgaggcca cctactctag agccggatct     540
gggccctgga tcacccccag atgcatggtg gactacccct accggctgtg gcactatccc     600
tgcaccatca actacaccat cttcaaagtg cggatgtacg tgggcggcgt ggaacacaga     660
```

```
ctggaagccg cctgcaactg gaccagaggc gagagagccg acctggaaga tcgggacaga    720
agcgagcacc accaccatca ccactga                                        747

<210> SEQ ID NO 3
<211> LENGTH: 227
<212> TYPE: PRT
<213> ORGANISM: Artificial Sequence
<220> FEATURE:
<223> OTHER INFORMATION: Modified viral sequence

<400> SEQUENCE: 3

Glu Thr His Gln Asn Ile Gln Leu Ile Asn Thr Asn Gly Ser Trp His
1               5                   10                  15

Ile Asn Ser Thr Ala Leu Asn Cys Asn Glu Ser Leu Asn Thr Gly Trp
            20                  25                  30

Leu Ala Gly Leu Phe Tyr Gln His Lys Phe Asn Ser Ser Gly Ala Pro
        35                  40                  45

Glu Arg Leu Ala Ser Cys Gly Ser Ser Gly Ala Trp His Tyr Pro Pro
    50                  55                  60

Arg Pro Cys Gly Ile Val Pro Ala Lys Ser Val Cys Gly Pro Val Tyr
65                  70                  75                  80

Cys Phe Thr Pro Ser Pro Val Val Val Gly Thr Thr Asp Arg Ser Gly
                85                  90                  95

Ala Pro Thr Tyr Ser Trp Gly Ala Asn Asp Thr Asp Val Phe Val Leu
            100                 105                 110

Asn Asn Thr Arg Pro Pro Leu Gly Asn Trp Phe Gly Cys Thr Trp Met
        115                 120                 125

Asn Ser Thr Gly Phe Thr Lys Val Cys Gly Ala Pro Pro Ala Gly Ser
    130                 135                 140

Ser Gly Ala Pro Thr Asp Ala Phe Arg Lys His Pro Glu Ala Thr Tyr
145                 150                 155                 160

Ser Arg Ala Gly Ser Gly Pro Trp Ile Thr Pro Arg Cys Met Val Asp
                165                 170                 175

Tyr Pro Tyr Arg Leu Trp His Tyr Pro Cys Thr Ile Asn Tyr Thr Ile
            180                 185                 190

Phe Lys Val Arg Met Tyr Val Gly Gly Val Glu His Arg Leu Glu Ala
        195                 200                 205

Ala Cys Asn Trp Thr Arg Gly Glu Arg Ala Asp Leu Glu Asp Arg Asp
    210                 215                 220

Arg Ser Glu
225

<210> SEQ ID NO 4
<211> LENGTH: 278
<212> TYPE: PRT
<213> ORGANISM: Hepatitis C virus

<400> SEQUENCE: 4

Glu Thr His Val Thr Gly Gly Asn Ala Gly Arg Thr Thr Ala Gly Leu
1               5                   10                  15

Val Gly Leu Leu Thr Pro Gly Ala Lys Gln Asn Ile Gln Leu Ile Asn
            20                  25                  30

Thr Asn Gly Ser Trp His Ile Asn Ser Thr Ala Leu Asn Cys Asn Glu
        35                  40                  45

Ser Leu Asn Thr Gly Trp Leu Ala Gly Leu Phe Tyr Gln His Lys Phe
    50                  55                  60
```

```
Asn Ser Ser Gly Cys Pro Glu Arg Leu Ala Ser Cys Arg Arg Leu Thr
 65                  70                  75                  80

Asp Phe Ala Gln Gly Trp Gly Pro Ile Ser Tyr Ala Asn Gly Ser Gly
             85                  90                  95

Leu Asp Glu Arg Pro Tyr Cys Trp His Tyr Pro Pro Arg Pro Cys Gly
            100                 105                 110

Ile Val Pro Ala Lys Ser Val Cys Gly Pro Val Tyr Cys Phe Thr Pro
        115                 120                 125

Ser Pro Val Val Val Gly Thr Thr Asp Arg Ser Gly Ala Pro Thr Tyr
    130                 135                 140

Ser Trp Gly Ala Asn Asp Thr Asp Val Phe Val Leu Asn Asn Thr Arg
145                 150                 155                 160

Pro Pro Leu Gly Asn Trp Phe Gly Cys Thr Trp Met Asn Ser Thr Gly
                165                 170                 175

Phe Thr Lys Val Cys Gly Ala Pro Pro Cys Val Ile Gly Gly Val Gly
            180                 185                 190

Asn Asn Thr Leu Leu Cys Pro Thr Asp Cys Phe Arg Lys His Pro Glu
        195                 200                 205

Ala Thr Tyr Ser Arg Cys Gly Ser Gly Pro Trp Ile Thr Pro Arg Cys
    210                 215                 220

Met Val Asp Tyr Pro Tyr Arg Leu Trp His Tyr Pro Cys Thr Ile Asn
225                 230                 235                 240

Tyr Thr Ile Phe Lys Val Arg Met Tyr Val Gly Gly Val Glu His Arg
                245                 250                 255

Leu Glu Ala Ala Cys Asn Trp Thr Arg Gly Glu Arg Cys Asp Leu Glu
            260                 265                 270

Asp Arg Asp Arg Ser Glu
            275

<210> SEQ ID NO 5
<211> LENGTH: 227
<212> TYPE: PRT
<213> ORGANISM: Artificial Sequence
<220> FEATURE:
<223> OTHER INFORMATION: modified E2

<400> SEQUENCE: 5

Glu Thr His Gln Asn Ile Gln Leu Ile Asn Thr Asn Gly Ser Trp His
 1               5                  10                  15

Ile Asn Ser Thr Ala Leu Asn Cys Asn Glu Ser Leu Asn Thr Gly Trp
             20                  25                  30

Leu Ala Gly Leu Phe Tyr Gln His Lys Phe Asn Ser Ser Gly Cys Pro
         35                  40                  45

Glu Arg Leu Ala Ser Cys Gly Ser Ser Gly Cys Trp His Tyr Pro Pro
     50                  55                  60

Arg Pro Cys Gly Ile Val Pro Ala Lys Ser Val Cys Gly Pro Val Tyr
 65                  70                  75                  80

Cys Phe Thr Pro Ser Pro Val Val Val Gly Thr Thr Asp Arg Ser Gly
             85                  90                  95

Ala Pro Thr Tyr Ser Trp Gly Ala Asn Asp Thr Asp Val Phe Val Leu
            100                 105                 110

Asn Asn Thr Arg Pro Pro Leu Gly Asn Trp Phe Gly Cys Thr Trp Met
        115                 120                 125

Asn Ser Thr Gly Phe Thr Lys Val Cys Gly Ala Pro Pro Cys Gly Ser
    130                 135                 140
```

-continued

```
Ser Gly Cys Pro Thr Asp Cys Phe Arg Lys His Pro Glu Ala Thr Tyr
145                 150                 155                 160

Ser Arg Cys Gly Ser Gly Pro Trp Ile Thr Pro Arg Cys Met Val Asp
                165                 170                 175

Tyr Pro Tyr Arg Leu Trp His Tyr Pro Cys Thr Ile Asn Tyr Thr Ile
            180                 185                 190

Phe Lys Val Arg Met Tyr Val Gly Val Glu His Arg Leu Glu Ala
        195                 200                 205

Ala Cys Asn Trp Thr Arg Gly Glu Arg Cys Asp Leu Glu Asp Arg Asp
210                 215                 220

Arg Ser Glu
225

<210> SEQ ID NO 6
<211> LENGTH: 3011
<212> TYPE: PRT
<213> ORGANISM: Hepatitis C virus

<400> SEQUENCE: 6

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285
```

```
Gln Leu Phe Thr Phe Ser Pro Arg Arg His Trp Thr Thr Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Phe Ala Gly Val Asp Ala Glu
    370                 375                 380

Thr His Val Thr Gly Gly Ser Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
            420                 425                 430

Leu Asn Thr Gly Trp Leu Ala Gly Leu Phe Tyr Gln His Lys Phe Asn
        435                 440                 445

Ser Ser Gly Cys Pro Glu Arg Leu Ala Ser Cys Arg Arg Leu Thr Asp
    450                 455                 460

Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Pro Arg Pro Cys Gly Ile
                485                 490                 495

Val Pro Ala Lys Ser Val Cys Gly Pro Val Tyr Cys Phe Thr Pro Ser
            500                 505                 510

Pro Val Val Val Gly Thr Thr Asp Arg Ser Gly Ala Pro Thr Tyr Ser
        515                 520                 525

Trp Gly Ala Asn Asp Thr Asp Val Phe Val Leu Asn Asn Thr Arg Pro
    530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Val Gly Asn
                565                 570                 575

Asn Thr Leu Leu Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Met
        595                 600                 605

Val Asp Tyr Pro Tyr Arg Leu Trp His Tyr Pro Cys Thr Ile Asn Tyr
    610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700
```

-continued

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
        725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
                755                 760                 765

Leu Val Phe Phe Cys Phe Ala Trp Tyr Leu Lys Gly Arg Trp Val Pro
    770                 775                 780

Gly Ala Val Tyr Ala Phe Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Met Trp Trp Leu Gln Tyr
                835                 840                 845

Phe Leu Thr Arg Val Glu Ala Gln Leu His Val Trp Val Pro Pro Leu
850                 855                 860

Asn Val Arg Gly Gly Arg Asp Ala Val Ile Leu Leu Met Cys Val Val
865                 870                 875                 880

His Pro Thr Leu Val Phe Asp Ile Thr Lys Leu Leu Leu Ala Ile Phe
                885                 890                 895

Gly Pro Leu Trp Ile Leu Gln Ala Ser Leu Leu Lys Val Pro Tyr Phe
                900                 905                 910

Val Arg Val Gln Gly Leu Leu Arg Ile Cys Ala Leu Ala Arg Lys Ile
                915                 920                 925

Ala Gly Gly His Tyr Val Gln Met Ala Ile Ile Lys Leu Gly Ala Leu
930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Arg Met Glu Thr Lys Leu Ile Thr Trp Gly Ala Asp Thr Ala Ala
                980                 985                 990

Cys Gly Asp Ile Ile Asn Gly Leu Pro Val Ser Ala Arg Arg Gly Gln
                995                 1000                1005

Glu Ile Leu Leu Gly Pro Ala Asp Gly Met Val Ser Lys Gly Trp
    1010                1015                1020

Arg Leu Leu Ala Pro Ile Thr Ala Tyr Ala Gln Gln Thr Arg Gly
    1025                1030                1035

Leu Leu Gly Cys Ile Ile Thr Ser Leu Thr Gly Arg Asp Lys Asn
    1040                1045                1050

Gln Val Glu Gly Glu Val Gln Ile Val Ser Thr Ala Thr Gln Thr
    1055                1060                1065

Phe Leu Ala Thr Cys Ile Asn Gly Val Cys Trp Thr Val Tyr His
    1070                1075                1080

Gly Ala Gly Thr Arg Thr Ile Ala Ser Pro Lys Gly Pro Val Ile
    1085                1090                1095

Gln Met Tyr Thr Asn Val Asp Gln Asp Leu Val Gly Trp Pro Ala
    1100                1105                1110

-continued

```
Pro Gln Gly Ser Arg Ser Leu Thr Pro Cys Thr Cys Gly Ser Ser
    1115              1120              1125

Asp Leu Tyr Leu Val Thr Arg His Ala Asp Val Ile Pro Val Arg
    1130              1135              1140

Arg Arg Gly Asp Ser Arg Gly Ser Leu Leu Ser Pro Arg Pro Ile
    1145              1150              1155

Ser Tyr Leu Lys Gly Ser Ser Gly Gly Pro Leu Leu Cys Pro Ala
    1160              1165              1170

Gly His Ala Val Gly Leu Phe Arg Ala Ala Val Cys Thr Arg Gly
    1175              1180              1185

Val Ala Lys Ala Val Asp Phe Ile Pro Val Glu Asn Leu Glu Thr
    1190              1195              1200

Thr Met Arg Ser Pro Val Phe Thr Asp Asn Ser Ser Pro Pro Ala
    1205              1210              1215

Val Pro Gln Ser Phe Gln Val Ala His Leu His Ala Pro Thr Gly
    1220              1225              1230

Ser Gly Lys Ser Thr Lys Val Pro Ala Ala Tyr Ala Ala Gln Gly
    1235              1240              1245

Tyr Lys Val Leu Val Leu Asn Pro Ser Val Ala Ala Thr Leu Gly
    1250              1255              1260

Phe Gly Ala Tyr Met Ser Lys Ala His Gly Val Asp Pro Asn Ile
    1265              1270              1275

Arg Thr Gly Val Arg Thr Ile Thr Thr Gly Ser Pro Ile Thr Tyr
    1280              1285              1290

Ser Thr Tyr Gly Lys Phe Leu Ala Asp Gly Gly Cys Ser Gly Gly
    1295              1300              1305

Ala Tyr Asp Ile Ile Ile Cys Asp Glu Cys His Ser Thr Asp Ala
    1310              1315              1320

Thr Ser Ile Leu Gly Ile Gly Thr Val Leu Asp Gln Ala Glu Thr
    1325              1330              1335

Ala Gly Ala Arg Leu Val Val Leu Ala Thr Ala Thr Pro Pro Gly
    1340              1345              1350

Ser Val Thr Val Ser His Pro Asn Ile Glu Glu Val Ala Leu Ser
    1355              1360              1365

Thr Thr Gly Glu Ile Pro Phe Tyr Gly Lys Ala Ile Pro Leu Glu
    1370              1375              1380

Val Ile Lys Gly Gly Arg His Leu Ile Phe Cys His Ser Lys Lys
    1385              1390              1395

Lys Cys Asp Glu Leu Ala Ala Lys Leu Val Ala Leu Gly Ile Asn
    1400              1405              1410

Ala Val Ala Tyr Tyr Arg Gly Leu Asp Val Ser Val Ile Pro Thr
    1415              1420              1425

Ser Gly Asp Val Val Val Ser Thr Asp Ala Leu Met Thr Gly
    1430              1435              1440

Phe Thr Gly Asp Phe Asp Ser Val Ile Asp Cys Asn Thr Cys Val
    1445              1450              1455

Thr Gln Thr Val Asp Phe Ser Leu Asp Pro Thr Phe Thr Ile Glu
    1460              1465              1470

Thr Thr Thr Leu Pro Gln Asp Ala Val Ser Arg Thr Gln Arg Arg
    1475              1480              1485

Gly Arg Thr Gly Arg Gly Lys Pro Gly Ile Tyr Arg Phe Val Ala
    1490              1495              1500
```

```
Pro Gly Glu Arg Pro Ser Gly Met Phe Asp Ser Ser Val Leu Cys
1505                1510                1515

Glu Cys Tyr Asp Ala Gly Cys Ala Trp Tyr Glu Leu Thr Pro Ala
1520                1525                1530

Glu Thr Thr Val Arg Leu Arg Ala Tyr Met Asn Thr Pro Gly Leu
1535                1540                1545

Pro Val Cys Gln Asp His Leu Glu Phe Trp Glu Gly Val Phe Thr
1550                1555                1560

Gly Leu Thr His Ile Asp Ala His Phe Leu Ser Gln Thr Lys Gln
1565                1570                1575

Ser Gly Glu Asn Phe Pro Tyr Leu Val Ala Tyr Gln Ala Thr Val
1580                1585                1590

Cys Ala Arg Ala Gln Ala Pro Pro Ser Trp Asp Gln Met Trp
1595                1600                1605

Lys Cys Leu Ile Arg Leu Lys Pro Thr Leu His Gly Pro Thr Pro
1610                1615                1620

Leu Leu Tyr Arg Leu Gly Ala Val Gln Asn Glu Val Thr Leu Thr
1625                1630                1635

His Pro Ile Thr Lys Tyr Ile Met Thr Cys Met Ser Ala Asp Leu
1640                1645                1650

Glu Val Val Thr Ser Thr Trp Val Leu Val Gly Gly Val Leu Ala
1655                1660                1665

Ala Leu Ala Ala Tyr Cys Leu Ser Thr Gly Cys Val Val Ile Val
1670                1675                1680

Gly Arg Ile Val Leu Ser Gly Lys Pro Ala Ile Ile Pro Asp Arg
1685                1690                1695

Glu Val Leu Tyr Gln Glu Phe Asp Glu Met Glu Glu Cys Ser Gln
1700                1705                1710

His Leu Pro Tyr Ile Glu Gln Gly Met Met Leu Ala Glu Gln Phe
1715                1720                1725

Lys Gln Lys Ala Leu Gly Leu Leu Gln Thr Ala Ser Arg Gln Ala
1730                1735                1740

Glu Val Ile Thr Pro Ala Val Gln Thr Asn Trp Gln Lys Leu Glu
1745                1750                1755

Val Phe Trp Ala Lys His Met Trp Asn Phe Ile Ser Gly Ile Gln
1760                1765                1770

Tyr Leu Ala Gly Leu Ser Thr Leu Pro Gly Asn Pro Ala Ile Ala
1775                1780                1785

Ser Leu Met Ala Phe Thr Ala Ala Val Thr Ser Pro Leu Thr Thr
1790                1795                1800

Gly Gln Thr Leu Leu Phe Asn Ile Leu Gly Gly Trp Val Ala Ala
1805                1810                1815

Gln Leu Ala Ala Pro Gly Ala Ala Thr Ala Phe Val Gly Ala Gly
1820                1825                1830

Leu Ala Gly Ala Ala Ile Gly Ser Val Gly Leu Gly Lys Val Leu
1835                1840                1845

Val Asp Ile Leu Ala Gly Tyr Gly Ala Gly Val Ala Gly Ala Leu
1850                1855                1860

Val Ala Phe Lys Ile Met Ser Gly Glu Val Pro Ser Thr Glu Asp
1865                1870                1875

Leu Val Asn Leu Leu Pro Ala Ile Leu Ser Pro Gly Ala Leu Val
1880                1885                1890
```

-continued

Val Gly Val Val Cys Ala Ala Ile Leu Arg Arg His Val Gly Pro
    1895            1900                1905

Gly Glu Gly Ala Val Gln Trp Met Asn Arg Leu Ile Ala Phe Ala
    1910            1915                1920

Ser Arg Gly Asn His Val Ser Pro Thr His Tyr Val Pro Glu Ser
    1925            1930                1935

Asp Ala Ala Ala Arg Val Thr Ala Ile Leu Ser Ser Leu Thr Val
    1940            1945                1950

Thr Gln Leu Leu Arg Arg Leu His Gln Trp Ile Ser Ser Glu Cys
    1955            1960                1965

Thr Thr Pro Cys Ser Gly Ser Trp Leu Arg Asp Ile Trp Asp Trp
    1970            1975                1980

Ile Cys Glu Val Leu Ser Asp Phe Lys Thr Trp Leu Lys Ala Lys
    1985            1990                1995

Leu Met Pro Gln Leu Pro Gly Ile Pro Phe Val Ser Cys Gln Arg
    2000            2005                2010

Gly Tyr Arg Gly Val Trp Arg Gly Asp Gly Ile Met His Thr Arg
    2015            2020                2025

Cys His Cys Gly Ala Glu Ile Thr Gly His Val Lys Asn Gly Thr
    2030            2035                2040

Met Arg Ile Val Gly Pro Arg Thr Cys Arg Asn Met Trp Ser Gly
    2045            2050                2055

Thr Phe Pro Ile Asn Ala Tyr Thr Thr Gly Pro Cys Thr Pro Leu
    2060            2065                2070

Pro Ala Pro Asn Tyr Lys Phe Ala Leu Trp Arg Val Ser Ala Glu
    2075            2080                2085

Glu Tyr Val Glu Ile Arg Arg Val Gly Asp Phe His Tyr Val Ser
    2090            2095                2100

Gly Met Thr Thr Asp Asn Leu Lys Cys Pro Cys Gln Ile Pro Ser
    2105            2110                2115

Pro Glu Phe Phe Thr Glu Leu Asp Gly Val Arg Leu His Arg Phe
    2120            2125                2130

Ala Pro Pro Cys Lys Pro Leu Leu Arg Glu Glu Val Ser Phe Arg
    2135            2140                2145

Val Gly Leu His Glu Tyr Pro Val Gly Ser Gln Leu Pro Cys Glu
    2150            2155                2160

Pro Glu Pro Asp Val Ala Val Leu Thr Ser Met Leu Thr Asp Pro
    2165            2170                2175

Ser His Ile Thr Ala Glu Ala Ala Gly Arg Arg Leu Ala Arg Gly
    2180            2185                2190

Ser Pro Pro Ser Met Ala Ser Ser Ser Ala Ser Gln Leu Ser Ala
    2195            2200                2205

Pro Ser Leu Lys Ala Thr Cys Thr Ala Asn His Asp Ser Pro Asp
    2210            2215                2220

Ala Glu Leu Ile Glu Ala Asn Leu Leu Trp Arg Gln Glu Met Gly
    2225            2230                2235

Gly Asn Ile Thr Arg Val Glu Ser Glu Asn Lys Val Val Ile Leu
    2240            2245                2250

Asp Ser Phe Asp Pro Leu Val Ala Glu Glu Asp Glu Arg Glu Val
    2255            2260                2265

Ser Val Pro Ala Glu Ile Leu Arg Lys Ser Arg Arg Phe Ala Arg
    2270            2275                2280

```
Ala Leu Pro Val Trp Ala Arg Pro Asp Tyr Asn Pro Pro Leu Val
    2285                2290                2295

Glu Thr Trp Lys Lys Pro Asp Tyr Glu Pro Pro Val Val His Gly
    2300                2305                2310

Cys Pro Leu Pro Pro Pro Arg Ser Pro Pro Val Pro Pro Pro Arg
    2315                2320                2325

Lys Lys Arg Thr Val Val Leu Thr Glu Ser Thr Leu Ser Thr Ala
    2330                2335                2340

Leu Ala Glu Leu Ala Thr Lys Ser Phe Gly Ser Ser Ser Thr Ser
    2345                2350                2355

Gly Ile Thr Gly Asp Asn Thr Thr Thr Ser Ser Glu Pro Ala Pro
    2360                2365                2370

Ser Gly Cys Pro Pro Asp Ser Asp Val Glu Ser Tyr Ser Ser Met
    2375                2380                2385

Pro Pro Leu Glu Gly Glu Pro Gly Asp Pro Asp Leu Ser Asp Gly
    2390                2395                2400

Ser Trp Ser Thr Val Ser Ser Gly Ala Asp Thr Glu Asp Val Val
    2405                2410                2415

Cys Cys Ser Met Ser Tyr Ser Trp Thr Gly Ala Leu Val Thr Pro
    2420                2425                2430

Cys Ala Ala Glu Glu Gln Lys Leu Pro Ile Asn Ala Leu Ser Asn
    2435                2440                2445

Ser Leu Leu Arg His His Asn Leu Val Tyr Ser Thr Thr Ser Arg
    2450                2455                2460

Ser Ala Cys Gln Arg Gln Lys Lys Val Thr Phe Asp Arg Leu Gln
    2465                2470                2475

Val Leu Asp Ser His Tyr Gln Asp Val Leu Lys Glu Val Lys Ala
    2480                2485                2490

Ala Ala Ser Lys Val Lys Ala Asn Leu Leu Ser Val Glu Glu Ala
    2495                2500                2505

Cys Ser Leu Thr Pro Pro His Ser Ala Lys Ser Lys Phe Gly Tyr
    2510                2515                2520

Gly Ala Lys Asp Val Arg Cys His Ala Arg Lys Ala Val Ala His
    2525                2530                2535

Ile Asn Ser Val Trp Lys Asp Leu Leu Glu Asp Ser Val Thr Pro
    2540                2545                2550

Ile Asp Thr Thr Ile Met Ala Lys Asn Glu Val Phe Cys Val Gln
    2555                2560                2565

Pro Glu Lys Gly Gly Arg Lys Pro Ala Arg Leu Ile Val Phe Pro
    2570                2575                2580

Asp Leu Gly Val Arg Val Cys Glu Lys Met Ala Leu Tyr Asp Val
    2585                2590                2595

Val Ser Lys Leu Pro Leu Ala Val Met Gly Ser Ser Tyr Gly Phe
    2600                2605                2610

Gln Tyr Ser Pro Gly Gln Arg Val Glu Phe Leu Val Gln Ala Trp
    2615                2620                2625

Lys Ser Lys Lys Thr Pro Met Gly Phe Ser Tyr Asp Thr Arg Cys
    2630                2635                2640

Phe Asp Ser Thr Val Thr Glu Ser Asp Ile Arg Thr Glu Glu Ala
    2645                2650                2655

Ile Tyr Gln Cys Cys Asp Leu Asp Pro Gln Ala Arg Val Ala Ile
    2660                2665                2670
```

-continued

```
Lys Ser Leu Thr Glu Arg Leu Tyr Val Gly Gly Pro Leu Thr Asn
2675                2680                2685

Ser Arg Gly Glu Asn Cys Gly Tyr Arg Arg Cys Arg Ala Ser Gly
    2690                2695                2700

Val Leu Thr Thr Ser Cys Gly Asn Thr Leu Thr Cys Tyr Ile Lys
2705                2710                2715

Ala Arg Ala Ala Cys Arg Ala Ala Gly Leu Gln Asp Cys Thr Met
    2720                2725                2730

Leu Val Cys Gly Asp Asp Leu Val Val Ile Cys Glu Ser Ala Gly
2735                2740                2745

Val Gln Glu Asp Ala Ala Ser Leu Arg Ala Phe Thr Glu Ala Met
    2750                2755                2760

Thr Arg Tyr Ser Ala Pro Pro Gly Asp Pro Pro Gln Pro Glu Tyr
2765                2770                2775

Asp Leu Glu Leu Ile Thr Ser Cys Ser Ser Asn Val Ser Val Ala
    2780                2785                2790

His Asp Gly Ala Gly Lys Arg Val Tyr Tyr Leu Thr Arg Asp Pro
2795                2800                2805

Thr Thr Pro Leu Ala Arg Ala Ala Trp Glu Thr Ala Arg His Thr
    2810                2815                2820

Pro Val Asn Ser Trp Leu Gly Asn Ile Ile Met Phe Ala Pro Thr
2825                2830                2835

Leu Trp Ala Arg Met Ile Leu Met Thr His Phe Phe Ser Val Leu
    2840                2845                2850

Ile Ala Arg Asp Gln Leu Glu Gln Ala Leu Asn Cys Glu Ile Tyr
2855                2860                2865

Gly Ala Cys Tyr Ser Ile Glu Pro Leu Asp Leu Pro Pro Ile Ile
    2870                2875                2880

Gln Arg Leu His Gly Leu Ser Ala Phe Ser Leu His Ser Tyr Ser
2885                2890                2895

Pro Gly Glu Ile Asn Arg Val Ala Ala Cys Leu Arg Lys Leu Gly
    2900                2905                2910

Val Pro Pro Leu Arg Ala Trp Arg His Arg Ala Arg Ser Val Arg
2915                2920                2925

Ala Arg Leu Leu Ser Arg Gly Gly Arg Ala Ala Ile Cys Gly Lys
    2930                2935                2940

Tyr Leu Phe Asn Trp Ala Val Arg Thr Lys Leu Lys Leu Thr Pro
2945                2950                2955

Ile Ala Ala Ala Gly Arg Leu Asp Leu Ser Gly Trp Phe Thr Ala
    2960                2965                2970

Gly Tyr Ser Gly Gly Asp Ile Tyr His Ser Val Ser His Ala Arg
2975                2980                2985

Pro Arg Trp Phe Trp Phe Cys Leu Leu Leu Leu Ala Ala Gly Val
    2990                2995                3000

Gly Ile Tyr Leu Leu Pro Asn Arg
3005                3010

<210> SEQ ID NO 7
<211> LENGTH: 363
<212> TYPE: PRT
<213> ORGANISM: Hepatitis C virus
```

<400> SEQUENCE: 7

```
Glu Thr His Val Thr Gly Gly Ser Ala Gly Arg Thr Thr Ala Gly Leu
1               5                   10                  15

Val Gly Leu Leu Thr Pro Gly Ala Lys Gln Asn Ile Gln Leu Ile Asn
            20                  25                  30

Thr Asn Gly Ser Trp His Ile Asn Ser Thr Ala Leu Asn Cys Asn Glu
        35                  40                  45

Ser Leu Asn Thr Gly Trp Leu Ala Gly Leu Phe Tyr Gln His Lys Phe
50                  55                  60

Asn Ser Ser Gly Cys Pro Glu Arg Leu Ala Ser Cys Arg Arg Leu Thr
65                  70                  75                  80

Asp Phe Ala Gln Gly Trp Gly Pro Ile Ser Tyr Ala Asn Gly Ser Gly
                85                  90                  95

Leu Asp Glu Arg Pro Tyr Cys Trp His Tyr Pro Pro Arg Pro Cys Gly
            100                 105                 110

Ile Val Pro Ala Lys Ser Val Cys Gly Pro Val Tyr Cys Phe Thr Pro
            115                 120                 125

Ser Pro Val Val Val Gly Thr Thr Asp Arg Ser Gly Ala Pro Thr Tyr
130                 135                 140

Ser Trp Gly Ala Asn Asp Thr Asp Val Phe Val Leu Asn Asn Thr Arg
145                 150                 155                 160

Pro Pro Leu Gly Asn Trp Phe Gly Cys Thr Trp Met Asn Ser Thr Gly
            165                 170                 175

Phe Thr Lys Val Cys Gly Ala Pro Pro Cys Val Ile Gly Gly Val Gly
            180                 185                 190

Asn Asn Thr Leu Leu Cys Pro Thr Asp Cys Phe Arg Lys His Pro Glu
            195                 200                 205

Ala Thr Tyr Ser Arg Cys Gly Ser Gly Pro Trp Ile Thr Pro Arg Cys
            210                 215                 220

Met Val Asp Tyr Pro Tyr Arg Leu Trp His Tyr Pro Cys Thr Ile Asn
225                 230                 235                 240

Tyr Thr Ile Phe Lys Val Arg Met Tyr Val Gly Gly Val Glu His Arg
            245                 250                 255

Leu Glu Ala Ala Cys Asn Trp Thr Arg Gly Glu Arg Cys Asp Leu Glu
            260                 265                 270

Asp Arg Asp Arg Ser Glu Leu Ser Pro Leu Leu Leu Ser Thr Thr Gln
            275                 280                 285

Trp Gln Val Leu Pro Cys Ser Phe Thr Thr Leu Pro Ala Leu Ser Thr
290                 295                 300

Gly Leu Ile His Leu His Gln Asn Ile Val Asp Val Gln Tyr Leu Tyr
305                 310                 315                 320

Gly Val Gly Ser Ser Ile Ala Ser Trp Ala Ile Lys Trp Glu Tyr Val
            325                 330                 335

Val Leu Leu Phe Leu Leu Leu Ala Asp Ala Arg Val Cys Ser Cys Leu
            340                 345                 350

Trp Met Met Leu Leu Ile Ser Gln Ala Glu Ala
            355                 360
```

<210> SEQ ID NO 8
<211> LENGTH: 278
<212> TYPE: PRT
<213> ORGANISM: Hepatitis C virus -continued

```
<400> SEQUENCE: 8

Glu Thr His Val Thr Gly Gly Ser Ala Gly Arg Thr Thr Ala Gly Leu
1               5                   10                  15

Val Gly Leu Leu Thr Pro Gly Ala Lys Gln Asn Ile Gln Leu Ile Asn
            20                  25                  30

Thr Asn Gly Ser Trp His Ile Asn Ser Thr Ala Leu Asn Cys Asn Glu
        35                  40                  45

Ser Leu Asn Thr Gly Trp Leu Ala Gly Leu Phe Tyr Gln His Lys Phe
    50                  55                  60

Asn Ser Ser Gly Cys Pro Glu Arg Leu Ala Ser Cys Arg Arg Leu Thr
65                  70                  75                  80

Asp Phe Ala Gln Gly Trp Gly Pro Ile Ser Tyr Ala Asn Gly Ser Gly
                85                  90                  95

Leu Asp Glu Arg Pro Tyr Cys Trp His Tyr Pro Pro Arg Pro Cys Gly
            100                 105                 110

Ile Val Pro Ala Lys Ser Val Cys Gly Pro Val Tyr Cys Phe Thr Pro
        115                 120                 125

Ser Pro Val Val Val Gly Thr Thr Asp Arg Ser Gly Ala Pro Thr Tyr
    130                 135                 140

Ser Trp Gly Ala Asn Asp Thr Asp Val Phe Val Leu Asn Asn Thr Arg
145                 150                 155                 160

Pro Pro Leu Gly Asn Trp Phe Gly Cys Thr Trp Met Asn Ser Thr Gly
                165                 170                 175

Phe Thr Lys Val Cys Gly Ala Pro Pro Cys Val Ile Gly Gly Val Gly
            180                 185                 190

Asn Asn Thr Leu Leu Cys Pro Thr Asp Cys Phe Arg Lys His Pro Glu
        195                 200                 205

Ala Thr Tyr Ser Arg Cys Gly Ser Gly Pro Trp Ile Thr Pro Arg Cys
    210                 215                 220

Met Val Asp Tyr Pro Tyr Arg Leu Trp His Tyr Pro Cys Thr Ile Asn
225                 230                 235                 240

Tyr Thr Ile Phe Lys Val Arg Met Tyr Val Gly Gly Val Glu His Arg
                245                 250                 255

Leu Glu Ala Ala Cys Asn Trp Thr Arg Gly Glu Arg Cys Asp Leu Glu
            260                 265                 270

Asp Arg Asp Arg Ser Glu
        275

<210> SEQ ID NO 9
<211> LENGTH: 15
<212> TYPE: PRT
<213> ORGANISM: Artificial Sequence
<220> FEATURE:
<223> OTHER INFORMATION: N-Terminal signal sequence

<400> SEQUENCE: 9

Met Asn Pro Leu Leu Ile Leu Thr Phe Val Ala Ala Ala Leu Ala
1               5                   10                  15

<210> SEQ ID NO 10
<211> LENGTH: 353
<212> TYPE: PRT
<213> ORGANISM: Hepatitis C virus
```

<400> SEQUENCE: 10

```
Tyr Phe Ser Met Gln Ala Asn Trp Ala Lys Val Ile Leu Val Leu Phe
1               5                   10                  15

Leu Phe Ala Gly Val Asp Ala Glu Thr His Val Ser Gly Ala Ala Val
            20                  25                  30

Gly Arg Ser Thr Ala Gly Leu Ala Asn Leu Phe Ser Ser Gly Ser Lys
        35                  40                  45

Gln Asn Leu Gln Leu Ile Asn Ser Asn Gly Ser Trp His Ile Asn Arg
    50                  55                  60

Thr Ala Leu Asn Cys Asn Asp Ser Leu Asn Thr Gly Phe Leu Ala Ser
65                  70                  75                  80

Leu Phe Tyr Thr His Lys Phe Asn Ser Ser Gly Cys Ser Glu Arg Leu
            85                  90                  95

Ala Cys Cys Lys Ser Leu Asp Ser Tyr Gly Gln Gly Trp Gly Pro Leu
            100                 105                 110

Gly Val Ala Asn Ile Ser Gly Ser Ser Asp Asp Arg Pro Tyr Cys Trp
            115                 120                 125

His Tyr Ala Pro Arg Pro Cys Gly Ile Val Pro Ala Ser Ser Val Cys
130                 135                 140

Gly Pro Val Tyr Cys Phe Thr Pro Ser Pro Val Val Val Gly Thr Thr
145                 150                 155                 160

Asp His Val Gly Val Pro Thr Tyr Thr Trp Gly Glu Asn Glu Thr Asp
            165                 170                 175

Val Phe Leu Leu Asn Ser Thr Arg Pro Pro His Gly Ala Trp Phe Gly
            180                 185                 190

Cys Val Trp Met Asn Ser Thr Gly Phe Thr Lys Thr Cys Gly Ala Pro
            195                 200                 205

Pro Cys Glu Val Asn Thr Asn Asn Gly Thr Trp His Cys Pro Thr Asp
            210                 215                 220

Cys Phe Arg Lys His Pro Glu Thr Thr Tyr Ala Lys Cys Gly Ser Gly
225                 230                 235                 240

Pro Trp Ile Thr Pro Arg Cys Leu Ile Asp Tyr Pro Tyr Arg Leu Trp
            245                 250                 255

His Phe Pro Cys Thr Ala Asn Phe Ser Val Phe Asn Ile Arg Thr Phe
            260                 265                 270

Val Gly Gly Ile Glu His Arg Met Gln Ala Ala Cys Asn Trp Thr Arg
            275                 280                 285

Gly Glu Val Cys Gly Leu Glu His Arg Asp Arg Val Glu Leu Ser Pro
            290                 295                 300

Leu Leu Leu Thr Thr Thr Ala Trp Gln Ile Leu Pro Cys Ser Phe Thr
305                 310                 315                 320

Thr Leu Pro Ala Leu Ser Thr Gly Leu Ile His Leu His Gln Asn Ile
            325                 330                 335

Val Asp Val Gln Tyr Leu Tyr Gly Val Gly Ser Ala Val Val Ser Trp
            340                 345                 350

Ala
```

<210> SEQ ID NO 11
<211> LENGTH: 353
<212> TYPE: PRT
<213> ORGANISM: Hepatitis C virus

<400> SEQUENCE: 11

```
Tyr Phe Ser Met Val Gly Asn Trp Ala Lys Val Leu Val Val Leu Leu
1               5                   10                  15

Leu Phe Ala Gly Val Asp Ala Glu Thr His Val Thr Gly Gly Asn Ala
            20                  25                  30

Gly Arg Thr Thr Ala Gly Leu Val Gly Leu Leu Thr Pro Gly Ala Lys
        35                  40                  45

Gln Asn Ile Gln Leu Ile Asn Thr Asn Gly Ser Trp His Ile Asn Ser
    50                  55                  60

Thr Ala Leu Asn Cys Asn Glu Ser Leu Asn Thr Gly Trp Leu Ala Gly
65                  70                  75                  80

Leu Phe Tyr Gln His Lys Phe Asn Ser Ser Gly Cys Pro Glu Arg Leu
                85                  90                  95

Ala Ser Cys Arg Arg Leu Thr Asp Phe Ala Gln Gly Trp Gly Pro Ile
            100                 105                 110

Ser Tyr Ala Asn Gly Ser Gly Leu Asp Glu Arg Pro Tyr Cys Trp His
        115                 120                 125

Tyr Pro Pro Arg Pro Cys Gly Ile Val Pro Ala Lys Ser Val Cys Gly
130                 135                 140

Pro Val Tyr Cys Phe Thr Pro Ser Pro Val Val Val Gly Thr Thr Asp
145                 150                 155                 160

Arg Ser Gly Ala Pro Thr Tyr Ser Trp Gly Ala Asn Asp Thr Asp Val
                165                 170                 175

Phe Val Leu Asn Asn Thr Arg Pro Pro Leu Gly Asn Trp Phe Gly Cys
            180                 185                 190

Thr Trp Met Asn Ser Thr Gly Phe Thr Lys Val Cys Gly Ala Pro Pro
        195                 200                 205

Cys Val Ile Gly Gly Val Gly Asn Asn Thr Leu Leu Cys Pro Thr Asp
210                 215                 220

Cys Phe Arg Lys His Pro Glu Ala Thr Tyr Ser Arg Cys Gly Ser Gly
225                 230                 235                 240

Pro Trp Ile Thr Pro Arg Cys Met Val Asp Tyr Pro Tyr Arg Leu Trp
                245                 250                 255

His Tyr Pro Cys Thr Ile Asn Tyr Thr Ile Phe Lys Val Arg Met Tyr
            260                 265                 270

Val Gly Gly Val Glu His Arg Leu Glu Ala Ala Cys Asn Trp Thr Arg
        275                 280                 285

Gly Glu Arg Cys Asp Leu Glu Asp Arg Asp Arg Ser Glu Leu Ser Pro
290                 295                 300

Leu Leu Leu Ser Thr Thr Gln Trp Gln Val Leu Pro Cys Ser Phe Thr
305                 310                 315                 320

Thr Leu Pro Ala Leu Ser Thr Gly Leu Ile His Leu His Gln Asn Ile
                325                 330                 335

Val Asp Val Gln Tyr Leu Tyr Gly Val Gly Ser Ser Ile Ala Ser Trp
            340                 345                 350

Ala
```

<210> SEQ ID NO 12
<211> LENGTH: 354
<212> TYPE: PRT
<213> ORGANISM: Hepatitis C virus

```
<400> SEQUENCE: 12

Tyr Tyr Ala Ser Ala Ala Asn Trp Ala Lys Val Val Leu Val Leu Phe
1               5                   10                  15

Leu Phe Ala Gly Val Asp Ala Asn Thr Arg Thr Val Gly Gly Ser Ala
            20                  25                  30

Ala Gln Gly Ala Arg Gly Leu Ala Ser Leu Phe Thr Pro Gly Pro Gln
        35                  40                  45

Gln Asn Leu Gln Leu Ile Asn Thr Asn Gly Ser Trp His Ile Asn Arg
    50                  55                  60

Thr Ala Leu Asn Cys Asn Asp Ser Leu Gln Thr Gly Phe Val Ala Gly
65                  70                  75                  80

Leu Leu Tyr Tyr His Lys Phe Asn Ser Thr Gly Cys Pro Gln Arg Met
                85                  90                  95

Ala Ser Cys Arg Pro Leu Ala Ala Phe Asp Gln Gly Trp Gly Thr Ile
            100                 105                 110

Ser Tyr Ala Ala Val Ser Gly Pro Ser Asp Asp Lys Pro Tyr Cys Trp
        115                 120                 125

His Tyr Pro Pro Arg Pro Cys Gly Ile Val Pro Ala Arg Gly Val Cys
    130                 135                 140

Gly Pro Val Tyr Cys Phe Thr Pro Ser Pro Val Val Val Gly Thr Thr
145                 150                 155                 160

Asp Arg Lys Gly Asn Pro Thr Tyr Ser Trp Gly Glu Asn Glu Thr Asp
                165                 170                 175

Ile Phe Leu Leu Asn Asn Thr Arg Pro Pro Thr Gly Asn Trp Phe Gly
            180                 185                 190

Cys Thr Trp Met Asn Ser Thr Gly Phe Val Lys Thr Cys Gly Ala Pro
        195                 200                 205

Pro Cys Asn Leu Gly Pro Thr Gly Asn Asn Ser Leu Lys Cys Pro Thr
    210                 215                 220

Asp Cys Phe Arg Lys His Pro Asp Ala Thr Tyr Thr Lys Cys Gly Ser
225                 230                 235                 240

Gly Pro Trp Leu Thr Pro Arg Cys Leu Val His Tyr Pro Tyr Arg Leu
                245                 250                 255

Trp His Tyr Pro Cys Thr Leu Asn Tyr Thr Ile Phe Lys Val Arg Met
            260                 265                 270

Tyr Ile Gly Gly Leu Glu His Arg Leu Glu Val Ala Cys Asn Trp Thr
        275                 280                 285

Arg Gly Glu Arg Cys Asp Leu Glu Asp Arg Asp Arg Ala Glu Leu Ser
    290                 295                 300

Pro Leu Leu His Thr Thr Thr Gln Trp Ala Ile Leu Pro Cys Ser Phe
305                 310                 315                 320

Thr Pro Thr Pro Ala Leu Ser Thr Gly Leu Ile His Leu His Gln Asn
                325                 330                 335

Ile Val Asp Thr Gln Tyr Leu Tyr Gly Leu Ser Ser Ile Val Ser
            340                 345                 350

Trp Ala

<210> SEQ ID NO 13
<211> LENGTH: 359
<212> TYPE: PRT
<213> ORGANISM: Hepatitis C virus
```

<400> SEQUENCE: 13

```
Tyr Tyr Ser Met Gln Gly Asn Trp Ala Lys Val Ala Ile Val Met Ile
1               5                   10                  15

Met Phe Ser Gly Val Asp Ala Glu Thr Tyr Val Thr Gly Gly Ser Val
            20                  25                  30

Ala His Ser Ala Arg Gly Leu Thr Ser Leu Phe Ser Met Gly Ala Lys
        35                  40                  45

Gln Lys Leu Gln Leu Val Asn Thr Asn Gly Ser Trp His Ile Asn Ser
50                  55                  60

Thr Ala Leu Asn Cys Asn Glu Ser Ile Asn Thr Gly Phe Ile Ala Gly
65                  70                  75                  80

Leu Phe Tyr Tyr His Lys Phe Asn Ser Thr Gly Cys Pro Gln Arg Leu
                85                  90                  95

Ser Ser Cys Lys Pro Ile Ile Ser Phe Arg Gln Gly Trp Gly Pro Leu
            100                 105                 110

Thr Asp Ala Asn Ile Thr Gly Pro Ser Asp Asp Arg Pro Tyr Cys Trp
        115                 120                 125

His Tyr Ala Pro Arg Pro Cys Ser Val Val Pro Ala Ser Ser Val Cys
130                 135                 140

Gly Pro Val Tyr Cys Phe Thr Pro Ser Pro Val Val Gly Thr Thr
145                 150                 155                 160

Asp Ile Lys Gly Arg Pro Thr Tyr Asn Trp Gly Glu Asn Glu Thr Asp
                165                 170                 175

Val Phe Leu Leu Glu Ser Leu Arg Pro Pro Ser Gly Arg Trp Phe Gly
            180                 185                 190

Cys Ala Trp Met Asn Ser Thr Gly Phe Leu Lys Thr Cys Gly Ala Pro
        195                 200                 205

Pro Cys Asn Ile Tyr Gly Gly Glu Gly Asp Pro Glu Asn Glu Thr Asp
210                 215                 220

Leu Phe Cys Pro Thr Asp Cys Phe Arg Lys His Pro Glu Ala Thr Tyr
225                 230                 235                 240

Ser Arg Cys Gly Ala Gly Pro Trp Leu Thr Pro Arg Cys Met Val Asp
                245                 250                 255

Tyr Pro Tyr Arg Leu Trp His Tyr Pro Cys Thr Val Asn Phe Thr Leu
            260                 265                 270

Phe Lys Val Arg Met Phe Val Gly Gly Phe Glu His Arg Phe Thr Ala
        275                 280                 285

Ala Cys Asn Trp Thr Arg Gly Glu Arg Cys Asn Ile Glu Asp Arg Asp
290                 295                 300

Arg Ser Glu Gln His Pro Leu Leu His Ser Thr Thr Glu Leu Ala Ile
305                 310                 315                 320

Leu Pro Cys Ser Phe Thr Pro Met Pro Ala Leu Ser Thr Gly Leu Ile
                325                 330                 335

His Leu His Gln Asn Ile Val Asp Val Gln Tyr Leu Tyr Gly Val Gly
            340                 345                 350

Ser Asp Met Val Gly Trp Ala
        355
```

<210> SEQ ID NO 14
<211> LENGTH: 357
<212> TYPE: PRT
<213> ORGANISM: Hepatitis C virus

<400> SEQUENCE: 14

```
Tyr Phe Gly Met Ala Gly Asn Trp Leu Lys Val Leu Ala Val Leu Phe
1               5                   10                  15

Leu Phe Ala Gly Val Glu Ala Gln Thr Met Ile Ala His Gly Val Ser
            20                  25                  30

Gln Thr Thr Ser Gly Phe Ala Ser Leu Leu Thr Pro Gly Ala Lys Gln
        35                  40                  45

Asn Ile Gln Leu Ile Asn Thr Asn Gly Ser Trp His Ile Asn Arg Thr
    50                  55                  60

Ala Leu Asn Cys Asn Asp Ser Leu Gln Thr Gly Phe Leu Ala Ser Leu
65                  70                  75                  80

Phe Tyr Thr His Lys Phe Asn Ser Ser Gly Cys Pro Glu Arg Met Ala
                85                  90                  95

Ala Cys Lys Pro Leu Ala Glu Phe Arg Gln Gly Trp Gly Gln Ile Thr
            100                 105                 110

His Lys Asn Val Ser Gly Pro Ser Asp Asp Arg Pro Tyr Cys Trp His
        115                 120                 125

Tyr Ala Pro Arg Pro Cys Glu Val Val Pro Ala Arg Ser Val Cys Gly
    130                 135                 140

Pro Val Tyr Cys Phe Thr Pro Ser Pro Val Val Val Gly Thr Thr Asp
145                 150                 155                 160

Lys Arg Gly Asn Pro Thr Tyr Thr Trp Gly Glu Asn Glu Thr Asp Val
                165                 170                 175

Phe Met Leu Glu Ser Leu Arg Pro Pro Thr Gly Gly Trp Phe Gly Cys
            180                 185                 190

Thr Trp Met Asn Ser Thr Gly Phe Thr Lys Thr Cys Gly Ala Pro Pro
        195                 200                 205

Cys Gln Ile Val Pro Gly Asn Tyr Asn Ser Ser Ala Asn Glu Leu Leu
    210                 215                 220

Cys Pro Thr Asp Cys Phe Arg Lys His Pro Glu Ala Thr Tyr Gln Arg
225                 230                 235                 240

Cys Gly Ser Gly Pro Trp Val Thr Pro Arg Cys Leu Val Asp Tyr Ala
                245                 250                 255

Tyr Arg Leu Trp His Tyr Pro Cys Thr Val Asn Phe Thr Leu His Lys
            260                 265                 270

Val Arg Met Phe Val Gly Gly Thr Glu His Arg Phe Asp Val Ala Cys
        275                 280                 285

Asn Trp Thr Arg Gly Glu Arg Cys Glu Leu His Asp Arg Asn Arg Ile
    290                 295                 300

Glu Met Ser Pro Leu Leu Phe Ser Thr Thr Gln Leu Ser Ile Leu Pro
305                 310                 315                 320

Cys Ser Phe Ser Thr Met Pro Ala Leu Ser Thr Gly Leu Ile His Leu
                325                 330                 335

His Gln Asn Ile Val Asp Val Gln Tyr Leu Tyr Gly Val Ser Thr Asn
            340                 345                 350

Val Thr Ser Trp Val
        355
```

<210> SEQ ID NO 15
<211> LENGTH: 357
<212> TYPE: PRT
<213> ORGANISM: Hepatitis C virus

<400> SEQUENCE: 15

```
Tyr Phe Gly Met Ala Gly Asn Trp Ala Lys Val Ile Leu Ile Met Leu
1               5                   10                  15

Leu Met Ser Gly Val Asp Ala Glu Thr Met Ala Val Gly Ala Arg Ala
            20                  25                  30

Ala His Thr Thr Gly Ala Leu Val Ser Leu Leu Asn Pro Gly Pro Ser
        35                  40                  45

Gln Arg Leu Gln Leu Ile Asn Thr Asn Gly Ser Trp His Ile Asn Arg
    50                  55                  60

Thr Ala Leu Asn Cys Asn Asp Ser Leu Gln Thr Gly Phe Ile Ala Ala
65                  70                  75                  80

Leu Phe Tyr Thr His Arg Phe Asn Ser Ser Gly Cys Pro Glu Arg Met
            85                  90                  95

Ala Ser Cys Lys Pro Leu Ser Asp Phe Asp Gln Gly Trp Gly Pro Leu
        100                 105                 110

Trp Tyr Asn Ser Thr Glu Arg Pro Ser Asp Gln Arg Pro Tyr Cys Trp
    115                 120                 125

His Tyr Ala Pro Ser Pro Cys Gly Ile Val Pro Ala Lys Asp Val Cys
130                 135                 140

Gly Pro Val Tyr Cys Phe Thr Pro Ser Pro Val Val Val Gly Thr Thr
145                 150                 155                 160

Asp Arg Arg Gly Val Pro Thr Tyr Thr Trp Gly Glu Asn Glu Ser Asp
            165                 170                 175

Val Phe Leu Leu Asn Ser Thr Arg Pro Pro Gln Gly Ser Trp Phe Gly
        180                 185                 190

Cys Ser Trp Met Asn Thr Thr Gly Phe Thr Lys Thr Cys Gly Gly Pro
    195                 200                 205

Pro Cys Lys Ile Arg Pro Gln Gly Ala Gln Ser Asn Thr Ser Leu Thr
    210                 215                 220

Cys Pro Thr Asp Cys Phe Arg Lys His Pro Arg Ala Thr Tyr Ser Ala
225                 230                 235                 240

Cys Gly Ser Gly Pro Trp Leu Thr Pro Arg Cys Met Val His Tyr Pro
            245                 250                 255

Tyr Arg Leu Trp His Tyr Pro Cys Thr Val Asn Phe Thr Ile His Lys
        260                 265                 270

Val Arg Leu Tyr Ile Gly Gly Val Glu His Arg Leu Asp Ala Ala Cys
    275                 280                 285

Asn Trp Thr Arg Gly Glu Arg Cys Asp Leu Glu Asp Arg Asp Arg Val
    290                 295                 300

Asp Met Ser Pro Leu Leu His Ser Thr Thr Glu Leu Ala Ile Leu Pro
305                 310                 315                 320

Cys Ser Phe Val Pro Leu Pro Ala Leu Ser Thr Gly Leu Ile His Leu
            325                 330                 335

His Gln Asn Ile Val Asp Ala Gln Tyr Leu Tyr Gly Leu Ser Pro Ala
        340                 345                 350

Ile Ile Ser Trp Ala
        355
```

<210> SEQ ID NO 16
<211> LENGTH: 357
<212> TYPE: PRT
<213> ORGANISM: Hepatitis C virus

<400> SEQUENCE: 16

```
Tyr Phe Ser Met Gln Gly Ala Trp Ala Lys Val Val Ile Leu Leu
1               5                   10                  15

Leu Ala Ala Gly Val Asp Ala Arg Thr His Thr Val Gly Gly Ser Ala
                20                  25                  30

Ala Gln Thr Thr Gly Arg Leu Thr Ser Leu Phe Asp Met Gly Pro Arg
            35                  40                  45

Gln Lys Ile Gln Leu Val Asn Thr Asn Gly Ser Trp His Ile Asn Arg
50                  55                  60

Thr Ala Leu Asn Cys Asn Asp Ser Leu His Thr Gly Phe Ile Ala Ser
65                  70                  75                  80

Leu Phe Tyr Thr His Ser Phe Asn Ser Ser Gly Cys Pro Glu Arg Met
                85                  90                  95

Ser Ala Cys Arg Ser Ile Glu Ala Phe Arg Val Gly Trp Gly Ala Leu
                100                 105                 110

Gln Tyr Glu Asp Asn Val Thr Asn Pro Glu Asp Met Arg Pro Tyr Cys
            115                 120                 125

Trp His Tyr Pro Pro Arg Gln Cys Gly Val Val Ser Ala Lys Thr Val
130                 135                 140

Cys Gly Pro Val Tyr Cys Phe Thr Pro Ser Pro Val Val Val Gly Thr
145                 150                 155                 160

Thr Asp Arg Leu Gly Ala Pro Thr Tyr Thr Trp Gly Glu Asn Glu Thr
                165                 170                 175

Asp Val Phe Leu Leu Asn Ser Thr Arg Pro Pro Leu Gly Ser Trp Phe
            180                 185                 190

Gly Cys Thr Trp Met Asn Ser Ser Gly Tyr Thr Lys Thr Cys Gly Ala
                195                 200                 205

Pro Pro Cys Arg Thr Arg Ala Asp Phe Asn Ala Ser Thr Asp Leu Leu
210                 215                 220

Cys Pro Thr Asp Cys Phe Arg Lys His Pro Asp Thr Thr Tyr Leu Lys
225                 230                 235                 240

Cys Gly Ser Gly Pro Trp Leu Thr Pro Arg Cys Leu Ile Asp Tyr Pro
                245                 250                 255

Tyr Arg Leu Trp His Tyr Pro Cys Thr Val Asn Tyr Thr Ile Phe Lys
            260                 265                 270

Ile Arg Met Tyr Val Gly Gly Val Glu His Arg Leu Thr Ala Ala Cys
            275                 280                 285

Asn Phe Thr Arg Gly Asp Arg Cys Asn Leu Glu Asp Arg Asp Arg Ser
290                 295                 300

Gln Leu Ser Pro Leu Leu His Ser Thr Thr Glu Trp Ala Ile Leu Pro
305                 310                 315                 320

Cys Ser Tyr Ser Asp Leu Pro Ala Leu Ser Thr Gly Leu Leu His Leu
                325                 330                 335

His Gln Asn Ile Val Asp Val Gln Phe Met Tyr Gly Leu Ser Pro Ala
            340                 345                 350

Leu Thr Lys Tyr Ile
            355
```

<210> SEQ ID NO 17
<211> LENGTH: 632
<212> TYPE: PRT
<213> ORGANISM: Human immunodeficiency virus type 1

<400> SEQUENCE: 17

Glu Asn Leu Trp Val Thr Val Tyr Tyr Gly Val Pro Val Trp Lys Glu
1               5                   10                  15

Ala Thr Thr Thr Leu Phe Cys Ala Ser Asp Ala Lys Ala Tyr Asp Thr
            20                  25                  30

Glu Val His Asn Val Trp Ala Thr His Ala Cys Val Pro Thr Asp Pro
        35                  40                  45

Asn Pro Gln Glu Val Val Leu Glu Asn Val Thr Glu Asn Phe Asn Met
    50                  55                  60

Trp Lys Asn Asn Met Val Glu Gln Met His Glu Asp Ile Ile Ser Leu
65                  70                  75                  80

Trp Asp Gln Ser Leu Lys Pro Cys Val Lys Leu Thr Pro Leu Cys Val
                85                  90                  95

Thr Leu Asn Cys Thr Asp Leu Arg Asn Val Thr Ser Ser Glu Gly Met
            100                 105                 110

Arg Gly Glu Ile Lys Asn Cys Ser Phe Asn Ile Thr Thr Ser Ile Arg
        115                 120                 125

Asp Lys Val Lys Lys Asp Tyr Ala Leu Phe Tyr Arg Leu Asp Val Val
130                 135                 140

Pro Ile Asp Asn Asp Asn Thr Ser Tyr Arg Leu Ile Asn Cys Asn Thr
145                 150                 155                 160

Ser Thr Cys Thr Gln Ala Cys Pro Lys Val Ser Phe Glu Pro Ile Pro
                165                 170                 175

Ile His Tyr Cys Thr Pro Ala Gly Phe Ala Ile Leu Lys Cys Lys Asp
            180                 185                 190

Lys Lys Phe Asn Gly Thr Gly Pro Cys Lys Asn Val Ser Thr Val Gln
        195                 200                 205

Cys Thr His Gly Ile Arg Pro Val Val Ser Thr Gln Leu Leu Leu Asn
210                 215                 220

Gly Ser Leu Ala Glu Glu Val Val Ile Arg Ser Ser Asn Phe Thr
225                 230                 235                 240

Asp Asn Ala Lys Asn Ile Ile Val Gln Leu Lys Glu Ser Val Glu Ile
                245                 250                 255

Asn Cys Thr Arg Pro Asn Asn Asn Thr Arg Lys Ser Ile His Ile Gly
            260                 265                 270

Pro Gly Arg Cys Phe Tyr Thr Thr Gly Asp Ile Ile Gly Asp Ile Arg
        275                 280                 285

Gln Ala His Cys Asn Ile Ser Arg Thr Lys Trp Asn Asn Thr Leu Asn
290                 295                 300

Gln Ile Ala Thr Lys Leu Lys Glu Gln Phe Gly Asn Asn Lys Thr Ile
305                 310                 315                 320

Val Phe Asn Gln Ser Ser Gly Gly Asp Pro Glu Ile Val Met His Ser
                325                 330                 335

Phe Asn Cys Gly Gly Glu Phe Phe Tyr Cys Asn Ser Thr Gln Leu Phe
            340                 345                 350

Asn Ser Thr Trp Asn Phe Asn Gly Thr Trp Asn Leu Thr Gln Ser Asn
        355                 360                 365

Gly Thr Glu Gly Asn Asp Thr Ile Thr Leu Pro Cys Arg Ile Lys Gln
    370                 375                 380

Ile Ile Asn Met Trp Gln Glu Val Gly Lys Ala Met Tyr Ala Pro Pro
385                 390                 395                 400

```
Ile Arg Gly Gln Ile Arg Cys Ser Ser Asn Ile Thr Gly Leu Ile Leu
                405                 410                 415

Thr Arg Asp Gly Gly Asn Asn His Asn Asn Asp Thr Glu Thr Phe Arg
            420                 425                 430

Pro Gly Gly Gly Asp Met Arg Asp Asn Trp Arg Ser Glu Leu Tyr Lys
            435                 440                 445

Tyr Lys Val Val Lys Ile Glu Pro Leu Gly Val Ala Pro Thr Lys Cys
    450                 455                 460

Lys Arg Arg Val Val Gln Arg Arg Arg Lys Arg Ala Val Gly Thr
465                 470                 475                 480

Ile Gly Ala Met Phe Leu Gly Phe Leu Gly Ala Ala Gly Ser Thr Met
                485                 490                 495

Gly Ala Ala Ser Ile Thr Leu Thr Val Gln Ala Arg Leu Leu Leu Ser
            500                 505                 510

Gly Ile Val Gln Gln Gln Asn Asn Leu Leu Arg Ala Pro Glu Ala Gln
        515                 520                 525

Gln His Leu Leu Gln Leu Thr Val Trp Gly Ile Lys Gln Leu Gln Ala
    530                 535                 540

Arg Val Leu Ala Val Glu Arg Tyr Leu Arg Asp Gln Gln Leu Leu Gly
545                 550                 555                 560

Ile Trp Gly Cys Ser Gly Lys Leu Ile Cys Cys Thr Ala Val Pro Trp
                565                 570                 575

Asn Ala Ser Trp Ser Asn Lys Thr Leu Asp Met Ile Trp Asn Asn Met
            580                 585                 590

Thr Trp Met Glu Trp Glu Arg Glu Ile Asp Asn Tyr Thr Gly Leu Ile
        595                 600                 605

Tyr Thr Leu Ile Glu Glu Ser Gln Asn Gln Gln Glu Lys Asn Glu Gln
    610                 615                 620

Glu Leu Leu Glu Leu Asp Gly Ser
625                 630

<210> SEQ ID NO 18
<211> LENGTH: 661
<212> TYPE: PRT
<213> ORGANISM: Artificial Sequence
<220> FEATURE:
<223> OTHER INFORMATION: Amino acid residues corresponding to HIV1 env
      with N-terminal leader sequence and C-terminal HIS tag

<400> SEQUENCE: 18

Met Asp Ala Met Lys Arg Gly Leu Cys Cys Val Leu Leu Cys Gly
1               5                   10                  15

Ala Val Phe Val Ser Ala Ser Glu Asn Leu Trp Val Thr Val Tyr Tyr
                20                  25                  30

Gly Val Pro Val Trp Lys Glu Ala Thr Thr Thr Leu Phe Cys Ala Ser
            35                  40                  45

Asp Ala Lys Ala Tyr Asp Thr Glu Val His Asn Val Trp Ala Thr His
    50                  55                  60

Ala Cys Val Pro Thr Asp Pro Asn Pro Gln Glu Val Val Leu Glu Asn
65                  70                  75                  80

Val Thr Glu Asn Phe Asn Met Trp Lys Asn Asn Met Val Glu Gln Met
                85                  90                  95

His Glu Asp Ile Ile Ser Leu Trp Asp Gln Ser Leu Lys Pro Cys Val
            100                 105                 110
```

```
Lys Leu Thr Pro Leu Cys Val Thr Leu Asn Cys Thr Asp Leu Arg Asn
            115                 120                 125

Val Thr Ser Ser Glu Gly Met Arg Gly Glu Ile Lys Asn Cys Ser Phe
130                 135                 140

Asn Ile Thr Thr Ser Ile Arg Asp Lys Val Lys Lys Asp Tyr Ala Leu
145                 150                 155                 160

Phe Tyr Arg Leu Asp Val Val Pro Ile Asp Asn Asp Asn Thr Ser Tyr
            165                 170                 175

Arg Leu Ile Asn Cys Asn Thr Ser Thr Cys Thr Gln Ala Cys Pro Lys
            180                 185                 190

Val Ser Phe Glu Pro Ile Pro Ile His Tyr Cys Thr Pro Ala Gly Phe
            195                 200                 205

Ala Ile Leu Lys Cys Lys Asp Lys Lys Phe Asn Gly Thr Gly Pro Cys
            210                 215                 220

Lys Asn Val Ser Thr Val Gln Cys Thr His Gly Ile Arg Pro Val Val
225                 230                 235                 240

Ser Thr Gln Leu Leu Leu Asn Gly Ser Leu Ala Glu Glu Val Val
            245                 250                 255

Ile Arg Ser Ser Asn Phe Thr Asp Asn Ala Lys Asn Ile Ile Val Gln
            260                 265                 270

Leu Lys Glu Ser Val Glu Ile Asn Cys Thr Arg Pro Asn Asn Asn Thr
            275                 280                 285

Arg Lys Ser Ile His Ile Gly Pro Gly Arg Cys Phe Tyr Thr Thr Gly
            290                 295                 300

Asp Ile Ile Gly Asp Ile Arg Gln Ala His Cys Asn Ile Ser Arg Thr
305                 310                 315                 320

Lys Trp Asn Asn Thr Leu Asn Gln Ile Ala Thr Lys Leu Lys Glu Gln
            325                 330                 335

Phe Gly Asn Asn Lys Thr Ile Val Phe Asn Gln Ser Ser Gly Gly Asp
            340                 345                 350

Pro Glu Ile Val Met His Ser Phe Asn Cys Gly Gly Glu Phe Phe Tyr
            355                 360                 365

Cys Asn Ser Thr Gln Leu Phe Asn Ser Thr Trp Asn Phe Asn Gly Thr
            370                 375                 380

Trp Asn Leu Thr Gln Ser Asn Gly Thr Glu Gly Asn Asp Thr Ile Thr
385                 390                 395                 400

Leu Pro Cys Arg Ile Lys Gln Ile Ile Asn Met Trp Gln Glu Val Gly
            405                 410                 415

Lys Ala Met Tyr Ala Pro Pro Ile Arg Gly Gln Ile Arg Cys Ser Ser
            420                 425                 430

Asn Ile Thr Gly Leu Ile Leu Thr Arg Asp Gly Gly Asn Asn His Asn
            435                 440                 445

Asn Asp Thr Glu Thr Phe Arg Pro Gly Gly Gly Asp Met Arg Asp Asn
450                 455                 460

Trp Arg Ser Glu Leu Tyr Lys Tyr Lys Val Val Lys Ile Glu Pro Leu
465                 470                 475                 480

Gly Val Ala Pro Thr Lys Cys Lys Arg Val Val Gln Arg Arg
            485                 490                 495

Arg Lys Arg Ala Val Gly Thr Ile Gly Ala Met Phe Leu Gly Phe Leu
            500                 505                 510

Gly Ala Ala Gly Ser Thr Met Gly Ala Ala Ser Ile Thr Leu Thr Val
            515                 520                 525
```

```
Gln Ala Arg Leu Leu Leu Ser Gly Ile Val Gln Gln Asn Asn Leu
        530                 535                 540

Leu Arg Ala Pro Glu Ala Gln Gln His Leu Leu Gln Leu Thr Val Trp
545                 550                 555                 560

Gly Ile Lys Gln Leu Gln Ala Arg Val Leu Ala Val Glu Arg Tyr Leu
                565                 570                 575

Arg Asp Gln Gln Leu Leu Gly Ile Trp Gly Cys Ser Gly Lys Leu Ile
                580                 585                 590

Cys Cys Thr Ala Val Pro Trp Asn Ala Ser Trp Ser Asn Lys Thr Leu
                595                 600                 605

Asp Met Ile Trp Asn Asn Met Thr Trp Met Glu Trp Glu Arg Glu Ile
            610                 615                 620

Asp Asn Tyr Thr Gly Leu Ile Tyr Thr Leu Ile Glu Glu Ser Gln Asn
625                 630                 635                 640

Gln Gln Glu Lys Asn Glu Gln Glu Leu Leu Glu Leu Asp Gly Ser His
                645                 650                 655

His His His His His
            660

<210> SEQ ID NO 19
<211> LENGTH: 233
<212> TYPE: PRT
<213> ORGANISM: Artificial Sequence
<220> FEATURE:
<223> OTHER INFORMATION: H77cdelta123

<400> SEQUENCE: 19

Glu Thr His Gln Asn Ile Gln Leu Ile Asn Thr Asn Gly Ser Trp His
1               5                   10                  15

Ile Asn Ser Thr Ala Leu Asn Cys Asn Glu Ser Leu Asn Thr Gly Trp
            20                  25                  30

Leu Ala Gly Leu Phe Tyr Gln His Lys Phe Asn Ser Ser Gly Cys Pro
        35                  40                  45

Glu Arg Leu Ala Ser Cys Gly Ser Ser Gly Cys Trp His Tyr Pro Pro
    50                  55                  60

Arg Pro Cys Gly Ile Val Pro Ala Lys Ser Val Cys Gly Pro Val Tyr
65                  70                  75                  80

Cys Phe Thr Pro Ser Pro Val Val Val Gly Thr Thr Asp Arg Ser Gly
                85                  90                  95

Ala Pro Thr Tyr Ser Trp Gly Ala Asn Asp Thr Asp Val Phe Val Leu
            100                 105                 110

Asn Asn Thr Arg Pro Pro Leu Gly Asn Trp Phe Gly Cys Thr Trp Met
        115                 120                 125

Asn Ser Thr Gly Phe Thr Lys Val Cys Gly Ala Pro Pro Cys Gly Ser
130                 135                 140

Ser Gly Cys Pro Thr Asp Cys Phe Arg Lys His Pro Glu Ala Thr Tyr
145                 150                 155                 160

Ser Arg Cys Gly Ser Gly Pro Trp Ile Thr Pro Arg Cys Met Val Asp
                165                 170                 175

Tyr Pro Tyr Arg Leu Trp His Tyr Pro Cys Thr Ile Asn Tyr Thr Ile
            180                 185                 190

Phe Lys Val Arg Met Tyr Val Gly Gly Val Glu His Arg Leu Glu Ala
        195                 200                 205

Ala Cys Asn Trp Thr Arg Gly Glu Arg Cys Asp Leu Glu Asp Arg Asp
    210                 215                 220
```

Arg Ser Glu His His His His His
225                     230

<210> SEQ ID NO 20
<211> LENGTH: 228
<212> TYPE: PRT
<213> ORGANISM: Artificial Sequence
<220> FEATURE:
<223> OTHER INFORMATION: Con1delta123

<400> SEQUENCE: 20

Gly Thr Tyr Gly Ser Ser Gly Gln Leu Val Asn Thr Asn Gly Ser Trp
1               5                   10                  15

His Ile Asn Arg Thr Ala Leu Asn Cys Asn Asp Ser Leu Asn Thr Gly
            20                  25                  30

Phe Leu Ala Ala Leu Phe Tyr Val His Lys Phe Asn Ser Ser Gly Cys
        35                  40                  45

Pro Glu Arg Met Ala Ser Cys Gly Ser Ser Gly Cys Trp His Tyr Ala
    50                  55                  60

Pro Arg Pro Cys Gly Ile Val Pro Ala Ala Gln Val Cys Gly Pro Val
65                  70                  75                  80

Tyr Cys Phe Thr Pro Ser Pro Val Val Gly Thr Thr Asp Arg Phe
                85                  90                  95

Gly Val Pro Thr Tyr Ser Trp Gly Glu Asn Glu Thr Asp Val Leu Leu
            100                 105                 110

Leu Asn Asn Thr Arg Pro Pro Gln Gly Asn Trp Phe Gly Cys Thr Trp
            115                 120                 125

Met Asn Ser Thr Gly Phe Thr Lys Thr Cys Gly Gly Pro Pro Cys Gly
130                 135                 140

Ser Ser Gly Cys Pro Thr Asp Cys Phe Arg Lys His Pro Glu Ala Thr
145                 150                 155                 160

Tyr Thr Lys Cys Gly Ser Gly Pro Trp Leu Thr Pro Arg Cys Leu Val
                165                 170                 175

His Tyr Pro Tyr Arg Leu Trp His Tyr Pro Cys Thr Val Asn Phe Thr
            180                 185                 190

Ile Phe Lys Val Arg Met Tyr Val Gly Gly Val Glu His Arg Leu Glu
            195                 200                 205

Ala Ala Cys Asn Trp Thr Arg Gly Glu Arg Cys Asn Leu Glu Asp Arg
        210                 215                 220

Asp Arg Ser Glu
225

<210> SEQ ID NO 21
<211> LENGTH: 227
<212> TYPE: PRT
<213> ORGANISM: Artificial Sequence
<220> FEATURE:
<223> OTHER INFORMATION: S52delta123

<400> SEQUENCE: 21

Glu Thr His Gln Lys Leu Gln Leu Val Asn Thr Asn Gly Ser Trp His
1               5                   10                  15

Ile Asn Ser Thr Ala Leu Asn Cys Asn Glu Ser Ile Asn Thr Gly Phe
            20                  25                  30

Ile Ala Gly Leu Phe Tyr Tyr His Lys Phe Asn Ser Thr Gly Cys Pro
        35                  40                  45

Gln Arg Leu Ser Ser Cys Gly Ser Ser Gly Cys Trp His Tyr Ala Pro
    50                  55                  60

```
Arg Pro Cys Ser Val Val Pro Ala Ser Ser Val Cys Gly Pro Val Tyr
 65                  70                  75                  80

Cys Phe Thr Pro Ser Pro Val Val Val Gly Thr Thr Asp Ile Lys Gly
                 85                  90                  95

Lys Pro Thr Tyr Asn Trp Gly Glu Asn Glu Thr Asp Val Phe Leu Leu
                100                 105                 110

Glu Ser Leu Arg Pro Pro Ser Gly Arg Trp Phe Gly Cys Ala Trp Met
            115                 120                 125

Asn Ser Thr Gly Phe Leu Lys Thr Cys Gly Ala Pro Pro Cys Gly Ser
        130                 135                 140

Ser Gly Cys Pro Thr Asp Cys Phe Arg Lys His Pro Glu Ala Thr Tyr
145                 150                 155                 160

Ser Arg Cys Gly Ala Gly Pro Trp Leu Thr Pro Arg Cys Met Val Asp
                165                 170                 175

Tyr Pro Tyr Arg Leu Trp His Tyr Pro Cys Thr Val Asn Phe Thr Leu
                180                 185                 190

Phe Lys Val Arg Met Phe Val Gly Gly Phe Glu His Arg Phe Thr Ala
            195                 200                 205

Ala Cys Asn Trp Thr Arg Gly Glu Arg Cys Asn Ile Glu Asp Arg Asp
210                 215                 220

Arg Ser Glu
225

<210> SEQ ID NO 22
<211> LENGTH: 15
<212> TYPE: PRT
<213> ORGANISM: Artificial Sequence
<220> FEATURE:
<223> OTHER INFORMATION: human trypsinogen signal peptide

<400> SEQUENCE: 22

Met Asn Pro Leu Leu Ile Leu Thr Phe Val Ala Ala Leu Ala
1               5                   10                  15

<210> SEQ ID NO 23
<211> LENGTH: 23
<212> TYPE: PRT
<213> ORGANISM: Artificial Sequence
<220> FEATURE:
<223> OTHER INFORMATION: human tissue plasminogen activator signal
      peptide (tPA)

<400> SEQUENCE: 23

Met Asp Ala Met Lys Arg Gly Leu Cys Cys Val Leu Leu Leu Cys Gly
1               5                   10                  15

Ala Val Phe Val Ser Ala Ser
                20

<210> SEQ ID NO 24
<211> LENGTH: 6
<212> TYPE: PRT
<213> ORGANISM: Artificial Sequence
<220> FEATURE:
<223> OTHER INFORMATION: 6 HIS tag

<400> SEQUENCE: 24

His His His His His His
1               5
```

METHOD FOR PREPARING MULTIMERIC FORMS OF THE HEPATITIS C VIRUS (HCV) ENVELOPE GLYCOPROTEIN 2 (HCV E2)

CROSS-REFERENCE TO RELATED APPLICATIONS

This application is a U.S. National Phase under 35 U.S.C. § 371 of International Application No. PCT/AU2017/051037, filed Sep. 22. 2017, which claims priority to Australian Patent Application No. 2016903961, filed Sep. 29, 2016, each of which is hereby incorporated by reference in its entirety into this application.

FIELD

The present specification relates generally to vaccine and diagnostic compositions. In particular, the specification facilitates the production of higher order forms of antigens of interest, such as HCV envelope 2 (E2)glycoprotein and HIV envelope protein. Higher order antigens are suitable for vaccine production and ex vivo binding applications.

BACKGROUND

Bibliographic details of references in the subject specification are also listed at the end of the specification.

Reference to any prior art in this specification is not, and should not be taken as, acknowledgement or any form of suggestion that this prior art forms part of the common general knowledge in any country.

Hepatitis C virus is a highly variable pathogen that chronically infects 3% of the world's population and is a major cause of chronic liver disease. HCV circulates as 7 highly divergent genotypes (G1-G7) and over 67 subtypes (a, b, c etc.), for which no preventative vaccine is available. Recently, direct acting antivirals (DAAs) have reached the clinic enabling viral clearance to be achieved in >95% of treated individuals. However, DAAs cannot prevent reinfection and their high cost places a major economic burden on health care systems. Furthermore, an estimated 50 million people have undiagnosed infections providing a means for continued viral spread. A prophylactic vaccine would prevent new infections, and possibly reinfections, and significantly augment elimination programs involving the use of DAAs. A prophylactic vaccine has therefore been recognized by the World Health Organization as a priority for development.

The major surface glycoprotein, E2 attaches virions to the host cell receptor CD81 and generates genotype specific and broadly (cross-genotype protective) neutralizing antibodies (bNAbs). In natural infections, 30% of individuals clear their infection spontaneously and this has been correlated with rapid induction of bNAb and broadly reactive T cell responses. In addition, cocktails of broadly neutralizing monoclonal antibodies (NMAb) can prevent and clear established HCV infection in small animal models of HCV. However, previous vaccination studies conducted in animals using vaccines containing full-length or truncated forms of E2 and a phase I clinical trial of recombinant HCV glycoproteins did not elicit high titre NAbs, and very limited cross-genotype neutralization was observed. HCV E2 is highly glycosylated, undergoes rapid sequence change and possesses multiple variable regions, which are all implicated in immune evasion. Non-neutralizing antibodies have been proposed to interfere with the binding of neutralizing antibodies.

Prior art approaches to developing improved HCV vaccines have focused on modifying E2 to remove variable regions while retaining CD81 binding. Recently, the inventors determined that oligomeric and particularly, high molecular weight oligomers (HMW forms) are better than monomers at generating the desired broadly neutralizing antibody responses. This approach has been promising but high molecular weight (HMW) forms of wild type HCV E2 and modified E2 lacking hypervariable regions (e.g. Delta123 HCV E2) are generally expressed in low yield and are structurally heterogeneous which creates challenges for vaccine production. Currently oligomers are produced by transfection of plasmids expressing E2 into host cells and allowing the cell to fold E2 into native oligomers. Oligomers are then separated from other components as required.

It is against this background that the present inventor/s have developed a strategy for producing oligomeric forms of E2 with several potential advantages for commercial vaccine manufacture purposes, such as, in some embodiments, reduced cost and complexity of purification. The method is broadly applicable to any antigen of interest and for the production of assembled higher order forms of an antigen.

SUMMARY

In one aspect, the disclosure enables a method of preparing an extracellularly assembled higher order antigen from a native lower order antigen, the method comprising the following steps: (i) contacting a lower order antigen with a solution comprising a reducing agent for a time and under conditions sufficient to reduce one or more native cysteines; and (ii) removing or diluting the reducing agent or contacting the reduced lower order antigen with an oxidising agent, to elicit assembly of lower order antigen from (i) into an assembled higher order antigen. In one embodiment of the method, at least 10% of the lower order antigen is converted to higher order antigen in step (ii). In one embodiment of the method, the assembled higher order antigen displays at least reduced binding to non-neutralizing antibodies compared to the lower order antigen. In one embodiment of the method, the assembled higher order antigen retains binding to at least one neutralizing antibody.

In one embodiment, the antigen is a viral envelope antigen. In one embodiment the viral envelope antigen is HCV or HIV.

In another embodiment, the antigen is a cancer antigen.

In one embodiment, the higher order cancer antigen is a tetramer, pentamer, hexamer, decamer etc up to a 23mer.

In one embodiment, there is provided a method of preparing an extracellularly assembled higher order antigen from a native lower order antigen, the method comprising the following steps: (i) contacting a lower order antigen with a solution comprising a reducing agent for a time and under conditions sufficient to reduce one or more native cysteines; and (ii) removing or diluting the reducing agent or contacting the reduced lower order antigen with an oxidising agent, to elicit assembly of lower order antigen from (i) into an assembled higher order antigen; wherein at least 10% of the lower order antigen is converted to higher order antigen in step (ii) and whereby the assembled higher order antigen displays at least reduced binding to non-neutralizing antibodies compared to the lower order antigen and retains binding to at least one neutralizing antibody.

In one embodiment, higher order antigen is purified and mixed with a pharmaceutically acceptable diluent, carrier or adjuvant prior to delivery to a subject as a preventative or therapeutic vaccine.

In one embodiment, the disclosure enables a method of preparing extracellularly assembled higher order hepatitis C virus (HCV) envelope glycoprotein 2 (E2) antigen from native lower order HCV E2 the method comprising the following steps: (i) contacting lower order E2 with a solution comprising a reducing agent for a time and under conditions sufficient to reduce one or more native cysteines; and (ii) removing or diluting the reducing agent or contacting the reduced E2 with an oxidising agent, to elicit reassembly of lower order E2 from (i) into higher order HCV E2. In one embodiment of the method at least 20% of the lower order E2 antigen is assembled in to higher order antigen in step (ii). In one embodiment, the assembled higher order HCV E2 displays at least reduced binding to non-neutralizing antibodies compared to the lower order E2 and retains binding to at least one neutralizing antibody.

Accordingly, in one embodiment, the disclosure enables a method of preparing extracellularly assembled higher order hepatitis C virus (HCV) envelope glycoprotein 2 (E2) antigen from native lower order HCV E2 the method comprising the following steps: (i) contacting lower order E2 with a solution comprising a reducing agent for a time and under conditions sufficient to reduce one or more native cysteines; and (ii) removing or diluting the reducing agent or contacting the reduced E2 with an oxidising agent, to elicit reassembly of lower order E2 from (i) into higher order HCV E2, wherein at least 20% of the lower order antigen is assembled in to higher order antigen in step (ii) and whereby the assembled higher order HCV E2 displays at least reduced binding to non-neutralizing antibodies compared to the lower order E2 and retains binding to at least one neutralizing antibody.

In another one embodiment, the disclosure enables a method of preparing extracellularly assembled higher order HIV envelope glycoprotein antigen from native lower order HIV env the method comprising the following steps: (i) contacting lower order HIV env with a solution comprising a reducing agent for a time and under conditions sufficient to reduce one or more native cysteines; and (ii) removing or diluting the reducing agent or contacting the reduced Env with an oxidising agent, to elicit reassembly of lower order Env from (i) into higher order HIV Env, wherein at least 10% of the lower order antigen is assembled into higher order antigen in step (ii).

In one embodiment, first steps (i) and (ii) are repeated with a solution comprising residual lower order antigen from step (ii) in order to improve the efficiency of the method of assembly of lower order antigen into higher order antigen.

Surprisingly, even cysteine modified versions of HCV E2 monomers, such as the Ala7 construct also assemble into higher order forms using the presently described methods. As cysteine modified forms such as Ala7 are expressed recombinantly in predominantly monomeric form it would be useful to produce higher order forms from this material rather than purifying monomeric forms from a mixture of different forms as are usually produced with, for example, HCV E2 RBD forms or Delta123 forms. Thus, the finding that cysteine modified forms also assemble in the present methods facilitate vaccine manufacture by providing a useful source of lower order or monomer. Furthermore, as determined herein lower order antigen that did not initially assemble into higher order forms was able to form higher order forms when the method was repeated, enabling even higher yields of higher order forms.

In one embodiment of the method, in step (i) or prior to step (i) the solution comprising lower order antigen is substantially depleted of native oligomer or higher order antigen.

In one embodiment, at least 25%, at least 30%, at least 40%, at least 50%, at least 60% or at least 70%, or at least 80%, or at least 90% or at least 95% or more of the lower order antigen is converted into higher order antigen.

In another embodiment, the inventors found genotype specific differences in the yield of higher order antigen. Accordingly, in one embodiment, the method further comprises selecting a viral or antigen genotype which generates the greatest yield of assembled oligomeric antigen.

In one embodiment, the assembled higher order antigen retains or exceeds the ability of a native control higher order antigen to bind or elicit one or more neutralizing antibodies.

In one embodiment, the assembled higher order antigen is the receptor-binding domain (RBD) of HCV E2.

In one embodiment, the assembled higher order HCV E2 antigen lacks all or part of a hypervariable region such as one or more of hypervariable region 1 (HVR1) or a part thereof, the hypervariable region 2 (HVR2) or a part thereof and/or the intergenotypic variable region (igVR/VR3) or a part thereof.

In one embodiment, the assembled oligomeric antigen comprises a non-cysteine substitution or mutation in one or more of amino acid residues selected from the group comprising: C581, C585, C652, C677, C494, C486, C459, C452, C564, C597, and C569. As discussed herein use of cysteine modified forms surprisingly provides a source of lower order antigen able to assemble into higher order forms.

In another aspect, the disclosure provides a method of producing a vaccine composition comprising the herein disclosed assembly method comprising the following steps: (i) contacting a lower order antigen with a solution comprising a reducing agent for a time and under conditions sufficient to reduce one or more native cysteines; and (ii) removing or diluting the reducing agent or contacting the reduced lower order antigen with an oxidising agent, to elicit assembly of lower order antigen from (i) into an assembled higher order antigen, after which the assembled higher order antigen is admixed with a pharmaceutically or physiologically acceptable diluent, carrier or an adjuvant.

In some embodiments, the antigen is a viral envelope antigen or cancer antigen.

In some embodiments, the viral envelope antigen is a hepatitis virus antigen or an HIV envelope antigen.

In another aspect, the disclosure provides an assembled higher order antigen, or composition comprising same, produced from a lower order antigen by the herein disclosed method comprising the following steps: (i) contacting a lower order antigen with a solution comprising a reducing agent for a time and under conditions sufficient to reduce one or more native cysteines; and (ii) removing or diluting the reducing agent or contacting the reduced lower order antigen with an oxidising agent, to elicit assembly of lower order antigen from (i) into an assembled higher order antigen.

In one embodiment there is a enabled a composition comprising a higher order extracellularly assembled antigen. In one embodiment, the higher order assembled antigen displays a more favourable immunogenic profile compared to the counterpart control antigen produced in a host cell. In one embodiment, a favourable immunogenic profile includes greater occlusion of one or more non-neutralizing epitopes and/or greater exposure of one or more neutralizing epitopes of viral envelope antigens. In one embodiment, a favourable immunogenic profile includes an assembled antigen determining a more effective immune response compared to the counterpart control antigen assembled into higher order antigen in the environment of the host cell. In one embodiment a favourable immunogenic profile includes a stronger immune response able to reduce or prevent tumour development in a subject. In one embodiment, the assembled antigen is distinguishable from a native control higher order antigen by displaying reduced binding to the non-neutralizing antibody compared to a native control higher order (oligomeric) antigen. Reduced binding includes no detectable binding (the epitope is occluded in the assembled antigen and fails to bind to a non-neutralizing antibody while the epitope is not occluded in the native control antigen which binds the non-neutralizing antibody). In particular, the epitope recognised by antibody CBH4G is occluded in assembled E2 as described herein.

In another embodiment the present disclosure enables a composition comprising a higher order extracellularly assembled HCV E2 glycoprotein antigen, wherein the assembled E2 displays reduced binding to the non-neutralizing antibody. In particular, non-neutralizing antibody CBH4G displayed reduced binding to assembled E2 compared to a native control oligomeric HCV E2. This antibody is described in the literature, for example, in Keck et al. *PLos Pathogens:* 8 (4) e1002653, April 2012. Also, antibody 2A12 displayed reduced binding to assembled E2 relative to a native control oligomeric HCV E2. Antibody panels and how to generate them are described in Vietheer et al. *Hepatology:* 65 (4), 1117-1131, 2017 incorporated herein by reference, and references referred to therein such as references 5, 33-36, 17 and 37 and supplemental materials available from the publisher.

Thus, in one embodiment the assembled antigen has reduced exposed epitope and/or epitope residues bound by antibody 2A12 or antibody CBH4G or is not recognised by non-neutralizing antibodies, such as antibody 2A12 or antibody CBH4G known in the art.

In another embodiment the present disclosure enables a composition comprising a higher order extracellularly assembled higher order viral envelope antigen, wherein the assembled viral env antigen displays reduced binding to the non-neutralizing antibody compared to a native control higher order viral envelope antigen.

In an embodiment, the refolded oligomeric antigen displays at least one characteristic selected from the group consisting of:
(i) reduced binding to non-neutralizing antibodies relative to a control native antigen form or monomeric form:
(ii) at least substantially the same binding to neutralizing antibodies relative to a control native antigen form;
(iii) elicits the production of lower titres of non-neutralizing antibodies relative to a control native antigen form or monomeric antigen;
(iv) elicits the production of neutralizing antibodies;
(v) elicits the production of broadly neutralizing antibodies;
(vi) optionally elicits the production of higher titres of neutralizing antibodies; and
(vii) optionally elicits the production of higher titres of broadly neutralizing antibodies.

In another embodiment the present disclosure enables a composition comprising a higher order extracellularly assembled higher order HIV envelope antigen, wherein the assembled HIV env antigen displays reduced binding to the non-neutralizing antibody compared to a native control higher order HIV envelope antigen.

Suitable controls will be well understood by the skilled addressee in the context of the present disclosure. In one embodiment, the control antigen is the same genotype as the test antigen of interest, produced recombinantly in a host cell, such as a bacterial or a mammalian, yeast, plant or insect cell.

In one embodiment, the assembled higher order antigen is the receptor-binding domain (RBD) of HCV E2.

In one embodiment, the HCV E2 antigen lacks all or part of a hypervariable region such as one or more of hypervariable region 1 (HVR1) or a part thereof, the hypervariable region 2 (HVR2) or a part thereof and/or the intergenotypic variable region (igVR/VR3) or a part thereof. Examples of HVR1, HVR2 and igVR/VR3 sequences are shown in FIG. 12.

In some embodiments, the E2 antigen comprises a non-cysteine substitution or mutation in one or more of amino acid residues selected from the group comprising: C581, C585, C652, C677, C494, C486, C459, C452, C564, C597, and C569. In one embodiment, reference to one or more amino acids in this context means 2, 3, 4, 5, 6, or 7 amino acids are non-cysteine substitutions or are deleted or otherwise mutated.

In one embodiment the present disclosure provides a composition comprising assembled higher order HCV E2 antigen (assembled from monomeric E2) and a pharmaceutically or physiologically acceptable carrier and/or diluent.

In one embodiment, the composition comprises a pharmaceutically or physiologically acceptable diluent, carrier or adjuvant. In one embodiment, antigens may be presented in any form of carrier suitable for a vaccine composition.

In one embodiment, the disclosure provides for the use of the composition as described herein in the preparation of a medicament for the treatment or prevention of a viral infection such HCV or HIV infection, or cancer, or a condition associated with a viral envelope or cancer antigen.

In one embodiment, the disclosure provides for the use of the assembled higher order antigen, or composition in the preparation of a diagnostic agent for the diagnosis or monitoring of a condition associated with the antigen such as for E2, HCV infection or monitoring of an anti-HCV treatment protocol.

In one embodiment, the disclosure provides for a method for eliciting an immune response in a subject or patient, the method comprising administering to the subject or patient an effective amount of the herein described assembled higher order antigen, or the composition as herein described for a time and under conditions sufficient to elicit an immune response.

In one embodiment, the disclosure provides for a method for immunizing a subject against infection from HCV, comprising administering to the subject the assembled oligomeric antigen, or the composition as described herein.

In one embodiment, the disclosure provides for a method for treating or preventing HCV infection in a subject, comprising administering to the subject the assembled oligomeric antigen, or the composition as described for a time and under conditions sufficient to treat or prevent HCV infection.

In one embodiment, the composition further comprises a second higher order antigen from a different pathogen.

In one embodiment, the assembled higher order antigen comprises a detectable or purification tag.

In one embodiment, the disclosure provides for producing a purified antibody against the higher order assembled antigen as described herein, comprising administering an effective amount of antigen to a subject and purifying the antibody produced.

In one embodiment there is provided an antibody that specifically recognises the assembled higher order antigen/E2 antigen as described herein. Alternatively or in addition, antibodies can be identified that recognise an epitope exposed on native not assembled antigen, or assembled and not native antigen.

In one embodiment there is provided a kit, or a solid or semi-solid substrate, comprising the assembled higher order antigen as described herein, or the composition as described herein.

In one embodiment, the disclosure provides for the use of the assembled higher order antigen produced from a lower order antigen by the herein disclosed method comprising the following steps: (i) contacting a lower order antigen with a solution comprising a reducing agent for a time and under conditions sufficient to reduce one or more native cysteines; and (ii) removing or diluting the reducing agent or contacting the reduced lower order antigen with an oxidising agent, to elicit assembly of lower order antigen from (i) into an assembled higher order antigen, or the composition comprising a higher order extracellularly assembled higher order cancer antigen or viral envelope antigen, wherein the assembled viral env antigen displays reduced binding to the non-neutralizing antibody compared to a native control higher order viral envelope antigen, to bind to/detect an antigen specific immune cell.

In one embodiment, the subject higher order assembled antigens are suitable for or when used for the detection and/or isolation of an immune cell such as a B-cell specific for the antigen. In an embodiment, the immune cell is a T-cell specific for an antigen.

In another embodiment, the disclosure enables a method for detection and/or isolation of an immune cell/B-cell specific for an antigen comprising: i) labelling an immune cell/B-cell specific for an antigen with the assembled higher order antigen as described herein and ii) detecting and/or isolating the labelled immune cell/B-cell cytometrically.

In another embodiment, the disclosure enables a method for detection and/or isolation of an immune cell/B-cell specific for antigen such as HCV or HIV comprising: i) labelling an immune cell/B-cell specific for antigen such as HCV or HIV with the assembled higher order for of the antigen; and ii) detecting and/or isolating the labelled immune cell/B-cell cytometrically.

This summary is not an exhaustive recitation of all embodiments described in the specification.

BRIEF DESCRIPTION OF THE FIGURES

Some figures contain colour representations or entities. Coloured versions of the figures are available from the patentee upon request or from an appropriate Patent Office. A fee may be imposed if obtained from a Patent Office.

FIG. 1 shows agarose gel electrophoresis of Δ123-containing plasmids. Top row of bands represent the vector backbones and bottom row of bands represent the Δ123 inserts, which were isolated from the vector by digesting with restriction enzymes. pcDNA-H77cΔ123-HIS and pcDNA-S52Δ123-HIS were both digested with NheI and XbaI, while pcDNA-Con1Δ123-HIS was digested with NheI and XhoI. Expected lengths of the inserts released from H77c, Con1 and S52 Δ123-containing plasmids are 762 bp, 759 and 710 bp, respectively. GeneRuler 1 kb DNA ladder was used as a size marker (M).

FIG. 2 shows transfection and purification of Δ123. (A-B) Protein expression from transient transfections of pcDNA-Con1Δ123-HIS (A) and pcDNA-S52Δ123-HIS (B) into FS293F cells analysed via sandwich ELISA. Cell culture supernatants harvested on days 3, 5, 7 and 9 post-transfection were diluted by a factor of 2 before half-logarithmic serial dilutions of these were applied to dimeric MBP-CD81-LEL$^{113-201}$_coated enzyme immunoassay plates. Half-logarithmic serial dilutions of monomeric H77c Δ123 (1 μg/mL) and cell culture supernatant containing HIV gp140, which lacks a 6xHIS tag, were also included as positive and negative controls, respectively. This was followed by the addition of rabbit anti-HIS antibodies diluted to 1/1000 and detection with a single dilution of HRP-conjugated goat anti-rabbit immunoglobulins diluted to 1/1000. (C-D) Con1 Δ123 (C) and S52 Δ123 (D) after affinity chromatography analysed via sandwich ELISA conducted in the same way. Proteins contained in cell culture supernatants were applied to cobalt-charged TALON beads to allow binding of the 6xHIS tagged Δ123, and the supernatant after TALON interaction was collected as the flow through. Proteins were then washed and eluted into three separate fractions. All samples were diluted as appropriate to equalise their amounts for ELISA relative to the original preparation.

FIG. 3 shows gel filtration profiles of Δ123. (A) Affinity-purified H77c Δ123 glycoproteins produced from stable transfection in FS293F cells and analysed by gel filtration chromatography using Superdex 200. Dotted lines and peak heights indicate the fractions that correspond to monomers (78), dimers (70), HMW2 (59) and HMW1 (46) Δ123. (B-C) shows gel filtration chromatography using Superdex200 of affinity-purified Con1 Δ123 (B) and S52 Δ123 (C) produced from round 1 of transient transfections into FS293F cells. Dotted lines and peak heights indicate the fractions that correspond to monomers, dimers, HMW2 and HMW1, respectively, labelled by the numbers 77, 68, 66, 46 and 78, 69, 65, 46 for Con1 and S52, respectively. (D-E) show transient transfections of Con1 Δ123 (D) and S52 Δ123 (E) into FS293F cells were repeated (i.e. round 2) and Δ123 glycoproteins produced were affinity-purified before subjected to analysis by gel filtration chromatography in the same way as round 1.

FIG. 4 shows gel filtration of fractionated Δ123 analysed via SDS-PAGE. Non-reducing SDS-PAGE and coomassie staining of gel filtration fractionated (A) Con1 Δ123 (B) and S52 Δ123, with 20 uL from each of two consecutive fractions pooled and loaded onto a 5-12% polyacrylamide gradient gel. Reducing SDS-PAGE and Coomassie staining of gel filtration fractionated (C) Con1 Δ123 and (D) S52 Δ123, with the same volumes as non-reducing SDS-PAGE loaded onto a 12% acrylamide gel. Bio-Rad broad-range SDS-PAGE standards were loaded as markers (M).

FIG. 5 (A) shows an example of the ability of a MAb to bind monomeric and HMW1 Δ123. Monomeric Δ123 (red) (2 μg/mL) and HMW1 Δ123 (blue) (5 μg/mL) and BSA (green) as a negative control were coated onto enzyme immunoassay plates. Half-logarithmic serial dilutions of the primary antibody was then added and binding was detected with the appropriate HRP-conjugated secondary antibody. Using this technique, the relative binding of a panel MAb towards HMW1 Δ123 were then calculated by comparing the mid-point of each binding curve, which was taken as half of the highest optical density value. The fold difference in binding was calculated relative to monomer and H77c HMW1 Δ123 for construction of Table 7. (B) shows the reactivity of different strains of Δ123 to a panel of MAbs.

Single dilution point assessment was performed, whereby H77c, Con1 and S52 Δ123 monomers (5 μg/mL) were coated onto enzyme immunoassay plates as well as BSA (5 μg/mL) as a negative control. A single dilution of the primary antibodies was added and binding detected with the appropriate species specific HRP-conjugated secondary antibodies.

FIG. 6 (A) shows small scale Tris(2-carboxyethyl) phosphine hydrochloride (TCEP) reduction. H77 Δ123 monomers coated on an enzyme immunoassay plate were reduced with different concentrations of TCEP (0-500 mM) prepared in PBS pH 9.6 for 30 min at 37° C. A single dilution of the primary antibodies was added, including conformation-dependent mouse H53 (1 μg/mL) as well as rabbit anti-HIS (1/1000) and human anti-CMV R04 (1/1000), which represent positive and negative controls, respectively. Binding was detected with the appropriate HRP-conjugated secondary antibodies. Reactivity towards each of the primary antibodies was tested in triplicate, and the mean optical density values plotted as a line graph with error bars showing the standard deviations. (B) shows monomeric H77c Δ123 treated with TCEP and BMOE. Non-reducing SDS-PAGE and Coomassie staining of monomeric H77c Δ123 (10 μg) after TCEP reduction and refolding with BMOE crosslinkers under different conditions labelled 1-7, which are described in Table 8. Δ123 samples were loaded onto a 5-12% polyacrylamide gradient gel, along with monomeric and HMW1 H77c Δ123 (5 μg each) as controls as well as broad-range SDS-PAGE markers (M).

FIG. 7 (A) shows monomeric H77c Δ123 treated with glutathione. Non-reducing SDS-PAGE and coomassie staining of monomeric H77c Δ123 (10 μg) after refolding with GSH and GSSG using the redox-shuffling system under different conditions labelled 1-5, which are described in Table 9. H77c Δ123 samples were loaded onto a 5-12% polyacrylamide gradient gel, along with monomeric and HMW1 H77c Δ123 (5 μg each) as controls as well as broad-range SDS-PAGE markers (M). (B) shows gel filtration profiles of monomeric H77c Δ123 treated with glutathione. Gel filtration chromatography of untreated monomeric H77c Δ123 using Superdex 200. (C) shows gel filtration chromatography of H77c Δ123 after 10 μg/μL of the glycoprotein was treated with 2 mM GSH and 0.4 mM GSSG using Superdex 200. Dotted lines and peak heights indicate the fractions that correspond to monomers (78) and dimers (69).

FIG. 8 (A) shows small scale DTT reduction. H77c Δ123 monomers, coated on an enzyme immunoassay plate, were reduced with different concentrations of DTT (0-10 mM) prepared in carbonate-bicarbonate buffer pH 9.6 for 30 min at 37° C. A single dilution of the primary antibodies was added, including conformation-dependent mouse H53 (1 μg/mL) as well as rabbit anti-HIS (1/1000) and human anti-CMV R04, which represent positive and negative controls, respectively. Binding was detected with the appropriate HRP-conjugated secondary antibodies. Reactivity towards each of the primary antibodies was tested in triplicate, and the mean optical density values plotted as a line graph with error bars showing the standard deviations. (B) shows monomeric H77c Δ123 treated with DTT. Non-reducing SDS-PAGE and Coomassie staining of monomeric H77c Δ123 (10 μg) after DTT reduction under different conditions (labelled 1-12 and described in table 3.6) and refolding using the slow dilution method. H77c Δ123 samples were loaded onto a 5-12% polyacrylamide gradient gel, along with monomeric and HMW1 H77c Δ123 (5 μg each) as controls as well as broad-range SDS-PAGE markers (M). (C) shows gel filtration chromatography of untreated monomeric H77c Δ123 using Superdex 200. (D) shows gel filtration chromatography of H77c Δ123 after 1 μg/μL of the glycoprotein was treated with 1 mM DTT using Superdex 200. Dotted lines and peak heights indicate the fractions that correspond to monomers (77-78), dimers (69) and HMW Δ123 (59).

FIG. 9 shows the antigenic characterization of DTT-treated Δ123 and ALA7Δ123. DTT-treated Δ123 and ALA7Δ 123 has been characterized by assessment of binding with the antibodies (A) AR3C (B) CBH4G (C) HC84.27 and (D) HCV1 as described in Example 15.

FIG. 11 shows the analysis of products generated from refolding non-refolded Δ123 monomers and refolding of Δ123 in the presence of protease inhibitors using gel filtration chromatography as described in Example 14.

FIG. 12 provides a ClustalW alignment of the corresponding E2661 region of HCV isolates used. H77c (AF009606, G1a, SEQ ID NO: 11), J6 (AF177036, G2a, SEQ ID NO: 16), s52 (GU814263, G3a, SEQ ID NO: 13), ED43 (GU814265, G4a, SEQ ID NO: 10), SA13 (AF064490, G5a, SEQ ID NO: 12), EUHK2 (Y12083, G6a, SEQ ID NO: 14), QC69 (EF108306, G7a, SEQ ID NO: 15). HVR1, HVR2 and igVR/VR3 are shown in red/orange. Residues corresponding to amino acid residues GFLASLFY, YTWGENETD and YRLWHF of ED43 are CD81 binding regions.

FIG. 13 shows the nucleotide construct for: Δ123Ala7 codon optimized; Underlined regions correspond to restriction enzyme sites GGTACC=KpnI, GGATCC=BamHI, CTCGAG=XhoI and the protein sequence for Δ123Ala7.

FIG. 14 to FIG. 14*c* display a ClustalOmega amino acid alignment of the protein sequences: AF009606 coding sequence (SEQ ID NO:6), AF009606 Full length E2 (SEQ ID NO:7), AF009606 E2$_{661}$ (SEQ ID) NO: 8), WT_E2$_{661}$ (SEQ ID NO: 4) and Δ123 (SEQ ID NO: 3). The underlined region corresponds to residues 630-635.

FIG. 15 (A) shows non-reducing SDS-PAGE of samples reduced with different concentrations of β-mercaptoethanol and assembled. Precision size markers are shown on the left with molecular weights indicated in kDa. Indicative size of monomer, dimer and high molecular weight forms shown on right. (B) shows gel filtration chromatography of monomeric Δ123 after treatment with 100 mM BME (dashed line) or untreated (solid line) using Superdex 200.

Figure 16:
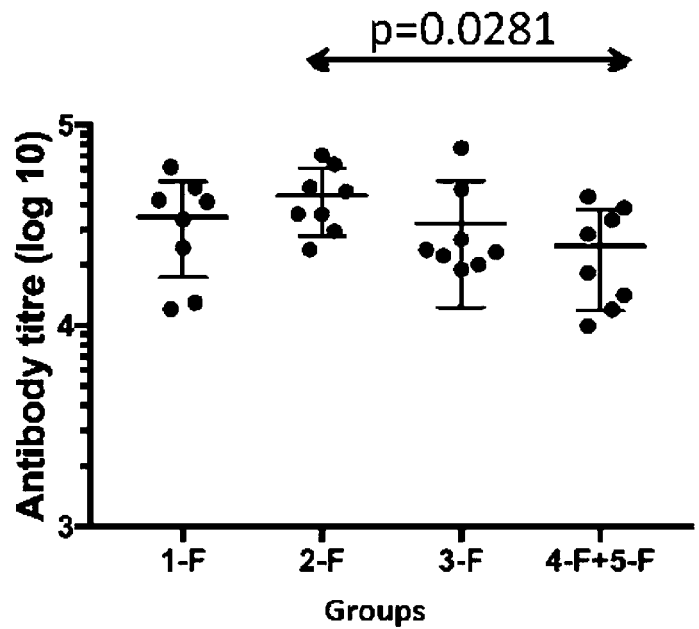

FIG. 16 shows antibody titres in animals vaccinated with assembled HCV proteins. Final bleeds from animals vaccinated with antigens listed in Table 15 were analysed for their ability to bind to monomeric Δ123 protein. Reciprocal antibody titres for each group are shown. Horizontal line is the mean, with upper and lower bars representing the standard deviation. The difference in antibody titre between 2-F and 4-F+5-F was statistically significant (p=0.0281) using a Mann-Whitney unpaired t-test. Prism v7.0.

Figure 17:
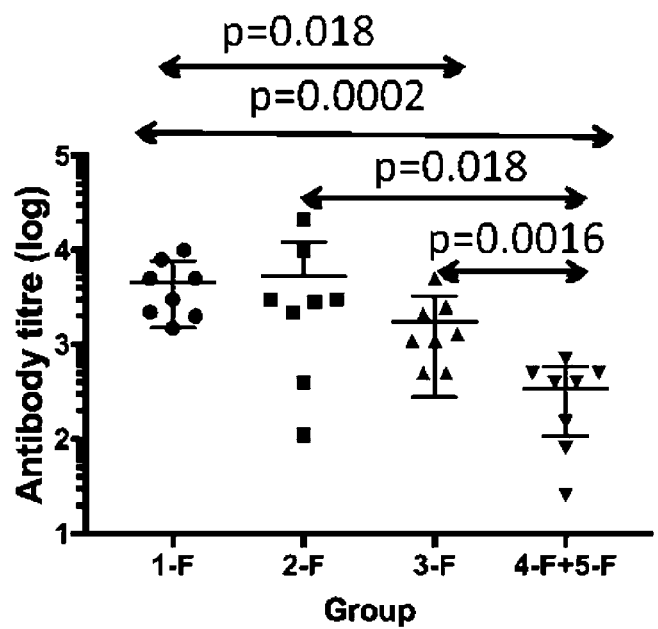

FIG. 17 shows antibody titres to epitope I in animals vaccinated with assembled HCV proteins. Final bleeds from animals vaccinated with antigens listed in Table 15 were analysed for their ability to bind to the synthetic peptide encompassing residues 409-428 of the Genotype 1a H77c sequence. Reciprocal antibody titres for each group are shown. Horizontal line is the mean, with upper and lower bars representing the standard deviation. Differences in antibody titres between groups was determined using a Mann-Whitney unpaired t-test. Prism v7.0.

Figure 18:
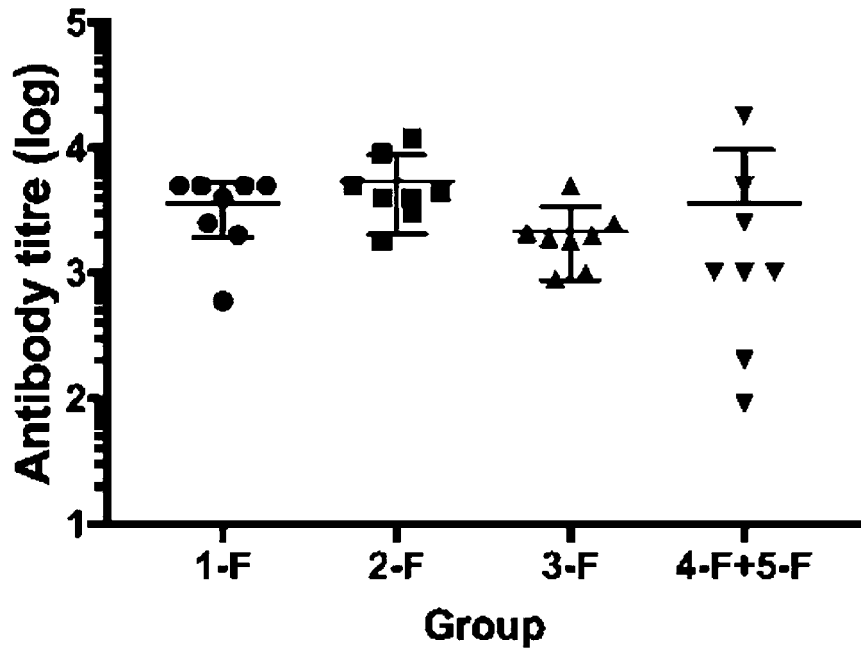

FIG. 18 shows antibody titres to epitope III in animals vaccinated with assembled HCV proteins. Final bleeds from animals vaccinated with antigens listed in Table 15 were analysed for their ability to bind to the synthetic peptide encompassing residues 523-549 of the Genotype 1a H77c sequence. Reciprocal antibody titres for each group are shown. Horizontal line is the mean, with upper and lower bars representing the standard deviation. Differences in antibody titres between groups was determined using a Mann-Whitney unpaired t-test. Prism v7.0.

Figure 19:
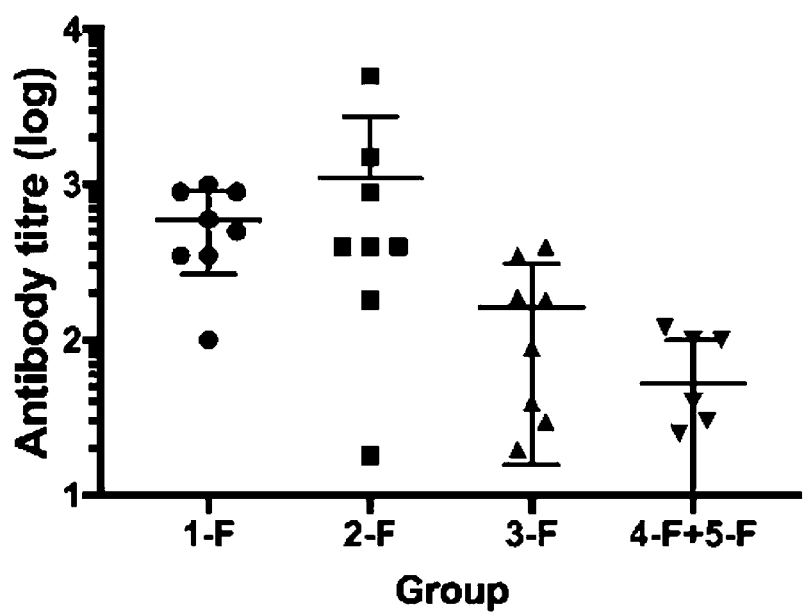

FIG. 19 shows antibody titres to genotype 2a epitope I in animals vaccinated with assembled HCV proteins. Final bleeds from animals vaccinated with antigens listed in Table 15 were analysed for their ability to bind to the synthetic peptide encompassing residues 409-428 of the Genotype 2a J6 sequence. Reciprocal antibody titres for each group are shown. Horizontal line is the mean, with upper and lower bars representing the standard deviation. Differences in antibody titres between groups was determined using a Mann-Whitney unpaired t-test. Prism v7.0.

FIG. 20 shows the ability of immune serum to inhibit interaction between HCV E2 and its cellular receptor CD81. Final bleeds from animals vaccinated with antigens listed in Table 15 were analysed for their ability to inhibit the binding between (A) H77c G1a E2 and CD81, and (B) J6 G2a E2 and CD81. Reciprocal antibody titres for each group are shown. Horizontal line is the mean, with upper and lower bars representing the standard deviation. Differences in antibody titres between groups was determined using a Mann-Whitney unpaired t-test. Prism v7.0.

Figure 21:
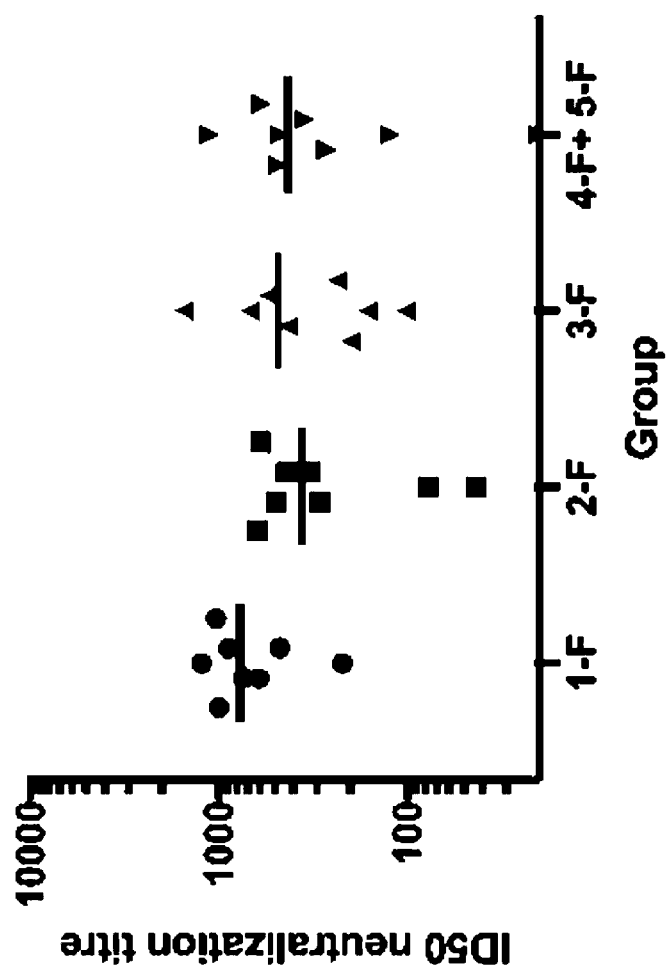

FIG. 21 shows the ability of immune serum to prevent infection of liver cells with genotype 1a viruses. Final bleeds from animals vaccinated with antigens listed in Table 15 were analysed for their ability to prevent infection with G1a HCVpp. Reciprocal antibody titres for each group are shown. Horizontal line is the mean.

Figure 22:
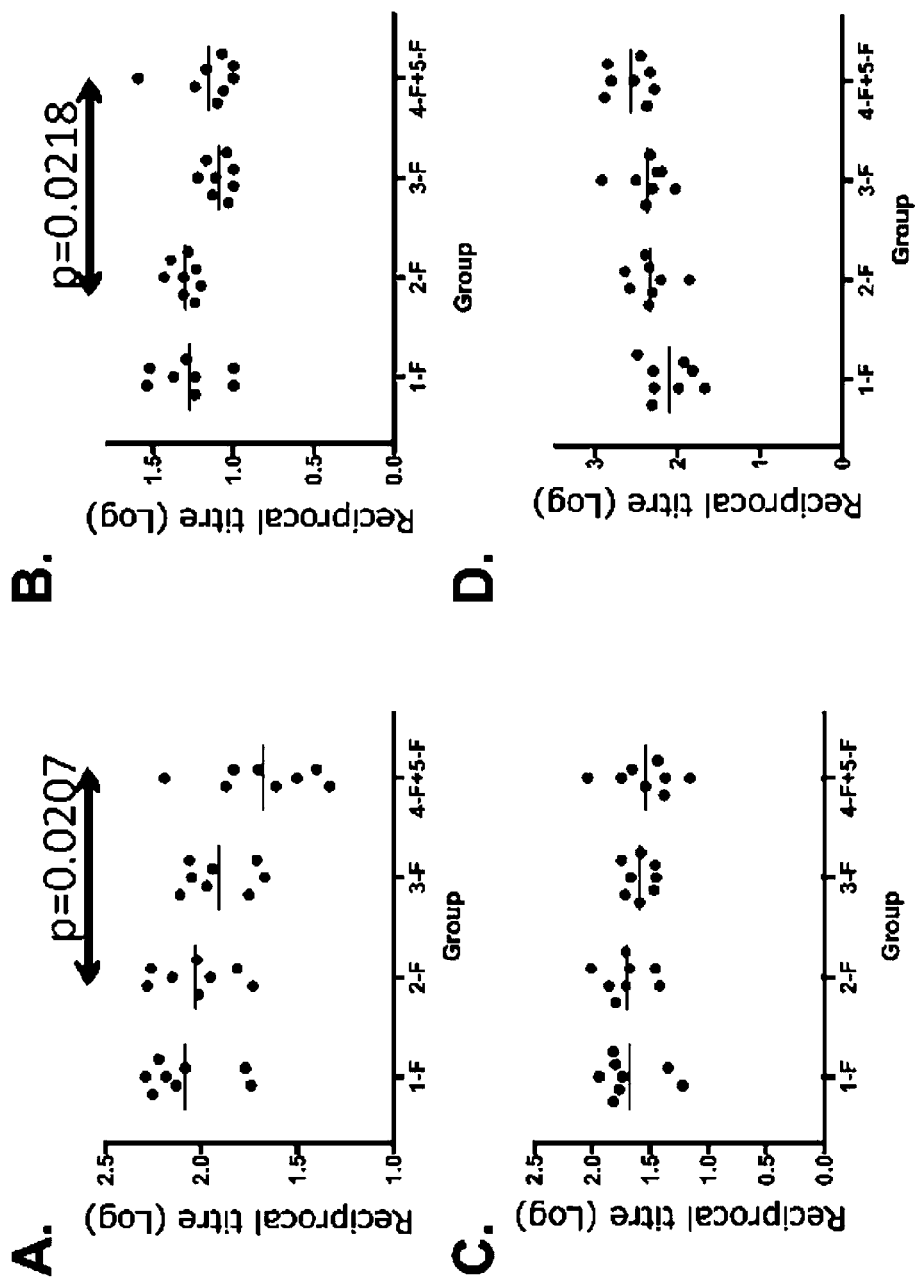

FIG. 22 shows the specificity of HMW1 and monomer immune sera. Serial dilutions of guinea pig sera were added to a constant amount of HCV1 (A), HC84-27 (B), AR3C (C) and 2A12 (D). Antibodies were added to monomeric Δ123 and bound MAb was detected with anti-Human Fab$_2$. Groups were compared using Mann-Whitney t test (Prism v 7).

Figure 23:
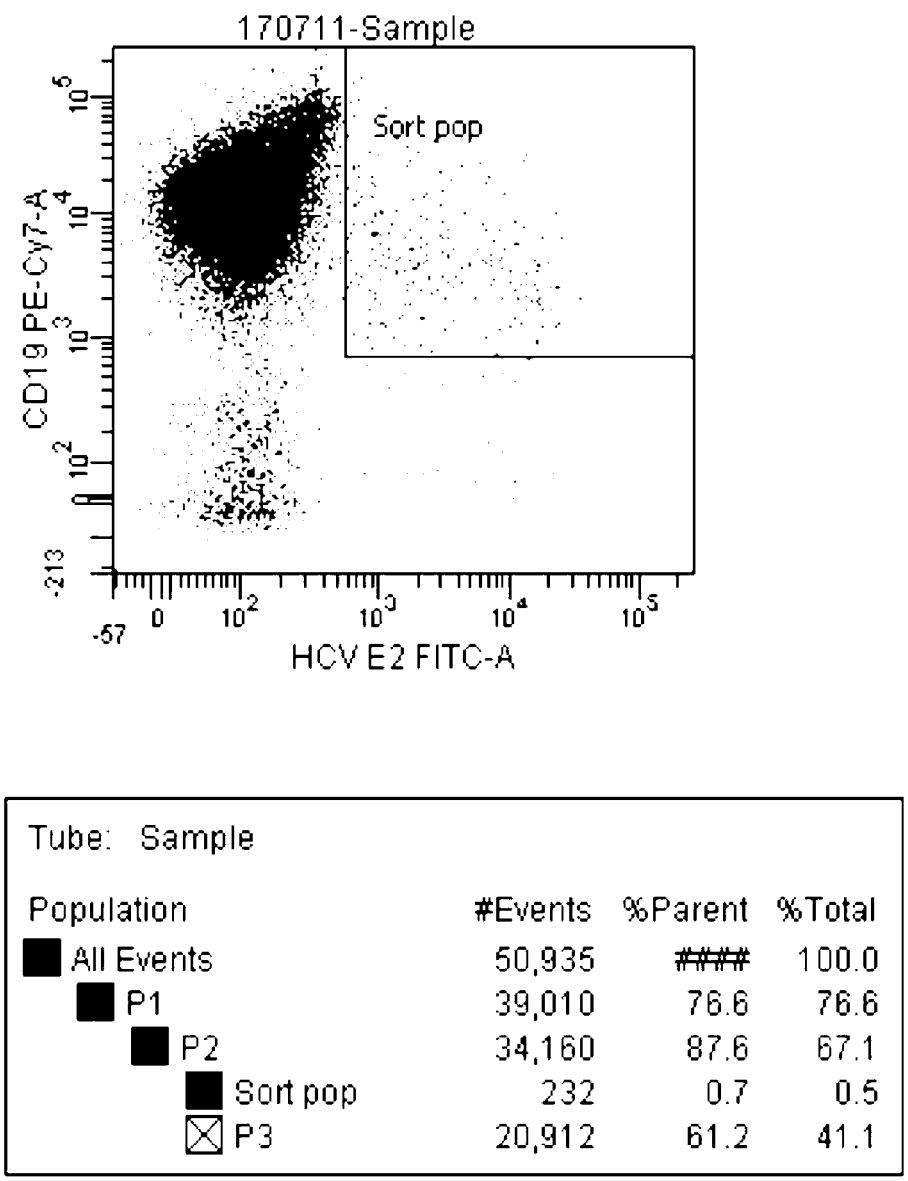

FIG. 23 shows a FACS plot of sorted B cell population using assembled Δ123. CD19 positive and anti-E2 positive B cells were detected with anti-CD19 Cy7 antibody and assembled Δ123.

Figure 24:
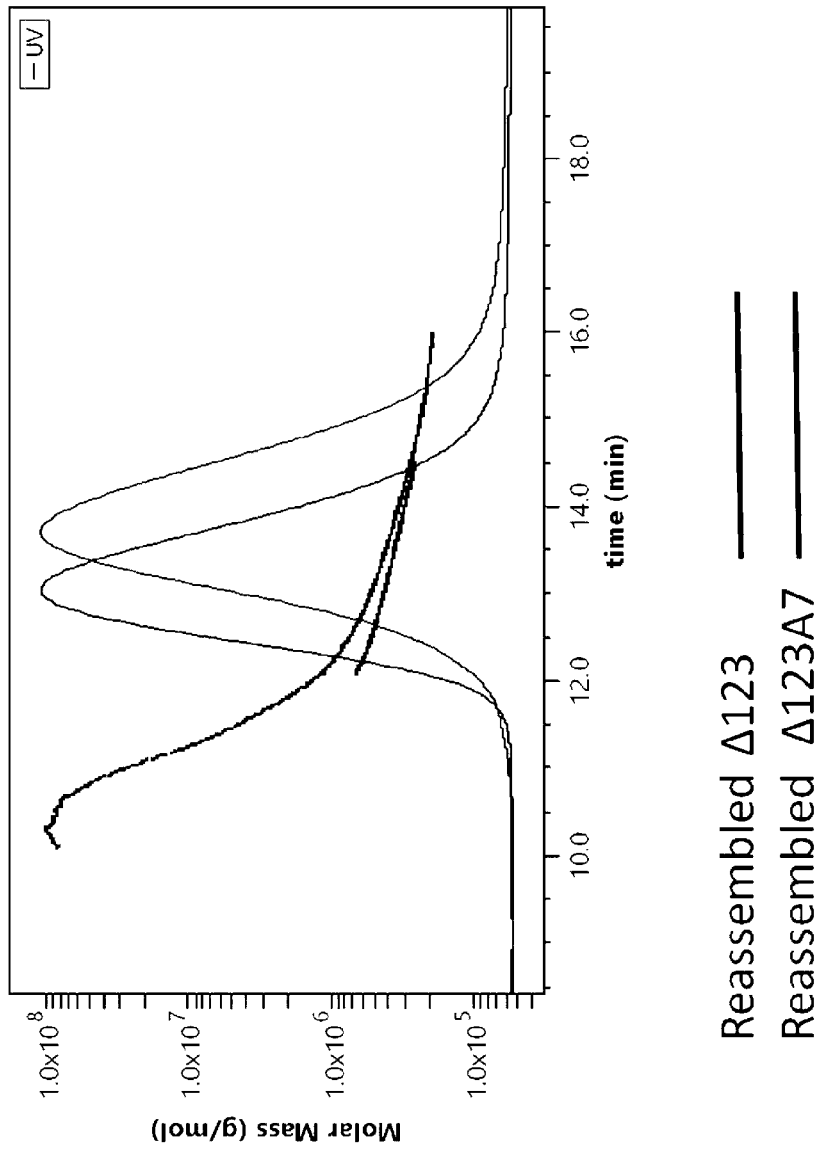

FIG. 24 shows size-exclusion chromatography-Multi angle light scattering to determine size of assembled proteins. Overlay of UV (A$_{280}$nm) signal and molar mass of assembled Δ123A7 (blue) and assembled Δ123 (red) samples.

Figure 25:
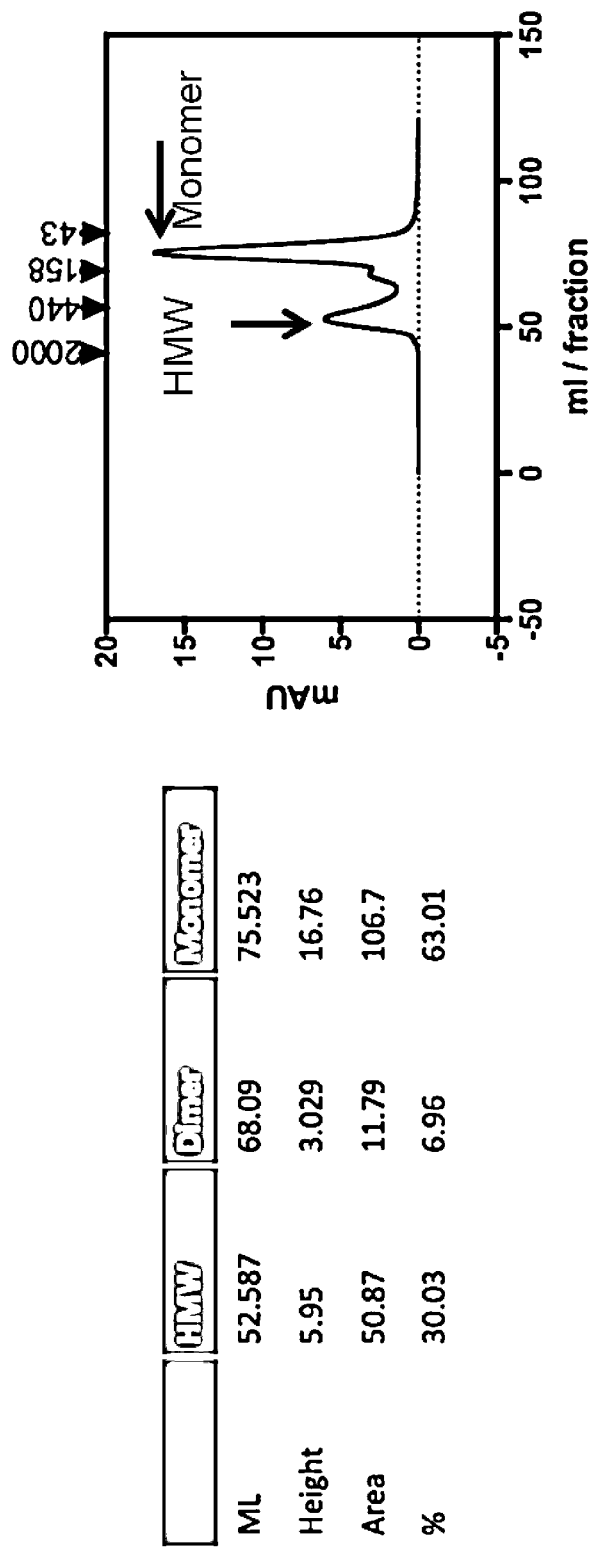

FIG. 25 shows size-exclusion chromatography of Δ123A7 monomers that were not assembled into HMW forms following treatment with DTT that were subjected to a second round of denaturation with DTT followed by assembly. The monomer and HMW species are indicated by arrows and the % of each shown in the table.

Figure 26:
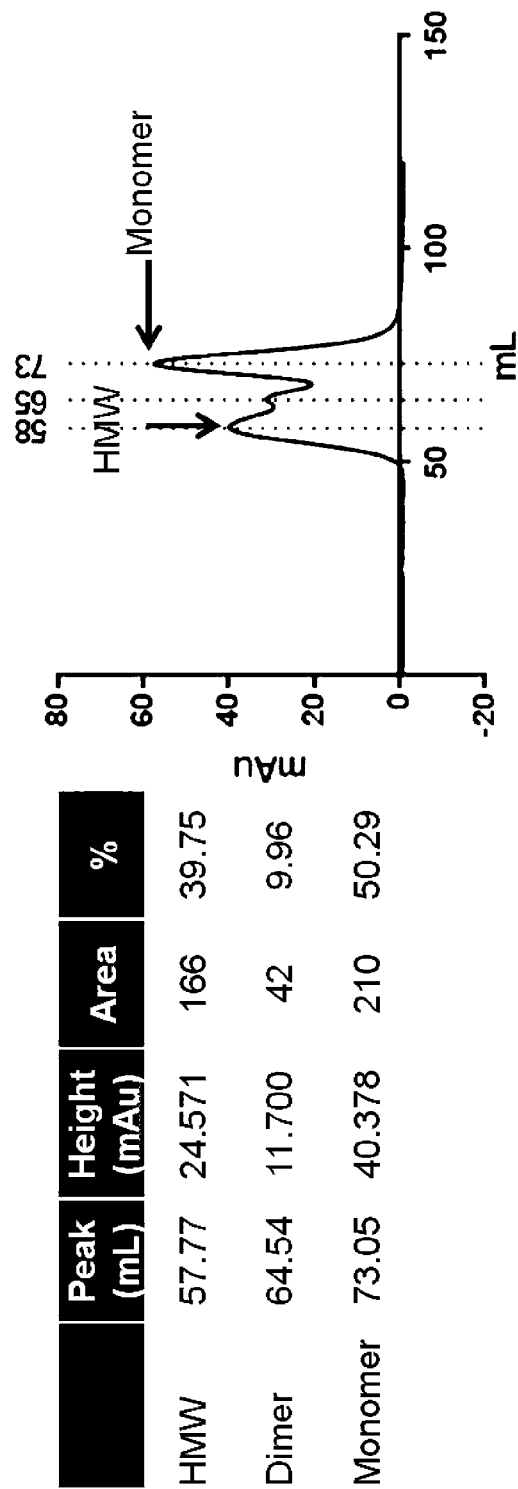

FIG. 26 shows size-exclusion chromatography of RBD monomers subjected to denaturation with DIT followed by assembly. The monomer and HMW species are indicated by arrows and the % of each shown in the table.

Figure 27:
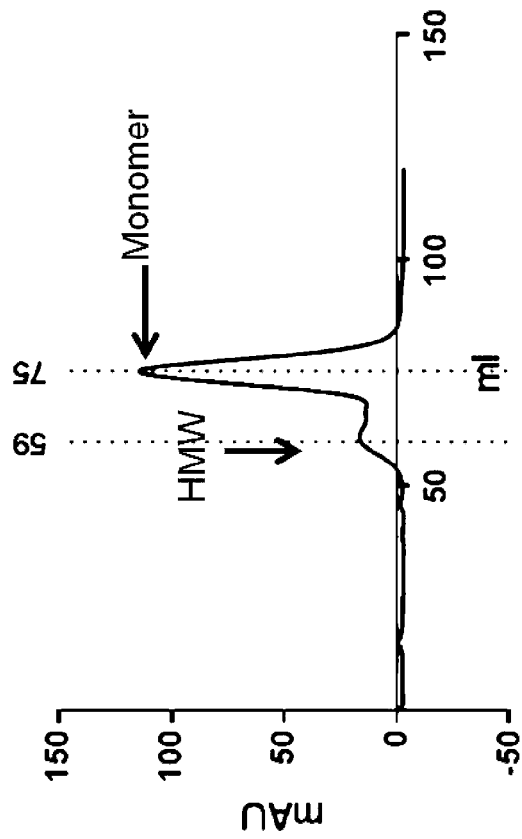

FIG. 27 shows size-exclusion chromatography of RBDΔ7 monomers subjected to denaturation with DTT followed by assembly. The monomer and HMW species are indicated by arrows and the % of each shown in the table.

Figure 28:
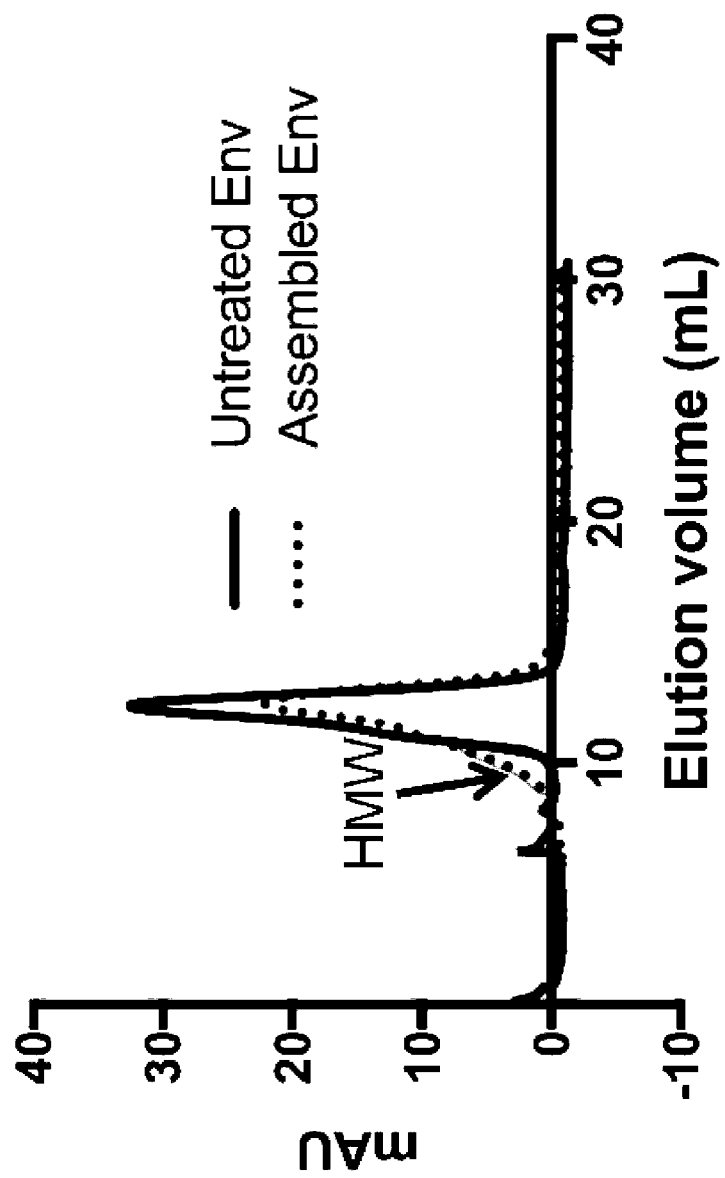

FIG. 28 shows size-exclusion chromatography of env monomers subjected to denaturation with DTT followed by assembly. The HMW species is indicated by an arrow.

BRIEF DESCRIPTION OF THE TABLES

Figure 7:
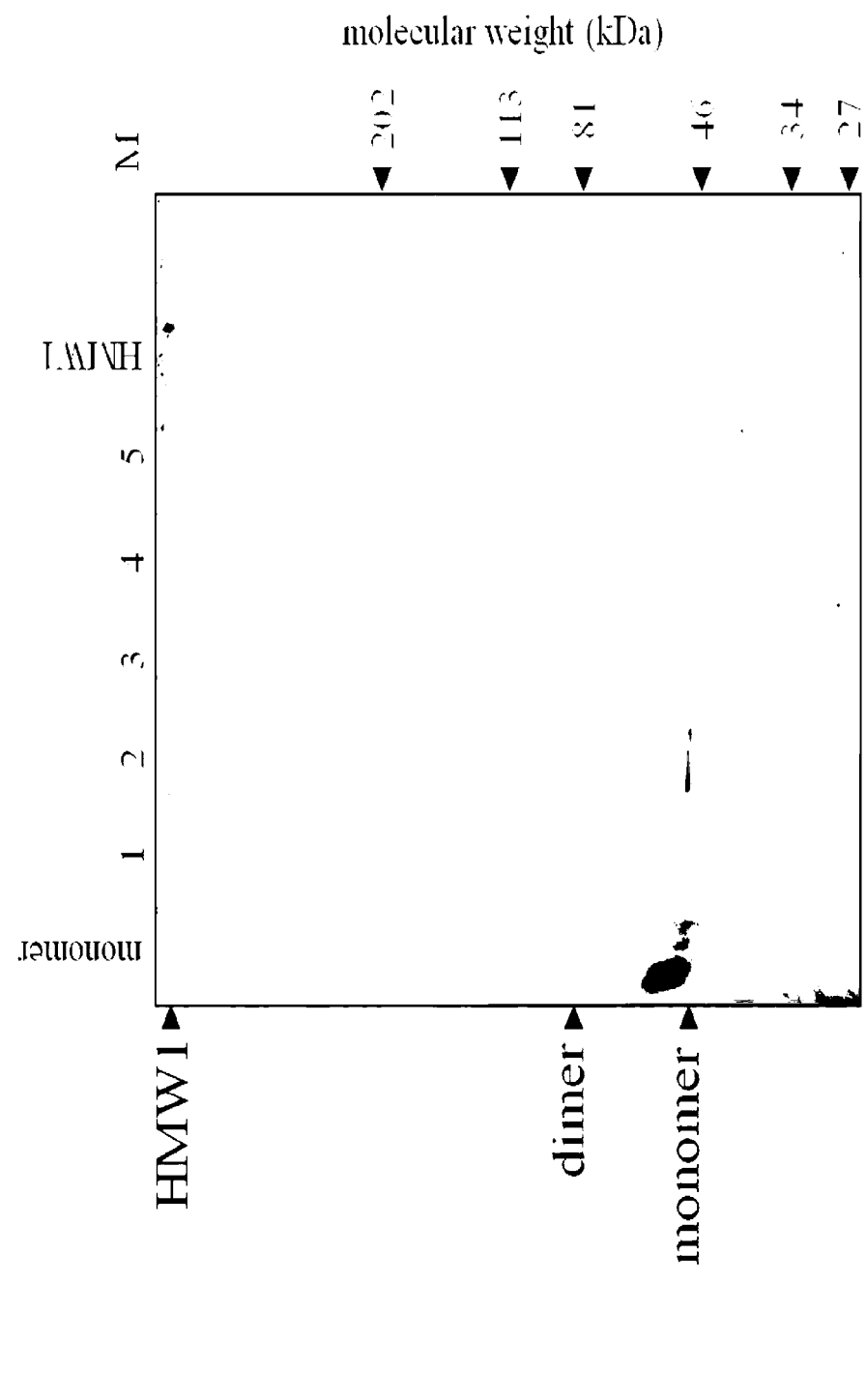

Table 1 shows the transient transfection conditions.
Table 2 shows a list of MAbs.
Table 3 shows the conditions for DIT reduction.
Table 4 shows the conditions for protein refolding with glutathione.
Table 5 shows the conditions for TCEP reduction.
Table 6 shows the expression of the different oligomeric forms of Δ123. Percentage of monomers, dimers, HMW2 and HMW1 were calculated by dividing the area under their corresponding peak on the gel filtration curves (FIG. 3B-E) by the total area under the curve. Area under the curve was quantified using the UNICORN control software by GE Healthcare Life Sciences.
Table 7 shows the antigenic characterisation of HMW1 Δ123.
Table 8 shows the conditions for TCEP reduction and BMOE-mediated refolding of Δ123.
Table 9 shows the conditions for H77c Δ123 refolding with glutathione. The ratio of monomers vs. dimers was calculated by dividing the densitometry of monomers by the densitometry of dimers from non-reducing SDS-PAGE analysis of glutathione treated H77c Δ123 (FIG. 7A). Densitometry was quantified using the LI-COR Odyssey system.
Table 10 shows the quantification of multimer formation from glutathione-treated monomeric H77c Δ123. Area under the monomer and dimer peaks on the gel filtration curves (FIG. 7B) calculated as a percentage of the total area under the curve, and ratio of monomers vs. multimers calculated by dividing the area under the monomer peak by that of the dimer peak.
Table 11 shows the quantification of multimer formation from DTT-treated monomeric H77c Δ123. Area under the monomer and HMW peaks on the gel filtration curves (FIG. 7C-D) calculated as a percentage of the total area under the curve, and ratio of monomers (76 min) vs. multimers (58 min) calculated by dividing the area under the monomer peak by that of multimer peak peak.
Table 12 shows the quantification of multimer formation from DTT-treated monomeric H77c Δ123. Area under the monomer and multimer peaks on the gel filtration curves (FIG. 7B) calculated as a percentage of the total area under the curve, and ratio of monomers vs. multimers calculated by dividing the area under the monomer peak by that of the multimer peak.
Table 13 shows the methods which generated refolding protein using the antigen Δ123.
Table 14 shows the % refolding protein generated by differing refolding methods.
Table 15 shows the immunization groups.
Table 16 shows the statistical analysis of immune sera reactivity to monomeric Δ123.
Table 17 shows the statistical analysis of the ability of immune serum to bind to H77c epitope I.
Table 18 shows the statistical analysis of the ability of immune serum to bind to H77c epitope III.
Table 19 shows the statistical analysis of the ability of immune serum to bind to J6 epitope I.
Table 20 shows the statistical analysis of the ability of immune serum to block H77c G1a E2 binding to CD81.

Table 21 shows the statistical analysis of the ability of immune serum to block JFH-1 G2a E2 binding to CD81.

Table 22 shows the statistical analysis of the ability of immune serum to prevent H77c HCV viruses infecting liver cells.

Table 23 shows the statistical analysis of the ability of immune serum to prevent binding of HCV1.

Table 24 shows the statistical analysis of the ability of immune serum to prevent binding of HC84-27.

Table 25 shows the statistical analysis of the ability of immune serum to prevent binding of AR3C.

Table 26 shows the statistical analysis of the ability of immune serum to prevent binding of 2A12.

Table 27 shows the SEC-MALS of reassembled proteins.

KEY TO SEQUENCE LISTING

SEQ ID NO: 1: DNA construct for codon optimised Δ123Ala7.

SEQ ID NO: 2: DNA sequence encoding codon optimised Δ123Ala7.

SEQ ID NO: 3: Amino acid sequence Δ123Ala7.

SEQ ID NO: 4: Amino acid sequence encoding WT $E2_{661}$ (RBD).

SEQ ID NO: 5: $\Delta 123\ E2_{661}$.

SEQ ID NO: 6: Amino acid residues corresponding to the AF009606 coding sequence.

SEQ ID NO: 7: Amino acid residues corresponding to AF009606 full length E2 protein sequence.

SEQ ID NO: 8: Amino acid residues corresponding to AF009606 $E2_{661}$.

SEQ ID NO: 9: N-Terminal signal sequence.

SEQ ID NO: 10: Amino acid sequence ED43.

SEQ ID NO: 11: Amino acid sequence H77c.

SEQ ID NO: 12: Amino acid sequence SA13.

SEQ ID NO: 13: Amino acid sequence s52.

SEQ ID NO: 14: Amino acid sequence EUHK2.

SEQ ID NO: 15: Amino acid sequence QC69.

SEQ ID NO: 16: Amino acid sequence J6.

SEQ ID NO: 17: Amino acid residues corresponding to HIV env lacking the C-terminal transmembrane domain and cytoplasmic tail.

SEQ ID NO: 18: Amino acid residues corresponding to HIV env with an N-terminal leader sequence.

SEQ ID NO: 19: DNA sequence encoding codon H77cΔ123.

SEQ ID NO: 20: DNA sequence encoding Con1Δ123.

SEQ ID NO: 21: DNA sequence encoding s52Δ123.

SEQ ID NO: 22: Human trypsinogen signal peptide.

SEQ ID NO: 23: Human tissue plasminogen activator signal peptide (tPA).

SEQ ID NO: 24: Six His tag.

DETAILED DISCUSSION OF EMBODIMENTS

The subject disclosure is not limited to particular screening procedures for agents, specific formulations of agents and various medical methodologies, as such may vary.

Each embodiment in this specification is to be applied mutatis mutandis to every other embodiment unless expressly stated otherwise.

Unless defined otherwise, all technical and scientific terms used herein have the same meanings as commonly understood by one of ordinary skill in the art to which this invention belongs. Any materials and methods similar or equivalent to those described herein can be used to practice or test the present invention. Practitioners are particularly directed to Sambrook et al., 1989 (supra), Coligan et al. Current Protocols In Protein Science, John Wiley & Sons, Inc., 1995-1997, in particular Chapters 1, 5 and 6, and Ausubel et al., Current Protocols in Molecular Biology, Supplement 47, John Wiley & Sons, New York, 1999; Colowick and Kaplan, eds., Methods In Enzymology, Academic Press, Inc.; Weir and Blackwell, eds., Handbook of Experimental Immunology, Vols. I-IV, Blackwell Scientific Publications, 1986; Joklik ed., Virology, 3rd Edition, 1988; Fields and Knipe, eds, Fundamental Virology, 2nd Edition, 1991; Fields et al., eds, Virology, 3rd Edition, Lippincott-Raven, Philadelphia, Pa., 1996, for definitions and terms of the art and other methods known to the person skilled in the art. Reference may also be made to Staby, Rathore and Ahuga, eds Preparative Chromatography for Separation of Proteins; Whiley, 2017, in particular Chapters 3 and 7. Also, Wen, Ellis, Pujar, eds, Vaccine Development and Manufacturing, Wiley, 2014, in particular Chapters 4, 6, 8, 11. Reference may also be made to WO2008022401, WO2012016290 and WO2012068637 for methods and materials.

Definitions

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements.

As used herein the singular forms "a", "an" and "the" include plural aspects unless the context clearly dictates otherwise. Thus, for example, reference to "a composition" includes a single composition, as well as two or more compositions; reference to "an agent" includes one agent, as well as two or more agents; reference to "the disclosure" includes single and multiple aspects of the disclosure and so forth.

While the examples illustrate the assembly of oligomeric HCV E2 from monomeric HCV E2 and the assembly of oligomeric HIV env from monomeric HIV env, the present disclosure is not limited to these particular examples and extends to the assembly of viral envelope proteins and cancer antigens for vaccine production or in ex vivo binding applications. In this respect, the method provides for the production of higher order antigens from lower order antigens. Reference to "higher order" antigens means trimers or larger multiples, while "lower order forms" means monomers or dimers. The terms "antigen" "species" and "form" are used interchangeably.

Reference to "native" means the antigen has been assembled using cellular machinery within a cell. The terms "assembled" and "folded" or "refolded" are used interchangeably although "assembled" is used to convey the partial de novo nature of the assembled antigen. Reference to assembled means "cell-free" assembled. In one embodiment, assembled antigens are as effective or more effective immuonogens than their native counterparts.

As used herein "non-neutralizing antibodies" refers to antibodies that bind to a viral antigen but do not decrease or disrupt viral entry. In one embodiment, in it refers to antibodies that bind to E2 but do not decrease or disrupt viral entry. In relation to cancer antigens, reference to non-neutralizing antibodies means antibodies that do not mediate tumor cell killing.

As used herein "neutralizing antibodies" refers to antibodies that bind to the viral antigen and when bound inhibits viral entry. In one embodiment, it refers to antibodies that bind to E2 and when bound to E2 inhibits viral entry. In relation to cancer antigens, reference to neutralizing antibodies means antibodies that directly or indirectly mediate tumor cell killing.

As used herein "broadly neutralizing antibodies" refers to antibodies that provide cross protection against multiple genotypes or subtypes of an antigen/HCV antigen.

Higher order or oligomeric forms are structural forms of the antigen including trimers and greater fold forms. Higher order antigens or forms or species are assembled from lower order forms, antigens or species. Lower order forms include monomeric or dimeric forms of the antigen.

Reference to a "control" will be understood by the skilled person and means employing a comparator or comparators that will generate or is likely to generate meaningful results in the context of the invention. Typically, a control is a counterpart produced in a host cell or cell free expression system.

Any viral envelope antigen may be engineered using the methods described in this specification. Non-limiting examples of viral families include Adenoviridae, African swine fever-like viruses, Arenaviridae, Arterivirus, Astroviridae, Buculoviridae, Birnaviridae, Bunyaviridae, Caliciviridae, Circoviridae, Coronaviridae, Deltavirus, Filoviridae, Flaviviridae, Hepadnaviridae, Hepeviridae, Herpesviridae, Orthomyxoviridae, Paramyxoviridae, Picornaviridae, Poxyviridae, Reoviridae, Retroviridae and Rhabdoviridae. Particular virus envelope antigens are from Paramyxoviridae, Retroviridae and Filoviridae.

Non-limiting examples of viral envelope antigens are derived from pathogenic viruses such as influenza haemagglutinin (HA); a lentivirus, such as HIV-1 glycoprotein (gp) 120 including the R2 subtype or HIV-2 gp125; a coronavirus, such as SARS Si glycoprotein; a paramyxovirus, such as respiratory syncytial virus (RSV) F2; or a flavivirus, such as Dengue virus E protein.

One important group of antigens are derived from pathogens such as the primary systemic fungal pathogens of man such *Coccidioides immitis, Histoplasma capsulatum, Blastomyces dermatitidis*, and *Paracoccidioides brasiliensis*. Important opportunistic fungal pathogens which tend to rely upon an immunocompromised host include *Cryptococcus neoformans, Pneumocystis jiroveci, Candida* spp., *Aspergillus* spp., *Penicillium marneffei*, and *Zygomycetes, Trichosporon beigelii*, and *Fusarium* spp. A range of pathogenic fungi are associated with immunocompromised subjects including those with AIDS, with chemotherapy induced neutropenia or patients undergoing haematopoietic stem cell transplantation, among others.

In some embodiments, the antigen is derived from a microbe including a bacterium, fungus, virus, algae, parasite, (including ecto-or endo-parasites) prion, oomycetes, slime, moulds, nematode, mycoplasma and the like. By way of non-limiting example, the microbe is selected from one or more of the following orders, genera or species: *Acinetobacter, Actinobacillus, Actinomycetes, Actinomyces, Aeromonas, Bacillus, Bacteroides, Bordetella, Borrelia, Brucella, Burkholderia, Campylobacter, Citrobacter, Clostridium, Corynebacterium, Enterobacter, Enterococcus, Erysipelothrix, Escherichia, Francisella, Haemophilus, Helicobacter, Klebsiella, Legionella, Leptospira, Listeria, Micrococcus, Moraxella, Morganella, Mycobacterium* (tuberculosis), *Nocardia, Neisseria, Pasteurella, Plesiomonas, Propionibacterium, Proteus, Providencia, Pseudomonas, Rhodococcus, Salmonella, Serratia, Shigella, Staphylococcus, Stenotrophomonas, Streptococcus, Treponema, Vibrio* (cholera) and *Yersinia* (plague), Adenoviridae, African swine fever-like viruses, Arenaviridae (such as viral haemorrhagic fevers, Lassa fever), Astroviridae (astroviruses) Bunyaviridae (La Crosse), Calicivirid (Norovirus), Coronaviridae (Corona virus), Filoviridae (such as Ebola virus, Marburg virus), Parvoviridae (B19 virus), Flaviviridae (such as hepatitis C virus, Dengue viruses), Hepadnaviridae (such as hepatitis B virus, Deltavirus), Herpesviridae (herpes simplex virus, varicella zoster virus), Orthomyxoviridae (influenza virus) Pupovaviridae (papilloma virus) Paramyxoviridae (such as human parainfluenza viruses, mumps virus, measles virus, human respiratory syncytial virus, Picornaviridae (common cold virus), Poxyiridae (small pox virus, orf virus, monkey poxvirus), Reoviridae (rotavirus), Retroviridae (human immunodeficiency virus), Paroviridae (paroviruses), Papillomaviridae, (papillomaviruses), alphaviruses, Rhabdoviridae (rabies virus), *Trypanosoma, Leishmania, Giardia, Trichomonas, Entamoeba, Naegleria, Acanthamoeba, Plasmodium, Toxoplasma, Cryptosporidium, Isospora, Balantidium, Schistosoma, Echinostoma, Fasciolopsis, Clonorchis, Fasciola, Opisthorchis, Paragonimus*, Pseudophyllidea (e.g., *Diphyllobothrium*), Cyclophyllidea (e.g., *Taenia*). Pathogenic nematodes include species from the orders; Rhabditida (e.g., *Strongyloides*), Strongylida (e.g., *Ancylostoma*), Ascarida (e.g., *Ascaris, Toxocara*), Spirurida (e.g., *Dracunculus, Brugia, Onchocerca*, Wucheria), and Adenophorea (e.g., *Trichuris* and *Trichinella*), Prototheca, Ptiesteria, *Absidia, Aspergillus, Blastomyces, Candida* (yeast), Cladophialophera, *Coccidioides, Cryptococcus, Cunninghamella, Fusarium, Histoplasma, Madurella, Malassezia, Microsporum, Mucor, Paecilomyces, Paracoccidioides, Penicillium, Pneumocystis, Pseudallescheria, Rhizopus, Rhodotorula, Scedosporium, Sporothrix, Trichophyton* and *Trichosporon*. For the avoidance of doubt the pathogen may include an emerging pathogen.

Illustrative cancer antigens include CD antigens, glycoproteins, glycolipids (gangliosides), carbohydrates (Lewis-Y) vascular targets (VEGF/R), growth factors and stromal or extracellular matrix antigens (FAP, Tenascin) etc. For example, the following as listed: KS 1/4 pan-carcinoma antigen, ovarian carcinoma antigen (CA125), prostatic acid phosphate, prostate specific antigen, melanoma-associated antigen p97, melanoma antigen gp75, high molecular weight melanoma antigen (HMW-MAA), prostate specific membrane antigen, carcinoembryonic antigen (CEA), polymorphic epithelial mucin antigen, human milk fat globule antigen, colorectal tumor-associated antigens, CEA, TAG-72, LEA, Burkitt's lymphoma antigen-38.13, CD19, human B-lymphoma antigen-CD20, CD33, melanoma specific antigens, ganglioside GD2, ganglioside GD3, ganglioside GM2, ganglioside GM3, tumor-specific transplantation type of cell-surface antigen (TSTA), virally-induced tumor antigens, T-antigen DNA tumor viruses, Envelope antigens of RNA tumor viruses, oncofetal antigen-alpha-fetoprotein, CEA of colon, bladder tumor oncofetal antigen, differentiation antigen, human lung carcinoma antigen L6, L20, antigens of fibrosarcoma, human leukemia T cell antigen-Gp37, neoglycoprotein, sphingolipids, breast cancer antigen, EGFR (Epidermal growth factor receptor), HER2 antigen, polymorphic epithelial mucin, malignant human lymphocyte antigen-APO-1, differentiation antigen, including I antigen found in fetal erythrocytes, primary endoderm, I antigen found in adult erythrocytes, preimplantation embryos, I (Ma) found in gastric adenocarcinomas, M18, M39 found in breast epithelium, SSEA-1 found in myeloid cells, VEP8, VEP9, Myl, VIM-D5, Du56-22 found in colorectal cancer, TRA-1-85 (blood group H), C14 found in colonic adenocarcinoma, F3 found in lung adenocarcinoma, AH6 found in gastric cancer, Y hapten, LeY found in embryonal carcinoma cells, TL5 (blood group A), EGF receptor found in A431 cells, E1 series (blood group B) found in pancreatic cancer, FC10. 2 found in embryonal carcinoma cells, gastric adenocarcinoma antigen, CO-514 (blood group Lea) found in Adenocarcinoma, NS-10 found in adenocarcinomas, CO-43 (blood groupLeb), G49 found in EGF receptor of A431 cells, MH2 (blood groupALeb/Ley) found in colonic adenocarcinoma, 19.9 found in colon cancer, gastric cancer mucins, TsA7 found in myeloid cells, R24 found in melanoma, 4.2, GD3, D1.1, OFA-1, GM2, OFA-2, GD2, and M1: 22:25:8 found in embryonal carcinoma cells, and SSEA-3 and SSEA-4 found in 4 to 8-cell stage embryos.

As used herein the term "human immunodeficiency virus" or "HIV" refers to an enveloped positive single-stranded RNA member of the genus Lentivirus and part of the family Retroviridae. Over time HIV causes acquired immunodeficiency syndrome (AIDS). As used herein the term refers to any HIV genotype, for example, but not limited to HIV1 or HIV2 or any group or subtype thereof. In an embodiment, HIV-1 is from group M, N, O or P. In an embodiment, HIV-1 is subtype is selected from A, B, C, D, E, F, G, H, J, K or a circulating recombinant form (CRF) thereof. HIV encodes the envelope proteins glycoprotein (gp) 120 and env.

As used herein the term "hepatitis C virus" or "HCV" refers to an enveloped positive sense, single-stranded RNA virus belonging to the genus Hepacivirus of the Flaviviridae Family. As used herein the term refers to HCV of any genotype, for example, but not limited to strains of HCV genotype 1 (G1), HCV genotype 2 (G2), HCV genotype 3 (G3), HCV genotype 4 (G4), HCV genotype 5 (G5), HCV genotype 6 (G6), HCV genotype 7 (G7) and can include any subtype thereof e.g. subtype a, b, c, d, e, etc. HCV encodes two glycoproteins E1 and E2 which are required for viral entry into host cells.

As used herein "HCV E2" also referred to as "E2" includes an E2 polypeptide from any genotype/subtype of HCV. In an embodiment, E2 is derived from HCV genotype G1, G2, G3, G4, G5, G6, G7, or a chimeric version thereof. Derived from means directly or indirectly based on one or more of these genotypes. Genotypes vary naturally and may be further modified by man and such functional variants, comprising typically conservative mutations are encompassed. Functional variants comprising one or more amino acid mutations are known to the skilled addressee, and may include functional variants comprising a recombinant E2 ectodomain. The terms further include variants, including portions of the full length E2 polypeptide that, for example, mediate receptor binding, antibody binding by one or more antibodies that recognise conformation or other epitopes and/or mediate EIE2 dimer formation. The term includes modified forms of E2 such as modifications to increase immunogenicity (Delta 123 forms) or monomer production (eg. "Ala7").

One illustrative parental HCV E2 polypeptide is a receptor binding portion of E2 polypeptide comprising amino acids 384-661 of genotype H77 1a (E2 661 or E2e) or a corresponding portion from another HCV genotype. Accordingly, E2 polypeptides enabled include all or part of the ectodomain that is required for CD81-binding absent the transmembrane domain. Further variants may include the addition or deletion/disruption of sequences necessary for cleavage or secretion. For example, E384TH may be included, deleted or modified to modify signal peptide cleavage and glycoprotein secretion (McCaffrey et al., 2007). In an embodiment, the E2 polypeptide lacks one or more hypervariable regions or a part thereof. In an embodiment, E2 lacks hypervariable regions, such as one or more of: the hypervariable region 1 (HVR1) or a part thereof, the hypervariable region 2 (HVR2) or a part thereof, and intergenotypic variable region (igVR/VR3) or a part thereof.

In an embodiment, the E2 lacks, HVR1, HVR2 and igVR/VR3. In an embodiment, E2 is Δ123. In an embodiment, E2 comprises the sequence as set forth in SEQ ID NO: 3, 4, 5, 6, 7, or 8; or a fragment thereof that retains CD81 binding activity; or a sequence at least 50%, or at least 55%, or at least 60%, or at least 65%, or at least 70%, or at least 75%, or at least 80%, or at least 85%, or at least 90%, or at least 95%, or at least 97%, or at least 98%, or at least 99% identical thereto.

In an embodiment, E2 comprises zero or one or more mutated or disrupted cysteine/s. Thus, in one embodiment, 1, 2, 3, 4, 5, 6, 7, 8, 9, 10, 11, 12, 13, 14, or 15 cysteines are deleted or disrupted. In one embodiment, these are selected from: C581, C585, C652, C677, C494, C486, C459, C452, C564, C597, C569 and/or C620. In an embodiment, the mutated or disrupted cysteines are C486, C581 and C652. In an embodiment, the mutated or disrupted cysteines are C581, C585 and C652. In an embodiment, the mutated or disrupted cysteines are C452, C486, C581 and C652. In an embodiment, the mutated or disrupted cysteines are C569, C581, C585 and C652. In an embodiment, the mutated or disrupted cysteines are C486, C581 and C652. In an embodiment, the mutated or disrupted cysteines are C452, C486, C569, C581, C585 and C652. In an embodiment, the mutated or disrupted cysteines are C452, C486, C569, C581, C585, C597 and C652. Throughout this specification, including the claims all numbering of polypeptide residues of the HCV glycoprotein E2 is based on the prototype HCV-H77 polypeptide sequence, Genbank Accession No AF009606 (SEQ ID: NO: 6) shown in FIG. 14. The mature form of E2 is encompassed by amino acid residues 384 to 746 of SEQ ID NO: 6, presented separately in SEQ ID NO: 7. Modifications referred to herein are made with reference to the amino acid numbering shown in SEQ ID NO:6 and as shown in FIG. 14.

One illustrative cysteine mutated version of $E2_{661}$ comprises mutation or disruption of the following cysteines: C581, C585, C652, C486, C452, C597, and C569. This mutant is referred to as "Ala7." Further cysteine modified versions of E2 are described in International publication no. WO 2012/016290 incorporated herein in its entirety.

As used herein "CD81" refers to cluster of differentiation 81, which is a transmembrane protein of the tetraspanin superfamily and is a HCV host receptor.

The receptor binding domain (RBD) of HCV E2 comprises CD81-binding motifs and folds and oligomerises into a spectrum of different species each containing different disulfide and glycan arrangements. The inventor/s have done considerable work to identify the disulfide bonding arrangement on monomeric and dimeric WT $E2_{661}$ and Δ123 $E2_{661}$ which suggests that both of these proteins, even as monomeric proteins are actually heterogeneous and present in multiple alternately intramolecular disulfide bonded forms.

When HCV E2 is produced recombinantly, generally 20-30% is oligomeric and approximately 70% is monomeric, depending upon the genotype employed (as determined herein). More monomer is produced with the cysteine modified forms such as Ala7.

Figure 3:
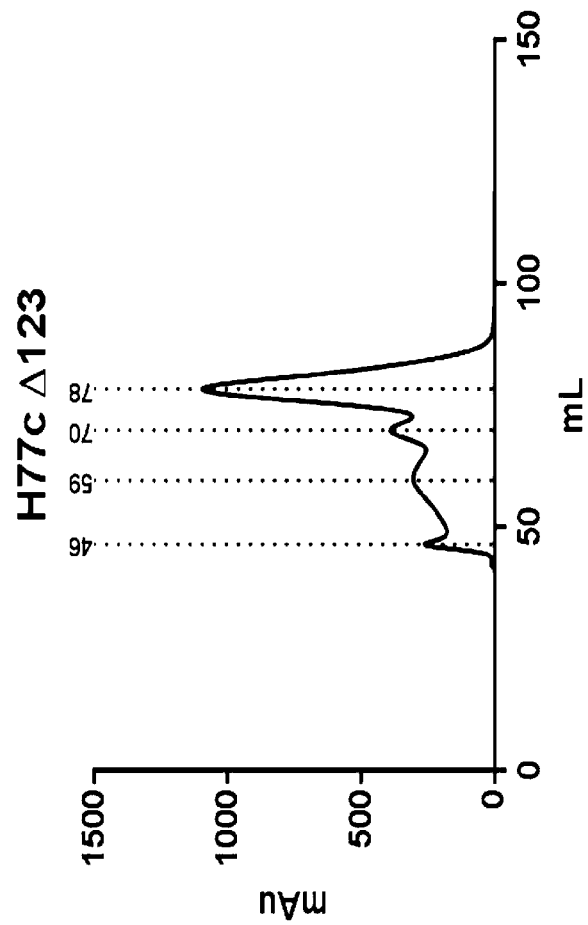
Figure 3:
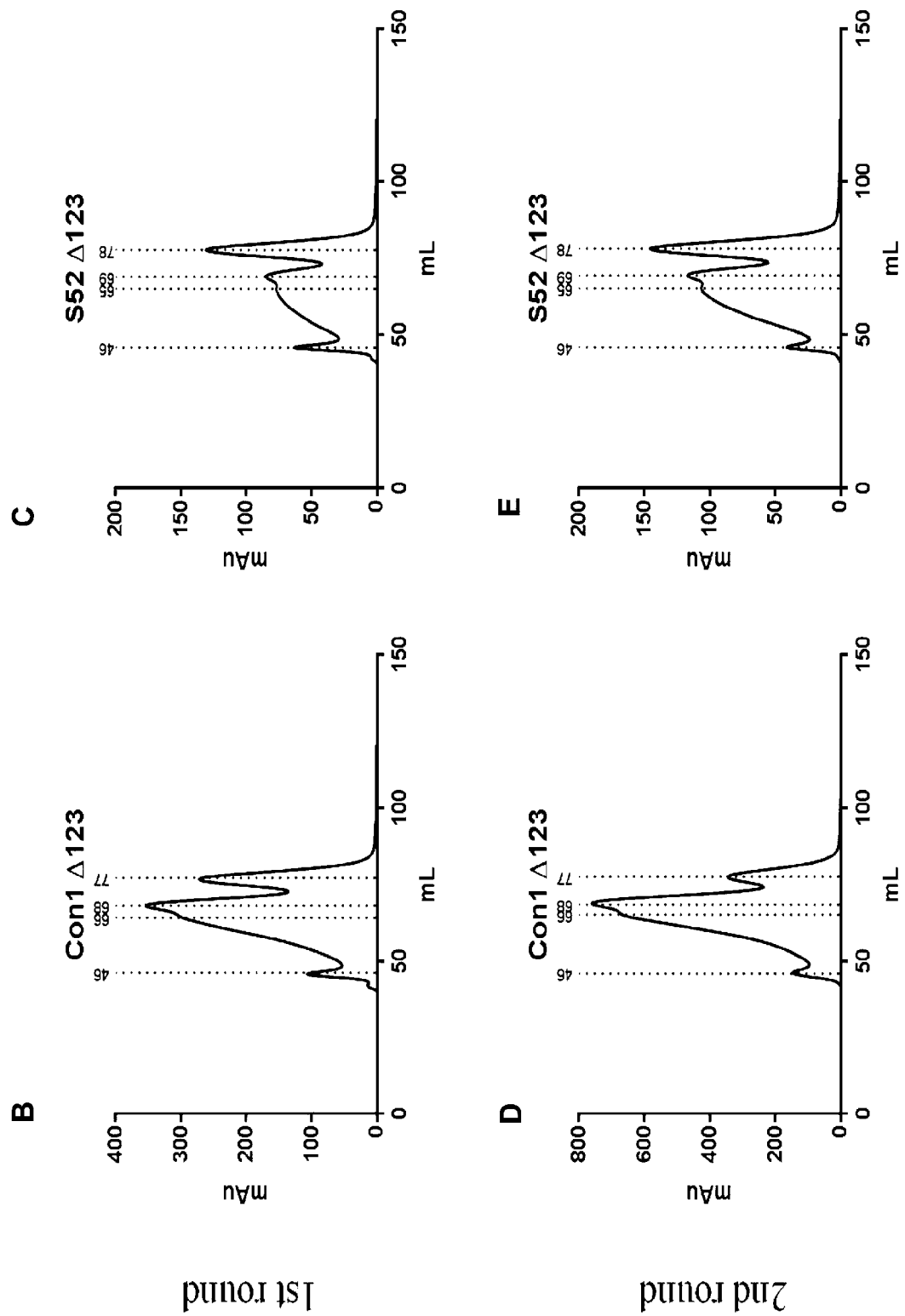
Figure 4:
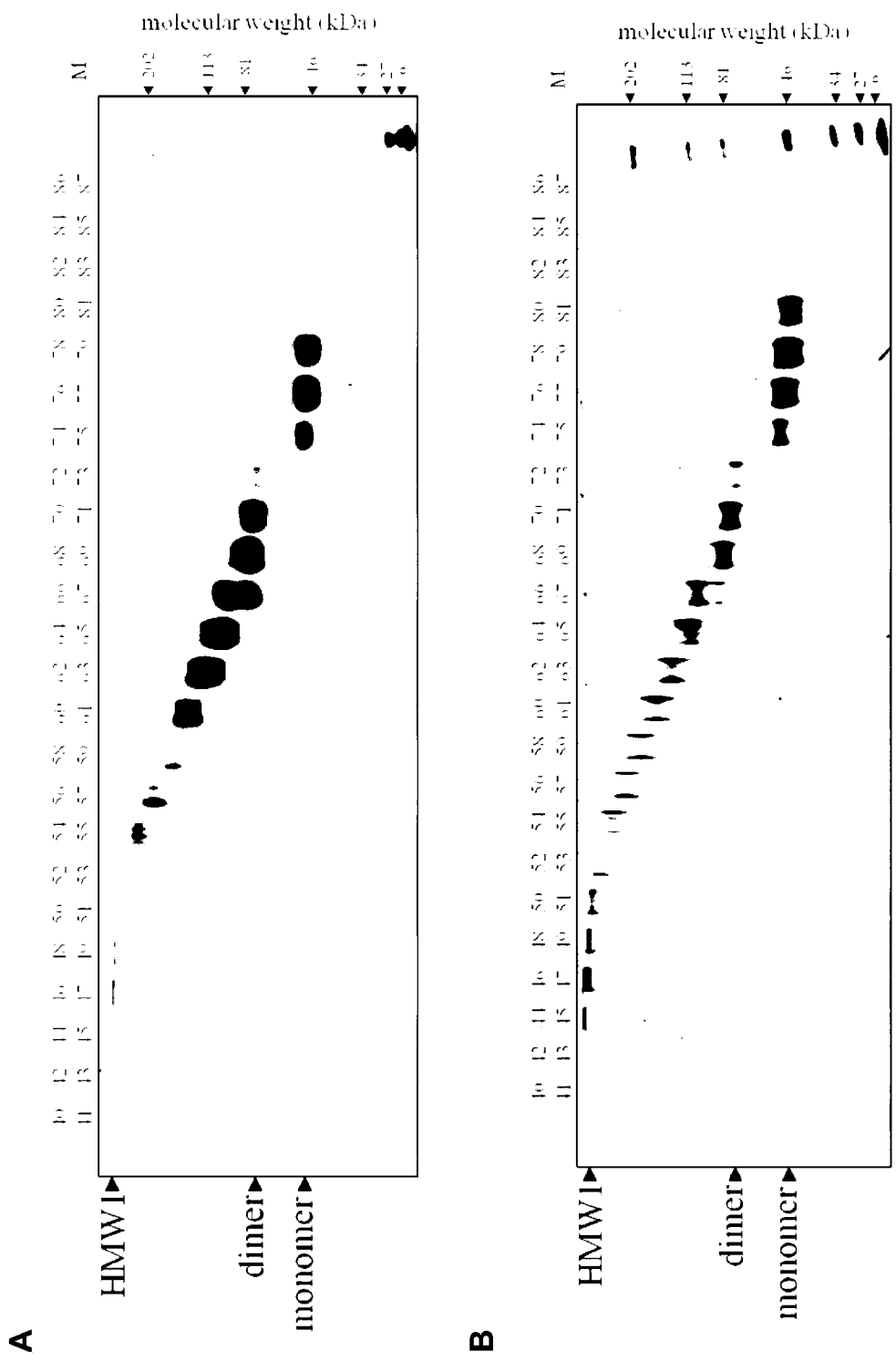
Figure 4:
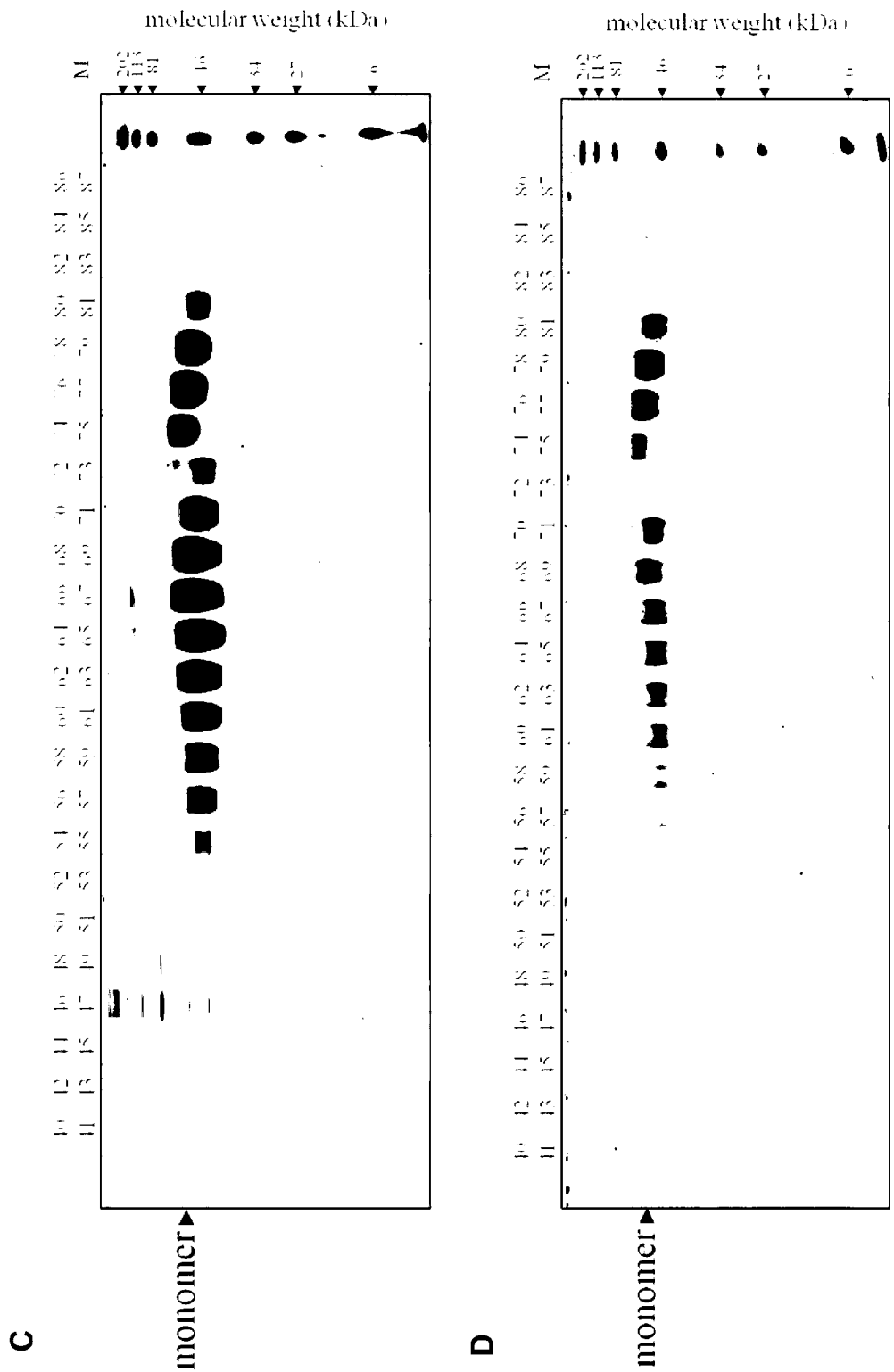

As an example, only approximately 20% of a form of the E2 receptor binding domain (residues 384-661) in which hypervariable region 1 (HVR1), hypervariable region 2 (HVR2) and the intergenotypic variable region (igVR or VR3) have been removed referred to as "delta123" or "Δ123" generated from stable transfection of the Genotype 1a H77c sequence of delta123 into FS293F cells is of the HMW forms, compared to 64.9% for monomers (FIG. 3A). As shown herein this percentage can be increased by selecting a genotype that produces increased amounts of oligomeric forms.

Conventionally, reduction and refolding methods are employed to regenerate lower order species from undesirable aggregates. In accordance with the present invention reduction and re-folding is employed to generate oligomers from monomers or oligomers from monomers and oligomers.

In one embodiment, the present invention provides a method of preparing a refolded recombinant oligomeric hepatitis C virus (HCV) envelope glycoprotein 2 (E2) from native HCV E2, said method comprising the following steps:
  (i) contacting native E2 with a solution comprising a reducing agent for a time and under conditions sufficient to reduce one or more native cysteines (or disulfide bonds); and
  (ii) removing the reducing agent or contacting the reduced native E2 with an oxidising agent to elicit refolding of reduced monomeric E2 into refolded oligomeric HCV E2;
    wherein at least 20% of the monomers are converted to oligomers in step (ii) and the refolded oligomeric HCV E2 displays at least reduced binding to non-neutralizing antibodies compared to the monomeric E2.

In an embodiment, step (i) is performed twice before step (ii). In an embodiment, step (ii) is performed three or more times before step (ii). In some embodiment, steps (i) and (ii) are reparteed two or more times.

In an embodiment, the refolded oligomeric HCV E2 displays at least one characteristic selected from the group consisting of:
  (i) reduced binding to non-neutralizing antibodies relative to a control native HCV E2 form or monomeric E2:
  (ii) at least substantially the same binding to neutralizing antibodies relative to a control native HCV E2 form;
  (iii) elicits the production of lower titres of non-neutralizing antibodies relative to a control native HCV E2 form or monomeric E2;
  (iv) elicits the production of neutralizing antibodies;
  (v) elicits the production of broadly neutralizing antibodies;
  (vi) optionally elicits the production of higher titres of neutralizing antibodies; and
  (vii) optionally elicits the production of higher titres of broadly neutralizing antibodies.

Native HCV E2 monomers can be efficiently produced and effectively purified from a mixture of different HCV E2 species. Native monomeric HCV E2 production as described herein or as known in the art. Native monomeric and oligomeric HCV E2 production as described herein or as known in the art. Typically, protein is produced recombinantly in host cells transformed with a suitable expression vector encoding HCV E2.

Suitable mammalian cell lines include, but are not limited to, BHK, VERO, HT1080, 293, 293T, FS293F, Expi293, RD, COS-7, CHO, Jurkat, HUT, SUPT, C8166, MOLT4/clone8, MT-2, MT-4, H9, PML, CEM, myeloma cells (e.g., SB20 cells) and CEMX174 are available, for example, from the ATCC. Other host cells include without limitation yeast, e.g. *Pichia pastoris*, or insect cells such as Sf9 cells.

The cells may be cultured in a 500 mL, a 1 L, a 1.5 L, a 2 L, a 2.5 L or a 3 L volume. In one example, the cells are cultured using a batch cell culture process. In one example, the cells are cultured using a perfusion cell culture process. In one example, the cells are cultured in a seed medium and a production medium. In one example, the cells are cultured in a stirred-tank reactor. In one example, the volume of the reactor is from about 1 L to about 2500 L. In one example, the reactor is a 1 L reactor, a 1.5 L reactor, a 2 L reactor, a 2.5 L reactor or a 3 L reactor. In one example, the cells are cultured in a wave bioreactor. In one example, the cells are cultured in a cell factory system e.g. a Nunc cell factory system.

Synthetic DNA may be recombinantly expressed by molecular cloning into an expression vector containing a suitable promoter and other appropriate transcription regulatory elements, and transferred into prokaryotic or eukaryotic host cells to produce recombinant protein. Techniques for such manipulations are described by Sambrook et al., Molecular Cloning: A Laboratory Manual (2nd ed.). Cold Spring Harbour Laboratory, Cold Spring Harbour, N.Y., 1989; Ausubel et al., Current Protocols in Molecular Biology, Green Pub. Associates and Wiley-Interscience, New York, 1988.

For example, a construct for expression in yeast preferably contains a synthetic gene, with related transcriptional and translational control sequences operatively linked to it, such as a promoter (such as GAL 10, GAL7, ADH1, TDH3 or PGK), and termination sequences (such as the *S. cerevisiae* ADH1 terminator). The yeast may be selected from the group consisting of: *Saccharomyces cerevisiae, Hansenula polymorpha, Pichia pastoris, Kluyveromyces fragilis, Kluyveromyces lactis,* and *Schizosaccharomyces pombe.* See also Yeast Genetics: Rose et al., A Laboratory Course Manual, Cold Spring Harbor Laboratory, Cold Spring Harbor, N.Y., 1990. Nucleic acid molecules can be codon optimized for expression in yeast as known in the art (see Sharp and Cowe, Yeast, 7:657-678, 1991). Appropriate vectors and control elements for any given cell type can be selected by one having ordinary skill in the art in view of the teachings of the present specification and information known in the art about expression vectors.

Vectors available for cloning and expression in host cell lines are well known in the art, and include but are not limited to vectors for cloning and expression in mammalian cell lines or yeast (fungal) cells, vectors for cloning and expression in bacterial cell lines, vectors for cloning and expression in phage and vectors for cloning and expression in insect cell lines. The expressed proteins can be recovered using standard protein purification methods. Translational control elements have been reviewed by M. Kozak (e.g., Kozak, Mamm Genome, 7 (8): 563-74, 1996; Kozak, Biochimie, 76 (9): 815-21, 1994; Kozak, J Cell Biol, 108 (2): 229-241, 1989; Kozak and Shatkin, Methods Enzymol, 60:360-375, 1979).

Illustrative polynucleotides encoding HCV E2 are provided in the sequence listing and include the polynucleotide sequences set out in SEQ ID NOs: 1 or 2.

Native HCV E2 may be monomeric, dimeric, trimeric, tetrameric, pentameric up to say 23-mers, including forms having a molecular mass of more than 100 kDa or more than 200 kDa (such as HMW1, or HMW2 forms). Monomeric and oligomeric forms may be selected based on size, gel filtration characteristics, antibody reactivity etc. Expressed protein may be purified from cellular components by affinity chromatography, such as by antibody affinity chromatography.

In one embodiment, the method increases the purity of refolded oligomeric HCV E2 compared to native HCV E2 before treatment with the method as described herein. In one embodiment, the method increases the purity of refolded oligomeric HCV E2 compared to native oligomeric HCV E2 isolated from cell culture. As used herein, the term "purified" or "purity" refers to separation of oligomeric HCV E2 from contaminants i.e. cellular or viral contaminants, such as but not limited, proteins, lipids, nucleic acids and carbohydrates.

Furthermore, in one embodiment the method increases the concentration of oligomeric HCV E2 in a sample i.e. from a sample containing monomeric HCV E2 treatment of the sample with the method as described herein increases the concentration of oligomeric HCV E2 by at least 10%, or by at least 20%, or by at least 30%, or by at least 40%, or by at least 50%, or by at least 60%, or by at least 70%, or by at least 80%, or by at least 90%, or by at least 95%. In an embodiment, the method increases the concentration of dimers by at least 10%, or by at least 20%, or by at least 30%, or by at least 40%, or by at least 50%, or by at least 60%, or by at least 70%, or by at least 80%, or by at least 90%, or by at least 95%. In an embodiment, the method increases the concentration of trimeric and/or higher order forms by at least 10%, or by at least 20%, or by at least 30%, or by at least 40%, or by at least 50%, or by at least 60%, or by at least 70%, or by at least 80%, or by at least 90%, or by at least 95%.

In one embodiment, refolded oligomeric HCV E2 shows modified stability compared to a native control oligomeric HCV E2 i.e. modified thermodynamic stability and/or kinetic stability. In one embodiment, refolded oligomeric HCV E2 shows increased stability compared to a native control oligomeric HCV E2.

In one embodiment, refolded oligomeric HCV E2 shows equivalent binding to non-neutralizing antibodies as native oligomeric HCV E2. In an embodiment, the oligomer is a dimer, or a trimer or a tetramer or a pentamer up to a 23mer.

Partial reduction of HCV E2 monomer is preferred. Partial reduction is accomplished when some antibody reactivity with antibodies that recognize conformational epitopes is retained. For example, 10%, 20% or 30% of the protein conformation may be retained in partial reduction protocols used herein.

In one embodiment, reducing conditions include a pH of more than about 7 depending upon the reducing agent used.

The term "oligomer" or "multimer" includes versions of the antigen or E2 that are folded as trimers, tetramers, etc., or high molecular weight (HMW) forms. Different forms are identified, for example, by their migration pattern in non-reducing gel electrophoresis, or by gel filtration chromatography or by their antibody reactivity. In one embodiment, monomers, dimers, HMW2 and HMW delta123 forms have molecular masses of about 46, 97, 239 and 2400, respectively.

In one specific embodiment, the lower order form comprises a dimeric form or the lower order form comprises a monomeric form.

In one embodiment, the oligomeric form is a trimeric form.

In one embodiment, the oligomeric form is trimeric and/or higher order forms.

In one embodiment, the oligomeric form a higher order form such as HMW2 or HMW described herein, or modified forms thereof as described herein.

In one embodiment, the native E2 is a modified form of E2 comprising the receptor binding domain, and lacking the stem region and transmembrane domain.

As known in the art, the transmembrane domain is residues 715-746 and the stem region is residues 662-714. In one embodiment, this form is WT $E2_{661}$.

As described herein, all native forms of HCV E2 comprise different intramolecular and intermolecular (for dimers and higher) disulfide bonded forms. In accordance with one embodiment of the present disclosure, monomers are reduced and refolded into an oligomer, oligomers are reduced and refolded into oligomers, or monomers and oligomers are reduced and refolded into dimers or oligomers.

In one embodiment of the method, at least 25%, at least 30%, at least 40%, at least 50%, at least 60% or at least 70% of the monomers are converted to oligomers.

In another embodiment, at least 70%, 71%, 72%, 73%, 74%, 75%, 76%, 77%, 78%, 79%, 80%, 81%, 82%, 83%, 84%, 85%, or at least 86%, 87%, 88%, 89%, 90%, 91%, 92%, 93%, 94%, 95%, 97%, 98%, 99% of monomers are converted to oligomers.

In one embodiment, the oligomer has an apparent molecular mass of more than 100 kDa. In one embodiment, the oligomer has an apparent molecular mass of more than 200 kDa. In one embodiment, the oligomer has an apparent molecular mass of more than 2000 kDa.

In one embodiment, the method further comprises selecting the HCV genotype which generates the greatest yield of refolded oligomeric HCV E2. In an embodiment, the HCV genotype is selected from G1, G2, G3, G4, G5, G6, G7 and/or other HCV genotype. In an illustrative non-limiting embodiment the HCV genotype is Con1 or S52.

In one embodiment, refolded oligomeric HCV E2 displays reduced binding to antibody CBH4G compared to a control oligomeric HCV E2 not prepared by monomer re-folding. Native oligomers are an example of a control oligomeric HCV E2 not prepared by extracellular monomer re-folding.

In one embodiment of the method, the refolded oligomeric HCV E2 substantially retains the ability of a control oligomeric HCV E2 to bind neutralizing antibodies. In one embodiment of the method, the oligomeric HCV E2 substantially retains the ability of a control oligomeric HCV E2 to bind broadly neutralizing antibodies.

In one embodiment, reducing agents are reversible reducing agents and are for example selected from DTT or 2-mercaptoethanol, Tris(2-carboxyethyl) phosphine, reduced glutathione, thioglycolic acid or other thiol containing agent.

In one embodiment of the method, the reducing agent is dithiothreitol employed at about 0.1-1.0 mM to cause partial reduction of native E2.

In one embodiment of the method, the solution is a buffer at pH>7-9.

In one embodiment, antigen concentration is 1 mg/ml in carbonate buffer pH 9.6. 0.6 mM DTT (final concentration)

is used and incubation is for 1 hour at 37° C. The solution is slowly diluted with PBS pH6.8 and the antigen concentration and buffer exchanged with PBS pH 6.8.

In one embodiment, the native E2 (and consequently the refolded oligomer) lacks all or part of a hypervariable region such as one or more of hypervariable region 1 (HVR1) or a part thereof, the hypervariable region 2 (HVR2) or a part thereof and/or the intergenotypic variable region (igVR/VR3) or a part thereof.

The receptor binding domain comprises variable regions HVR1, HVR2 and igVR that play a role in immune evasion by focusing the immune response on regions that are non-essential for viral invasion and shielding the epitopes of broadly neutralising antibodies. Deletion of at least part of HVR2 and/or igVR and/or HVR1 is effected to focus the immune response on conserved epitopes that elicit broadly neutralising antibodies.

A construct comprising the RBD and lacking all three variable regions is referred to as $E2_{661}$ delta123 or $\Delta 123$ as described in WO 2008/022401. The deleted regions are optionally replaced with a flexible linker sequence described in WO08/022401 (incorporated herein in its entirety) such as a peptide sequence of up to 20 amino acids comprising residues selected form the group comprising Gly, Ser, Ala and Arg (for example GSSG or ETHGSSG).

In an embodiment, the native E2 comprises a signal sequence or protein tag to aid purification. In an embodiment, the signal sequence results in secretion of the protein from a cell. In an embodiment, the signal sequence is an N-terminal signal sequence comprising the amino acid sequence "MNPLLILTFVAAALA" provided in SEQ ID NO: 9. In an embodiment, the protein tag is a C-terminal His-tag. In an embodiment, the C-terminal His-tag comprises the amino acid sequence "HHHHHH".

The inventors have discovered that even monomeric E2 is heterogenous and displays different intramolecular disulfide arrangements. They reasoned that reduction of monomers would provide a good starting point for refolding a more homogeneous oligomer.

In one embodiment, the native E2 comprises a non-cysteine substitution or mutation in one or more of amino acid residues selected from: C581, C585, C652, C677, C494, C486, C459, C452, C564, C597, C569 and/or C620. Surprisingly, even HCV E2 monomers with seven cysteine residues substituted for non-cysteine residues, C452, C486, C569, C597, C581, C585, C652 non-cysteine substitutions (referred to as "Ala7" refolded into higher levels of oligomers.

E2 comprises 18 highly conserved cysteine residues that form 9 intramolecular disulfide bonds in the ER that scaffold the tertiary structure of the glycoprotein. As described in WO 12/016290 (incorporated herein by reference in its entirety), some of these disulfides are dispensable for CD81 binding and MAb H53 binding. Also, cysteine modified forms, including removal of seven cysteine residues, significantly increases monomer production and reduces the production of oligomers. Normally, when E2 is produced recombinantly in host cells it produces a mixture of different monomers and oligomeric forms. WO 12/016290 described the production of various cysteine modified HCV E2. Other constructs disclosed in WO 12/016290 are contemplated herein such as Ala substituted forms having 2, 3, or 4 cysteines mutated or disrupted selected from C452, C486, C569, and C597. $E2_{661}$ lacks the cysteine at C677 and has 17 cysteines In some embodiments the native HCV E2 is cysteine modified form such as Ala4, Ala5, Ala6 or Ala7 modified form of HCV E2 which when expressed recombinantly produces at least 40% monomers and less than 70% oligomers, or at least 50% momomers and less than 50% oligomers in native form.

As determined herein, mutagenesis of C620-Ala blocks high molecular weight oligomer formation. Accordingly native HCV E2 forms are generally C620 for the production of higher order forms.

In another broad aspect, the present description provides a method of preparing a recombinant oligomeric viral envelope glycoprotein from a monomeric envelope glycoprotein, said process comprising the following steps:
  (i) contacting native E2 with a solution comprising a reducing agent for a time and under conditions sufficient to partially reduce one or more disulfide bonds; and
  (ii) removing the reducing agent or contacting E2 from (i) with an oxidising agent to elicit refolding of monomeric E2 into oligomeric envelope glycoprotein;
  and wherein at least 20% of the monomers are converted to a oligomer in step (ii), and the oligomers display at least reduced binding to non-neutralizing antibodies compared to the monomeric glycoprotein.

In an embodiment, step (i) is performed twice before step (ii). In an embodiment, step (ii) is performed three times before step (ii).

In another embodiment, the present specification enables a composition comprising a recombinant refolded oligomeric hepatitis C virus (HCV) E2 glycoprotein produced by the reduction and re-folding methods herein before described.

In one embodiment, the refolded oligomeric proteins comprise an amino acid set out in one of SEQ ID NO: 3, 4, 5, 6, 7, 8 or a truncated or modified version, or functional variant thereof. Functional variants and modified forms may display enhanced immunogenicity compared to the pre-modified form or any other suitable control.

In one embodiment, the composition comprises a recombinant refolded oligomeric hepatitis C virus (HCV) E2 glycoprotein produced by the herein described reduction and re-folding method and wherein the oligomeric HCV E2 displays reduced binding to a non-neutralizing antibody compared to a control HMW E2 not prepared by monomer reduction and re-folding.

In one embodiment, the composition comprises a refolded recombinant oligomeric hepatitis C virus (HCV) E2 glycoprotein produced by the herein described reduction and re-folding method and wherein the refolded oligomeric HCV E2 displays reduced binding to antibody CBH4G or AR3C compared to a control HMW E2 not prepared by monomer reduction and re-folding.

In one embodiment, the composition comprises a refolded oligomeric HCV E2 wherein the refolded oligomeric HCV E2 displays reduced binding to antibody CBH4G compared to a control HMW E2 not prepared by monomer reduction and re-folding. In one embodiment, the composition comprises a refolded oligomeric HCV E2 wherein the refolded oligomeric HCV E2 displays reduced binding to antibody AR3C compared to a control HMW E2 not prepared by monomer reduction and re-folding.

In one embodiment, the composition comprises a monomer refolded oligomeric HCV E2 and a pharmaceutically or physiologically acceptable carrier and/or diluent.

In one embodiment, the composition further comprises an adjuvant.

A person skilled in the art will appreciate that the adjuvant can be any agent that enhances the ability of the composition to induce an immune response. In an embodiment, the adjuvant may act by increasing the immune response to the antigen. In an embodiment, the adjuvant may increase the Th1 and/or Th2 immune response. In an embodiment, the adjuvant may be, an alum salt or other mineral adjuvant; a tensoactive agent; a bacterial derivative; a vehicle or slow release material or a cytokine such as those described in Petrovsky et al (2004) and Wilson-Welder et al. (2009). In one embodiment, the adjuvant may be selected from aluminium phosphate, aluminum hydroxide, potassium aluminum sulfate (alum), calcium phosphate, Freund's complete adjuvant, Freund's incomplete adjuvant, MF-59, a saponin, QS-21, lipopolysaccharide (LPS), monophosphoyl lipid A (MPLA), a Th1 activating peptide (e.g.IMP321), a TLR-2 Ligand (e.g. OspA, muramyl dipeptide (MDP), macrophage activating lipopeptide-2 (MALP-2)), a CpG adjuvant, pertussis toxin, heat liable toxin (LTK63 and LT-R192G), diphtheria toxin, Imiquimod, Addavax, ISCOMATRIX, granulocyte macrophage-colony stimulating factor (GM-CSF), IL-12, IL-6, IL-4, IL-2, IL-1, IFN-g, AS04 (a liposome formulation comtaining MPLA and QS-21), glycerine, and oil emulsions such as paraffin, mineral oil, lanolin, squalene, ISA-70, and montanide. In one illustrative embodiment, the adjuvant is a saponin based adjuvant. In a related aspect, the adjuvant is a saponin based adjuvant further comprises cholesterol and sterol, an illustrative example of which is ISCOMATRIX adjuvant. In one illustrative embodiment, the adjuvant is MF59. In one illustrative embodiment, the adjuvant is Addavax. In one, embodiment the adjuvant is a carbohydrate adjuvant, for example, a glucan, dextran, lentinan, glucomannan or galactomannan.

In one embodiment, the present specification provides for the use of the composition comprising a refolded oligomeric HCV E2 in, or in the preparation of a medicament for, the treatment or prevention of HCV infection.

In one embodiment, the present specification provides for the use of the composition comprising a refolded oligomeric HCV E2 in, or in the preparation of a diagnostic agent for the diagnosis or monitoring of HCV infection or monitoring of an anti-HCV treatment protocol.

In one embodiment, the composition comprises more than 70% or more than 80% by weight, trimeric or trimeric and higher order forms of HCV E2.

In one embodiment, the composition comprises more than 70% or more than 80%, by weight, dimeric HCV E2.

In one embodiment, the composition comprises more than 70% or more than 80%, by weight, higher order forms of HCV E2 glycoprotein.

In one embodiment, the present specification provides a method for eliciting an immune response in a subject or patient, the method comprising administering to the subject or patient an effective amount of the composition comprising a refolded oligomeric HCV E2 as described herein for a time and under conditions sufficient to elicit an immune response.

In accordance with these embodiments, the composition is generally administered for a time and under conditions sufficient to elicit an immune response comprising the generation broadly neutralizing antibodies. The compositions of the present invention may be administered as a single dose or application. Alternatively, the compositions may involve repeat doses or applications, for example the compositions may be administered 2, 3, 4, 5, 6, 7, 8, 9, 10 or more times.

The present invention further provides a method for eliciting an immune response in a subject or patient, the method comprising administering to the subject or patient an effective amount of a composition comprising refolded oligomeric HCV E2 as described herein. A composition, particularly a vaccine composition for immunizing a subject against infection from hepatitis C virus comprising refolded oligomeric HCV E2 as described herein is also contemplated by the present invention.

The term "vaccine" as used herein refers to a pharmaceutical composition comprising at least one immunologically active component that induces an immunological response in a subject and possibly but not necessarily one or more additional components that enhance the immunological activity of said active component (for example an adjuvant). A vaccine may additionally comprise further components typical to pharmaceutical compositions. The immunologically active component of a vaccine comprises a higher order assembled antigen such as a refolded oligomeric HCV E2 composition. The terms "vaccine" and "vaccine composition" are used interchangeably in the present invention.

"Subjects" contemplated in the present invention are humans or animals including laboratory or art accepted test or vehicle animals. "Patients" include human subjects in need of treatment or prophylaxis.

In one embodiment, the specification also enables a method for immunizing a subject against a condition associated with an antigen, comprising administering to the subject the composition comprising assembled or refolded oligomeric antigen as described herein.

In one embodiment, the specification also enables a method for immunizing a subject against infection from HCV, comprising administering to the subject the composition comprising extracellularly refolded oligomeric HCV E2 as described herein.

In one embodiment, the specification also enables method for treating or preventing HCV infection in a subject, comprising administering to the subject the composition comprising extracellularly refolded oligomeric HCV E2 as described herein for a time and under conditions sufficient to treat or prevent HCV infection.

The terms "effective amount" including "therapeutically effective amount" and "prophylactically effective amount" as used herein mean a sufficient amount of a composition of the present invention either in a single dose or as part of a series or slow release system which provides the desired therapeutic, preventative, or physiological effect in some subjects. Undesirable effects, e.g. side effects, may sometimes manifest along with the desired therapeutic effect; hence, a practitioner balances the potential benefits against the potential risks in determining an appropriate "effective amount". The exact amount of composition required will vary from subject to subject, depending on the species, age and general condition of the subject, mode of administration and the like. Thus, it may not be possible to specify an exact 'effective amount'. However, an appropriate 'effective amount' in any individual case may be determined by one of ordinary skill in the art using routine skills or experimentation. One of ordinary skill in the art would be able to determine the required amounts based on such factors as prior administration of the compositions or other agents, the subject's size, the severity of a subject's symptoms or the severity of symptoms in an infected population, viral load, and the particular composition or route of administration selected.

The term "treatment" refers to any measurable or statistically significant amelioration in at least some subjects in one or more symptoms of a condition associated with the antigen such as the E2 antigen and HCV infection, or in the risk of developing advanced symptoms of HCV or the risk of transmitting HCV.

The terms "prevention" and "prophylaxis" and the like are used interchangeably and include administration of a composition of the present invention to a subject not known to be infected with HCV for the purpose of prevention or attenuating a subsequent infection or reducing the risk of becoming infected or reducing the severity or onset of a condition or signs of a condition associated with HCV infection.

The administration of the vaccine composition is generally for prophylactic purposes. The prophylactic administration of the composition serves to prevent or attenuate any subsequent infection. In an embodiment, the vaccine composition is to prevent re-infection of a subject be a pathogen. A "pharmacologically acceptable" composition is one tolerated by a recipient patient. It is contemplated that an effective amount of the vaccine is administered. An "effective amount" is an amount sufficient to achieve a desired biological effect such as to induce enough humoral or cellular immunity. This may be dependent upon the type of vaccine, the age, sex, health, and weight of the recipient. Examples of desired biological effects include, but are not limited to, production of no symptoms, reduction in symptoms, reduction in virus titre in tissues or nasal secretions, complete protection against infection by hepatitis C virus, and partial protection against infection by hepatitis C virus.

In some embodiments, a vaccine or composition of the present invention is physiologically significant if its presence results in a detectable change in the physiology of a recipient patient that enhances or indicates an enhancement in at least one primary or secondary humoral or cellular immune response against at least one strain of an infectious hepatitis C virus. The vaccine composition is administered to protect against viral infection. The "protection" need not be absolute, i.e., the hepatitis C infection need not be totally prevented or eradicated, if there is a statistically significant improvement compared with a control population or set of patients. Protection may be limited to reducing the severity or rapidity of onset of symptoms of the hepatitis C virus infection.

In one embodiment, a vaccine composition of the present invention is provided to a subject either before the onset of infection (so as to prevent or attenuate an anticipated infection) or after the initiation of an infection, and thereby protects against viral infection. In some embodiments, a vaccine composition of the present invention is provided to a subject before or after onset of infection, to reduce viral transmission between subjects.

It will be further appreciated that compositions of the present invention can be administered as the sole active pharmaceutical agent, or used in combination with one or more agents to treat or prevent viral or cancer conditions, such as hepatitis C infections or symptoms associated with HCV infection. Other agents to be administered in combination with a composition or a combination of compositions of the present invention include therapies for disease caused by HCV infection or that suppress HCV viral replication by direct or indirect mechanisms. These agents include, but are not limited to, host immune modulators (for example, interferon-alpha, pegylated interferon-alpha, consensus interferon, interferon-beta, interferon-gamma, CpG oligonucleotides and the like); antiviral compounds that inhibit host cell functions such as inosine monophosphate dehydrogenase (for example, ribavirin and the like); cytokines that modulate immune function (for example, interleukin 2, interleukin 6, and interleukin 12); a compound that enhances the development of type 1 helper T cell response; interfering RNA; anti-sense RNA; vaccines comprising HCV antigens or antigen adjuvant combinations directed against HCV; agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like; and any agent or combination of agents that inhibit the replication of HCV by targeting other proteins of the viral genome involved in the viral replication and/or interfere with the function of other viral targets, such as inhibitors of NS3/NS4A protease, NS3 helicase, NS5B polymerase, NS4A protein and NS5A protein.

According to yet another embodiment, the pharmaceutical compositions of the present invention may further comprise other inhibitor(s) of targets in the HCV life cycle, including, but not limited to, helicase, polymerase, metalloprotease, NS4A protein, NS5A protein, and internal ribosome entry site (IRES).

Administration is generally for a time and under conditions sufficient to elicit an immune response comprising the generation of E2-specific antibodies or cellular immune response. The immunogenic compositions may be administered in a convenient manner such as by the pulmonary, oral, intravenous (where water soluble), intraperitoneal, intramuscular, subcutaneous, intradermal, intrathecal or suppository routes or implanting (e.g. using slow release, formulations). Administration may be systemic or local, although systemic is more convenient. Other contemplated routes of administration are by patch, cellular transfer, implant, sublingually, intraocularly, topically, orally, rectally, vaginally, nasally or transdermally.

As used herein, an "immune response" refers to the reaction of the body as a whole to the presence of a composition of the present invention which includes making antibodies and developing immunity to the composition. Therefore, an immune response to an antigen also includes the development in a subject of a humoral and/or cellular immune response to the antigen of interest. A "humoral immune response" is mediated by antibodies' produced by plasma cells. A "cellular immune response" is one mediated by T lymphocytes and/or other white blood cells. As used herein, "antibody titres" can be defined as the highest dilution in post-immune sera that resulted in a value greater than that of pre-immune samples for each subject.

Embodiments of the present invention also provide assays for assessing an immune response to the refolded oligomeric antigen such as HCV E2. The assays may comprise in vivo assays, such as assays to measure antibody responses and delayed type hypersensitivity responses. In an embodiment, the assay to measure antibody responses primarily may measure B-cell function as well as B-cell/T-cell interactions. For the antibody response assay, antibody titres in the blood may be compared following an antigenic challenge.

The specification provides a method for producing a purified antibody against refolded oligomeric antigen such as HCV E2 as described herein, comprising: administering to a subject an effective amount of refolded oligomeric antigen such as HCV E2; and purifying the antibody produced.

In another embodiment, the present invention provides antibodies raised against refolded oligomeric antigen such as HCV E2. Specific antibodies recognise the assembled antigen while failing to recognise the native antigen and/or vice versa Antibodies may be polyclonal or monoclonal. Further, antibodies may be selected for diagnostic, prognostic, therapeutic, prophylactic, and screening purposes typically using criteria known to those of skill in the relevant art.

The terms "antibody" and "antibodies" include polyclonal and monoclonal antibodies and all the various forms derived from monoclonal antibodies, including but not limited to full-length antibodies (e.g. having an intact Fc region), antigen-binding fragments, including for example, Fv, Fab, Fab' and F(ab').sub.2 fragments; and antibody-derived polypeptides produced using recombinant methods such as single chain antibodies. The terms "antibody" and "antibodies" as used herein also refer to human antibodies produced for example in transgenic animals or through phage display, as well as antibodies, human or humanized antibodies, primatized antibodies or deimmunized antibodies. It also includes other forms of antibodies that may be therapeutically acceptable and antigen-binding fragments thereof, for example single domain antibodies derived from cartilagenous marine animals or Camelidae, or from libraries based on such antibodies. The selection of fragmented or modified forms of the antibodies may also involve consideration of any affect the fragments or modified forms have on the half-lives of the antibody or fragment.

In some embodiments, the antibody is provided with a pharmaceutically or pharmacologically acceptable carrier, diluent or excipient. In other embodiments, the antibody is selected for diagnosis or prognosis. In some embodiments, kits comprising refolded oligomeric forms of HCV E2 glycoprotein antibodies are provided.

A "pharmaceutically acceptable carrier and/or a diluent" is a pharmaceutical vehicle comprised of a material that is not otherwise undesirable i.e., it is unlikely to cause a substantial adverse reaction by itself or with the active composition. Carriers may include all solvents, dispersion media, coatings, antibacterial and antifungal agents, agents for adjusting tonicity, increasing or decreasing absorption or clearance rates, buffers for maintaining pH, chelating agents, membrane or barrier crossing agents. A pharmaceutically acceptable salt is a salt that is not otherwise undesirable. The agent or composition comprising the agent may be administered in the form of pharmaceutically acceptable non-toxic salts, such as acid addition salts or metal complexes.

For oral administration, the compositions can be formulated into solid or liquid preparations such as capsules, pills, tablets, lozenges, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. Tablets may contain a binder such as tragacanth, corn starch or gelatin; a disintegrating agent, such as alginic acid; and a lubricant, such as magnesium stearate. If desired, tablets may be sugar-coated or enteric-coated by standard techniques. The active composition can be encapsulated to make it stable to passage through the gastrointestinal tract. See for example, International Patent Publication No. WO 96/11698.

For parenteral administration, the composition may be dissolved in a carrier and administered as a solution or a suspension. For transmucosal or transdermal (including patch) delivery, appropriate penetrants known in the art are used for delivering the composition. For inhalation, delivery uses any convenient system such as dry powder aerosol, liquid delivery systems, air jet nebulizers, propellant systems. For example, the formulation can be administered in the form of an aerosol or mist. The compositions may also be delivered in a sustained delivery or sustained release format. For example, biodegradable microspheres or capsules or other polymer configurations capable of sustained delivery can be included in the formulation. Formulations can be modified to alter pharmacokinetics and biodistribution. For a general discussion of pharmacokinetics, see, e.g., Remington's Pharmaceutical Sciences, 18$^{th}$ Ed., Mack Publishing Company, Easton, PA, U.S.A. 1990 (supra). In some embodiments the formulations may be incorporated in lipid monolayers or bilayers such as liposomes or micelles. Targeting therapies known in the art may be used to deliver the agents more specifically to certain types of cells or tissues.

The actual amount of active agent administered and the rate and time-course of administration will depend on the nature and severity of the disease. Prescription of treatment, e.g. decisions on dosage, timing, etc. is within the responsibility of general practitioners or specialists and typically takes into account the condition of the individual patient, the site of delivery, the method of administration and other factors known to practitioners. Examples of techniques and protocols can be found in Remington's Pharmaceutical Sciences, 1990 (supra).

Sustained-release preparations that may be prepared are particularly convenient for inducing immune responses. Examples of sustained-release preparations include semipermeable matrices of solid hydrophobic polymers containing the polypeptide, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers, and poly-D-(−)-3-hydroxybutyric acid. While polymers such as ethylene-vinyl acetate and lactic acid-glycolic acid enable release of molecules for over 100 days, certain hydrogels release proteins for shorter time periods. Liposomes may be used which are of the small (about 200-800 Angstroms) unilamellar type in which the lipid content is greater than about 30% cholesterol, the selected proportion being adjusted for the optimal therapy.

Stabilization of proteins may be achieved by modifying sulfhydryl residues, lyophilizing from acidic solutions, controlling moisture content, using appropriate additives, and developing specific polymer matrix compositions. The in vivo half-life of proteins may be extended using techniques known in the art, including, for example, by the attachment of other elements such as polyethyleneglycol (PEG) groups.

Prime-boost immunization strategies as disclosed in the art are contemplated. See for example International Publication No. WO/2003/047617. Thus, compositions may be in the form of a vaccine, priming or boosting agent.

In one embodiment, the present specification provides a kit, or a solid or semi-solid substrate, comprising the composition comprising a reduced and refolded oligomeric HCV E2 form as described herein.

The term "isolated" means material that is substantially or essentially free from components, that normally accompany it in its native state. For example, an "isolated nucleic acid molecule" refers to a nucleic acid or polynucleotide, isolated from the sequences which flank it in a naturally-occurring state, e.g., a DNA fragment which has been removed from the sequences that are normally adjacent to the fragment. Without limitation, an isolated nucleic acid, polynucleotide, peptide, or polypeptide can refer to a native sequence that is isolated by purification or to a sequence that is produced by recombinant or synthetic means. In some embodiments, purified refolded oligomeric HCV E2 is at least 95 to 99% pure.

A person skilled in the art will appreciate that the refolded oligomer HCV E2 produced by the methods as described herein can be purified by any method known to a person skilled in the art, including, for example one or more of the following steps: centrifugation, microfiltration, antibody purification, depth filtration ultrafiltration, diafiltration, precipitation, bead chromatography (for example size exclusion chromatography, ion exchange chromatography or affinity chromatography), membrane adsorber (for example ion exchange chromatography or affinity chromatography). In one example, the refolded oligomeric HCV E2 produced by the methods as described herein comprises a protein tag, such as a HIS-tag which aids purification of the refolded oligomeric HCV E2.

In one embodiment, the specification enables a method of preparing a refolded recombinant oligomeric hepatitis C virus (HCV) envelope glycoprotein 2 (E2) from recombinant HCV E2, wherein the recombinant E2 is monomeric E2 or comprises a mixture of monomeric and oligomeric recombinant E2 said method comprising the following steps: (i) contacting recombinant E2 with a solution comprising a reducing agent for a time and under conditions sufficient to reduce one or more monomer disulfide bonds; and (ii) removing the reducing agent or contacting the monomer with an oxidising agent to elicit refolding of recombinant E2 into oligomeric HCV E2; wherein the refolded recombinant oligomeric E2 comprises at least 20% more oligomers than recombinant E2 prior to refolding (ii) and the refolded oligomeric HCV E2 displays reduced binding to non-neutralizing antibodies compared to the recombinant monomeric E2.

In some embodiments refolded oligomeric E2 comprises dimers, trimers, and/or higher order forms of E2.

In another aspect the present specification provides a more general method of preparing a refolded recombinant oligomeric viral envelope glycoprotein from a native envelope glycoprotein, said process comprising the following steps: (i) contacting native E2 with a solution comprising a reducing agent for a time and under conditions sufficient to partially reduce one or more monomer disulfide bonds or native cysteines; and
(ii) removing the reducing agent or contacting the reduced native HCV E2 with an oxidising agent to elicit refolding of reduced monomeric envelope glycoprotein into oligomeric envelope glycoprotein;
and wherein at least 20% of the monomers are converted to refolded oligomers in step (ii), and the oligomers display at least reduced binding to non-neutralizing antibodies compared to the monomeric glycoprotein.

A person skilled in the art will appreciate that once produced higher order antigen as described may be purified by any method know to a person skilled in the art. For example "purifying" or "purification" may comprise one or more of the following steps: centrifugation (e.g. ultracentrifugation), chromatography (e.g. size exclusion chromatography, ion exchange chromatography or affinity chromatography), and/or membrane adsorber (for example ion exchange chromatography or affinity chromatography), filtration (e.g. membrane filtration, ultrafiltration or diafiltration).

A person skilled in the art would appreciate that purified higher order antigen can be formulated into pharmaceutical formulations such as vaccine compositions. Such compositions can comprise one or more of: an adjuvant, an excipient, a binder, a preservative, a carrier coupling, a buffering agent, a stabilizing agent, an emulsifying agents, a wetting agent, a non-viral vector and a transfection facilitating compound. A skilled person would further understand that such vaccine compositions can be lyophilized. In one embodiment, the vaccine composition produced is suitable for human use. In another embodiment, the vaccine is suitable for veterinary use.

The higher order antigen or composition as described herein may be used to bind to/detect antigen specific immune cell. In an embodiment, the immune cell is a B-cell. In an embodiment, the immune cell is a T-cell. Detection of antigenic immune cells indicate that a subject has been infected with the pathogen associated with the antigen and/or that the subject has been vaccinated with an antigen. In an embodiment, the higher order antigen as described herein, or the composition as described herein may be used for the detection and/or isolation of B-cells specific for an enveloped virus. In an embodiment, the enveloped virus is HCV. In an embodiment, the enveloped virus is HIV.

A person skilled in the art would appreciate that higher order antigens of the present invention are suitable for use in diagnostic assays and/or isolation of an immune cell. In an embodiment, the higher order antigen may be used as a stain or marker for of an immune cell in flow cytometry. In an embodiment, the higher order antigen is complexed with a marker, dye or fluorophore to allow for detection using flow cytometry. In an embodiment, the marker is d-biotin.

Isolation of immune cell/s may involve a "tetramer assay" or "tetramer stain", for example as described in Altman et al., (1996), Vollers et al., 2008 and Dolton et al, 2015, wherein a higher order antigen as described herein replaces the role of the major histocompatibility complex (MHC) tetramer in the assay.

In an embodiment, the invention provides a method for detection and/or isolation of immune cells/B-cell specific for HCV comprising: i) labelling an immune cell/B-cell specific for HCV with the higher order antigen as describe herein; and ii) detecting and/or isolating the labelled immune cell/B-cell cytometrically.

Reference to variants includes parts, derivatives, and chemical analogs. Chemical analogs contemplated include modification of side chains, incorporation of unnatural amino acids and/or their derivatives during synthesis and the use of linkers or cross-linkers or other methods to inter alia impose conformational constraints.

The disclosure is completed with the following non-limiting examples of the assembly method and characteristics of the assembled higher order antigens. As noted above, although the disclosure is illustrated using hepatitis and HIV envelope antigens, the invention extends to antigens produced using the subject methods, forming higher order oligomers from lower order antigens in order to enhance the antigenicity and immunogenicity of the antigen. As described herein, the higher order antigens are further characterised using a range of techniques known in the art. However, analysis to date shows the assembled oligomers, produced by the reduction and assembly methods described herein display antibody binding profiles not displayed by

EXAMPLES

Example 1: Expression Vectors and Plasmids

Cloning. The DNA sequence of HCV E2 Δ123 fused with a C-terminal 6× histidine (HIS) tag (SEQ ID NO: 24) and was cloned into a pcDNA3.1 mammalian expression vector (Invitrogen). Con1 genotype 1b (G1b) Δ123 (SEQ ID NO:20) was cloned by CSL. H77c genotype 1a (G1a) Δ123 (SEQ ID NO:19) was also cloned by CSL, but into a proprietary CSL-modified pcDNA3.1 vector. The resultant plasmids containing H77c Δ123 and Con1 Δ123 were named pcDNA-H77cΔ123-HIS and pcDNA-Con1Δ123-HIS, respectively. The DNA sequence of S52 G3a Δ123 (SEQ ID NO: 21) was ligated into the NheI and XbaI sites of pcDNA3.1 using T4 DNA ligase to produce pcDNA-S52Δ123-HIS.

DNA Expression and Purification. pcDNA-Con1Δ123-HIS and pcDNA-S52Δ123-HIS were transformed into DH5α *Escherichia coli* using the heat shock method (Froger and Hall, 2007) and then grown on Luria-Bertani (LB) ampicillin (100 µg/mL) agar plates. Single colonies were cultured in ampicillin-containing (100 µg/mL) LB broth and DNA plasmids were extracted using the QIAGEN plasmid maxi prep kit according to the manufacturer's recommendations. To confirm successful ligation and scale up of the cloned plasmids, pcDNA-Con1Δ123-HIS and pcDNA-S52Δ123-HIS from the maxi prep were digested with NheI and XhoI; and NheI and XbaI restriction enzymes, respectively. Resultant digests were then subjected to agarose gel electrophoresis and the gel was viewed using the Gel Doc XR+system (Bio-Rad Laboratories) and the Quantity One 1-D analysis software (Bio-Rad Laboratories) to confirm the expected restriction pattern. Plasmids were also sequenced (by Micromon) using BigDye Terminator v3.1 chemistry and the sequences were analysed using CLC Sequence Viewer (QIAGEN) and FinchTV (Geospiza).

Example 2: Protein Expression and Purification

Transient Transfection. FreeStyle 293-F (FS293F) cells (Invitrogen), derived from the human embryonic kidney 293 cell line, were seeded at $1 \times 10^6$ viable cells/mL in 150 mL in 1 L Erlenmeyer cell culture flasks (Corning) and maintained in FreeStyle 293 (FS293) expression media (Invitrogen). Cells were incubated at 37° C. in a humidified atmosphere with 8% $CO_2$ using a Steri-Cycle $CO_2$ incubator (Thermo Electron Corporation), and on an orbital shaker rotating at 4× relative centrifugal force (RCF). Transient transfections of pcDNA-Con1Δ123-HIS and pcDNA-S52Δ123-HIS into FS293F cells were performed using the 293fectin transfection reagent (Invitrogen) according to the manufacturer's instructions, using the volumes shown in Table 1. On day 1 post-transfection, 100 mL FS293 expression medium was added, raising the total transfection volume to 250 mL. Cell cultures were also supplemented with 0.5% lupin peptone (Solabia Biotechnology) and 0.02% Pluronic F-68 (Gibco). A half media change was performed on days 3, 5 and 7 post-transfection, whereby half of the cell culture supernatant (125 mL) was harvested by centrifugation at 300× RCF for 5 min. Pelleted cells were resuspended in 125 mL of fresh FS293 expression medium, also supplemented with 0.5% lupin peptone and 0.02% Pluronic F-68, and then returned to the cell culture flasks. Finally, a full harvest of the cell culture supernatant (250 mL) was performed on day 9 post-transfection. All harvested supernatants were subjected to further centrifugation at 15,344× RCF for 30 min and pellets were discarded to remove residual cells and cellular debris. Cell counting was performed on each day of harvest using the trypan blue dye exclusion method and a hemocytometer to determine the cell density and viability.

Affinity Chromatography. Cell culture supernatants containing secreted HIS-tagged Δ123 glycoproteins were applied to 10 mL (i.e. 1 column volume) cobalt-charged TALON metal affinity resin (ClonTech) for 2 h on a rocker at room temperature (RT) to allow binding of the HIS-tagged proteins. The beads were washed twice with 20 column volumes of wash buffer (50 mM sodium phosphate, 300 mM sodium chloride, pH 7.0) at a flow rate of 5 mL/min and eluted with 5 column volumes of elution buffer (50 mM sodium phosphate, 300 mM sodium chloride, 200 mM imidazole, pH 7.0) at a flow rate of 1 mL/min. Proteins contained within eluates were concentrated using Amicon Ultra centrifugal filter units (Merck Millipore) with a molecular weight cut-off (MWCO) of 30 kDa, washed in phosphate-buffered saline (PBS, Gibco) which was adjusted to pH 6.8 (PBS pH 6.8) using hydrochloric acid (HCl) and stored at 4° C. until used.

Example 3: Gel Filtration Chromatography

Proteins were subjected to gel filtration chromatography on a Superdex 200 prep grade 16/600 column (GE Healthcare) using the ÄKTA fast protein liquid chromatography (FPLC) system (GE Healthcare). The run was conducted at a flow rate of 0.5 mL/min using filtered and degassed PBS pH 6.8 as the running buffer. Fractions containing the desired oligomeric species were pooled then concentrated using Amicon Ultra centrifugal filter units with a MWCO of 10 kDa and stored in PBS pH 6.8 until used. Protein concentrations were determined by spectrophotometry at an optical density of 280 nm ($OD_{280}$) using a cuvette with a 1 cm path length and calculated in mg/mL using the following formula:

$$\text{extinction coefficient} \times \text{absorbance at } OD_{280}$$

The amino acid sequences of Δ123 were used to determine the extinction coefficients, which were calculated using the following formula:

$$\text{molecular weight}(Da)/((5690 \times \text{\#tryptophans}) + (1280 \times \text{\#tyrosines}))$$

Example 4: Polyacrylamide Gel Electrophoresis (PAGE)

Proteins were analysed via sodium dodecyl sulfate (SDS)-PAGE under reducing or non-reducing conditions as appropriate. For reducing SDS-PAGE, protein samples were heated at 100° C. for 5 minutes in 1× sample buffer containing 2% (v/v) β-mercaptoethanol and then loaded onto a 12% acrylamide gel along with broad-range SDS-PAGE standards (Bio-Rad Laboratories). Electrophoresis was conducted using a vertical electrophoresis apparatus (CLP) in 1× running buffer (25 mM Tris base, 192 mM glycine, 0.1% SDS, pH 8.3) at 180V for ~1.5 h. Non-reducing SDS-PAGE was performed in the same way, but with a 4-12% polyacrylamide gradient gel and without β-mercaptoethanol in the sample buffer. Gels were stained with 0.25% (v/v) Coomassie brilliant blue R-250 (Bio-Rad Laboratories), 10% (v/v) acetic acid and 50% (v/v) methanol, then destained with 10% (v/v) acetic acid and 50% (v/v) methanol and scanned using an Odyssey infrared imaging system (LI-COR). Band intensities were also quantitated using the Odyssey system.

Example 5: Antibodies

Monoclonal antibodies (MAbs) AR3A, AR3B, AR3C and AR3D kind gifts from Dr Mansun Law, The Scripps Research Institute (Law et al. 2008). CBH-4B, CBH-4D, HC-11 and HCV-1 were kind gifts from Dr. Steven Foung, Standford University. H52 and H53 were kind gifts of Dr. Jean Dubuisson and Dr. Harry Greenberg. MAbs 1, 7, 10, 12, 16, 20, 24 and 60 were produced by our laboratory in collaboration with CSL Ltd (Table 2). Suitable antibody panels are described in the literature, for example, in Keck et al. *PLos Pathogens:* 8 (4) e1002653, April 2012. Also, antibody 2A12 displayed reduced binding to assembled E2 relative to a native control oligomeric HCV E2.Antibody panels and how to generate them are described in Vietheer P. et al. *Hepatology:* 65 (4), 1117-1131, 2017 incorporated herein by reference, and references referred to therein such as references 5, 33-36, 17 and 37 and supplemental materials, available from the publisher.

Example 6: Enzyme Linked Immunosorbent Assays (ELISA)

Sandwich ELISA. To confirm successful protein expression and purification, sandwich ELISA were performed using Maxisorb flat-bottom 96 well plates (Nunc). Wells were coated with 5 µg/mL dimeric maltose binding protein (MBP)-CD81-LEL$^{113-201}$ in 50 mM carbonate-bicarbonate buffer pH 9.6 and then incubated overnight at 4° C. Plates were washed 4 times in PBS containing 0.05% Tween 20 (PBST) in this and subsequent washing steps and then blocked with 10 mg/mL bovine serum albumin (BSA, Sigma-Aldrich) in PBS (BSA10PBS) for 1 h at RT. After washing, half-logarithmic serial dilutions of tissue culture supernatants were performed in PBST containing 5 mg/mL BSA (BSA5PBST), followed by incubation for 1 h at RT. After washing, a single dilution of rabbit anti-6xHIS epitope tag antibodies (Rockland Immunochemicals) in BSA5PBST were added and incubated for 1 h at RT. Following washing, a single dilution of goat anti-rabbit immunoglobulins (Dako) conjugated to horse radish peroxidase (HRP) was added. After washing, ELISA development was performed using 3,3',5,5'-Tetramethylbenzidine (TMB) substrate (Sigma-Aldrich) according to the manufacturer's instructions and the reaction was stopped with 1M HCl. Finally, optical densities were measured at 450 nm using a Multiskan Ascent microplate reader (Thermo Electron Corporation).

Single Dilution Point Assessments and Direct ELISA. To assess the reactivity of Δ123 to a panel of antibodies known in the art such as the panel of antibodies listed in Example 5/Table 2, single dilution point assessments were initially performed whereby Maxisorb flat-bottom 96 well plates were directly coated with 5 µg/mL monomeric Δ123 and then incubated overnight at 4° C. After washing and blocking with BSA10PBS, a single dilution of the primary antibodies was added, followed by the addition of secondary antibody (Dako), with washing and 1 hour incubation at RT in between each addition. The plates were developed and measured as described above for sandwich ELISAs. Direct ELISA was performed by the same method, but wells were coated with either 2 µg/mL monomeric Δ123 or 5 µg/mL HMW1 Δ123 as appropriate and the primary antibodies were subjected to half-logarithmic serial dilutions in BSA5PBST.

Example 7: Protein Reduction and Refolding

Small Scale Reduction. To determine the optimal DTT (Pierce) concentration for use in protein reduction, a Maxisorb flat-bottom 96 well plate was coated with 5 µg/mL monomeric H77c Δ123 in 50 mM carbonate-bicarbonate buffer of pH 9.6, and incubated at RT for a minimum of 2 h. After washing 4 times with PBST, different concentrations of DTT (0-10 mM) prepared in carbonate-bicarbonate buffer were added and incubated at 37° C. for 30 min. The plate was then immediately washed 6 times in PBST to remove the DTT, followed by blocking with BSA10PBS. The primary antibodies, which include anti-HIS, H53 and R04, followed by the appropriate secondary antibodies were added, as described in Example 6. Finally, bound antibodies were detected and measured as described in Example 6. The same experiment was repeated using TCEP as the reducing agent.

Reduction and Refolding with DTT in Solution. H77c Δ123 monomers prepared in carbonate-bicarbonate buffer were subjected to DTT reduction under different conditions (Table 3) to determine the requirements for optimal HMW Δ123 formation. Protein refolding was conducted by means of slow dilution, which was achieved through 3 stepwise additions of PBS pH 6.8 at a constant volume that was half of the initial sample volume. For example, 4×200 µL of PBS pH 6.8 would be added to a 400 µL sample. Each addition was followed by 15 min incubation at RT. DTT was removed using Amicon Ultra centrifugal filter units with a MWCO of 10 kDa, followed by two rinses in PBS pH 6.8. The refolded proteins were then analysed by non-reducing SDS-PAGE as described in Example 4. Larger scale refolding was conducted if multimers were successfully formed and analysed by gel filtration chromatography, as described in Example 3.

Reduction and Refolding Using the Redox-Shuffling System. A ratio of 1:5 oxidised L-glutathione (GSSG, Pierce) to reduced L-glutathione (GSH, Pierce) was added to H77c Δ123 monomers prepared in carbonate-bicarbonate buffer, with different conditions explored (Table 4). The reaction was stopped by removing L-glutathione and the refolded proteins were then analysed, as described in Example 7. Larger scale refolding was conducted if multimers were successfully formed and analysed by gel filtration chromatography, as described in Example 3.

Crosslinking Tris(2-carboxyethyl) phosphine hydrochloride (TCEP)-Reduced Proteins with Bismaleimidoethane (BMOE). Different concentrations of TCEP were added to H77c Δ123 monomers, prepared in PBS pH 6.8 at different concentrations (Table 5), and incubated for 30 min at 37° C. BMOE (Sigma), dissolved in dimethyl sulphoxide (Sigma) immediately prior to use, was then added to a final concentration of 0.2 mM and incubated for 1 h at RT as instructed by the manufacturer. The reaction was stopped by removing BMOE and TCEP, and the refolded proteins were then analysed, as described in Example 7.

Example 8: Production of Δ123

Figure 1:
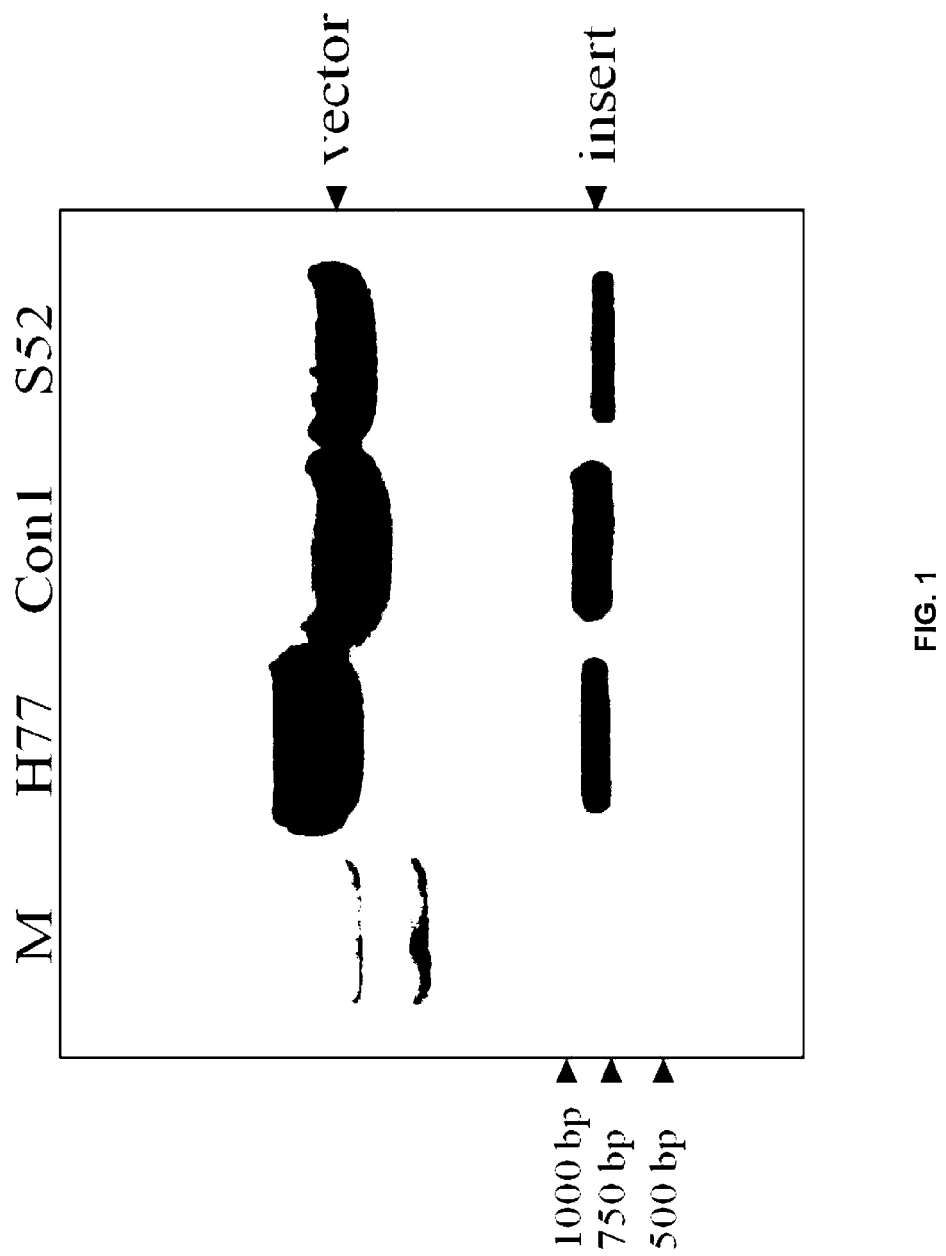

The DNA sequences of Δ123 from strains H77c, Con1 and S52 were incorporated into pcDNA3.1 based vectors, giving rise to the following plasmids: pcDNA-H77cΔ123-HIS, pcDNA-Con1Δ123-HIS and pcDNA-S52Δ123-HIS. These plasmids displayed the expected restriction patterns on agarose gel electrophoresis, with bands representing H77c, Con1 and S52 Δ123 inserts all corresponding to their expected lengths of 762, 759 and 710 bp, respectively (FIG. 1). H77c Δ123 was cloned into a proprietary CSL-modified pcDNA3.1 vector, accounting for the larger vector size observed compared to the standard Invitrogen vectors containing Con1 and S52, which each migrated to the same horizontal position (FIG. 1).

Transient transfections of Con1 and S52 Δ123 plasmids into mammalian FS293F cells were performed to produce Δ123 glycoproteins. Cells were maintained in suspension in FS293 expression media supplemented with Pluronic F-68 to protect cells against hydrodynamic forces, and lupin peptone to boost growth efficiency. Cells were seeded at $1 \times 10^6$ viable cells/mL, and the cell viability was maintained at approximately 90% from days 0 to 9 post-transfection. To confirm successful expression of Δ123 glycoproteins, cell culture supernatants were analysed via sandwich ELISA (FIG. 2A-B). Half-logarithmic serial dilutions of supernatants harvested on days 3, 5, 7 and 9 post-transfection were applied to dimeric MBP-CD81-LEL[113-201]-coated enzyme immunoassay plates, and captured Δ123 glycoproteins were detected with rabbit anti-his antibodies and HRP-conjugated goat anti-rabbit immunoglobulins. Monomeric H77c Δ123 at a concentration of 1 µg/mL in the first well served as a positive control, whereas HIV envelope protein gp140-containing supernatant diluted to 1/2 in the first well served as a negative control. All cell culture supernatants exhibited positive binding to CD81, indicating the presence of Δ123 glycoproteins in the supernatants and thus successful protein expression. Furthermore, curves representing cell culture supernatants appeared above the positive control, indicating yields >1 µg/mL of Δ123 glycoproteins-approximately 4 µg/mL and 20 µg/mL for Con1 and S52, respectively. Optical density (OD) values were highest for harvests performed at days 5 and 7, suggesting that protein expression was somewhat more efficient at these intermediate time points. It was also noted that supernatants from the S52 Δ123 transfection demonstrated greater levels of CD81 binding compared to that of Con1 Δ123, suggesting more efficient protein expression for the S52 strain or that S52 Δ123 has a stronger affinity for CD81.

To isolate Δ123 glycoproteins from the cell culture supernatants, affinity chromatography was performed using TALON beads, a sepharose matrix charged with cobalt, which efficiently binds to his-tagged proteins with higher specificity than conventional nickel-affinity supports. The effectiveness of protein purification was also analysed via sandwich ELISA in the same way as conducted for cell culture supernatants (FIG. 2 C-D). Eluates were sequentially collected into three separate fractions, with the proteins eluted in the first fraction showing similar levels of CD81 binding as the supernatant before purification, indicating that fraction 1 contained most of the Δ123 glycoproteins. The proteins eluted in fraction 2 exhibited decreased CD81 binding, indicating that a lesser amount of Δ123 was present, while that of fraction 3 showed negligible CD81 binding and produced a curve that aligned with the HIV gp140 negative control. Supernatants after purification (i.e. flow through) and the wash from S52 Δ123 purification showed virtually similar levels of CD81 binding to the positive control, while low levels were observed for that of Con1 Δ123, indicating that Con1 Δ123 purification was performed more effectively.

Example 9: 4123 Expression Profiles

The DNA sequences of Δ123 from strains previous analysis of affinity-purified H77c Δ123 expression by gel filtration chromatography revealed that H77c Δ123 exists as a spectrum of differently sized species (FIG. 3A). These consist of monomers, dimers, HMW2 and HMW1 Δ123, which have molecular masses of 46, 97, 239 and 2402 kDa respectively, and vary in their antigenicity as well as immunogenicity (H. Drummer, unpublished data). HMW species are able to induce bNAbs, whereas monomers induce type-specific NAbs (H. Drummer, unpublished data). However, only 23.13% of Δ123 generated from stable transfection of H77c Δ123 into FS293F cells (performed by Dr. Rob J Center prior to the commencement of this project) were of the HMW form, compared to 64.90% for monomers (FIG. 3A and Table 6).

Figure 5:
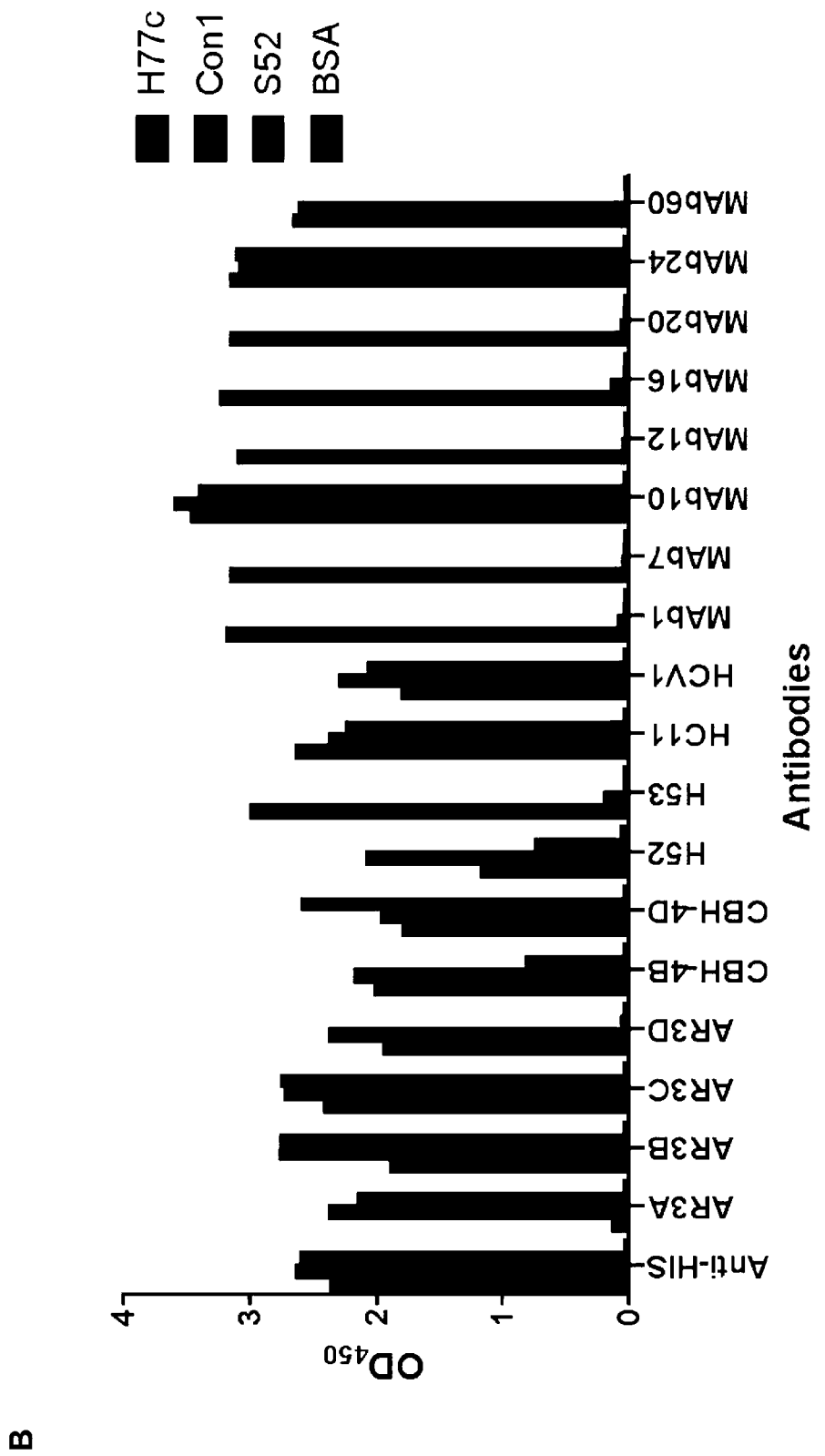

Δ123 from any genotype should be equally able to elicit bNAbs as it comprises the most conserved regions of E2. However, the expression profile of WT E2 and Δ123 will vary between different genotypes. To determine whether Con1 Δ123 and/or S52 Δ123 express higher yields of HMW species, affinity-purified Δ123 glycoproteins from transient transfections into FS293F cells were analysed by gel filtration chromatography on a Superdex 200 prep grade 16/600 column using the ÄKTA FPLC system. Quantification of the area under the peaks using the UNICORN software revealed that both the Con1 (FIG. 3B) and S52 (FIG. 3C) strains indeed generated higher yields of HMW Δ123, with 46.02% (Con1) and 44.88% (S52) of all Δ123 glycoproteins generated of the HMW form (HMW1 and HMW2 combined) compared to 23.13% for H77c (Table 6).

To assess the reproducibility of these results, transient transfections and purification of Δ123 were repeated, and gel filtration chromatography was again performed to analyse Δ123 expression. On the second round, the expression level of Con1 Δ123 was approximately double that of round 1 while that of S52 Δ123 remained relatively stable, as shown by the scale on the y-axes (FIG. 3D-E). Despite the variation in expression levels, it was important to note that the expression profiles of Con1 and S52 Δ123 remained similar for both round 1 and round 2. In comparison to H77c, an improvement in the yield of HMW Δ123 was again observed, with similar proportions of HMW species generated on the second round-46.98% and 41.56% for Con1 and S52, respectively (Table 6).

Gel filtration fractionated Δ123 glycoproteins were analysed via SDS-PAGE. Non-reducing SDS-PAGE on 5-12% polyacrylamide gradient gels corroborated the findings from gel filtration chromatography, again demonstrating that Δ123 exists as a variety of disulfide linked oligomeric forms and displaying an inversely proportional relationship between band intensity and molecular weight (FIG. 4A-B). Reducing SDS-PAGE analyses were also conducted on 12% acrylamide gels using β-mercaptoethanol, a reducing agent that disrupts disulfide bonding, which in turn also disrupts hydrophobic contacts. Results reveal that disulfide bonds are indispensable for the formation and stabilisation of higher order structures as these all migrated as monomers once their disulfides were cleaved by β-mercaptoethanol (FIG. 4C-D). Hydrophobic interactions may contribute to the formation of higher order species.

These data reveal that the Con1 and S52 strains indeed express higher yields of HMW Δ123 compared to H77c and demonstrates one possible method to improve HMW Δ123 production.

Example 10: Antigenic Characterisation of HMW Δ123

To assess whether HMW Δ123 generated by the Con1 and S52 strains recapitulate the antigenic pattern of that of H77c, gel filtration fractionated monomeric and HMW1 Δ123 from all three strains were tested against a panel of conformation sensitive and insensitive MAbs in an ELISA format (FIG. 5A). Single dilution point assessments (FIG. 5B) were initially performed as a rapid test to determine which MAbs exhibit positive reactivity towards Δ123 of H77c and either or both of Con1 and S52, thereby allowing the antigenicity between strains to be compared. The MAbs that fulfilled this criterion were further tested in direct ELISAs, whereby half-logarithmic serial dilutions of the MAbs were applied to enzyme immunoassay plates coated separately with monomeric and HMW1 Δ123, followed by detection with the appropriate HRP-conjugated secondary antibodies. Relative binding of each MAb towards HMW1 4123 were then calculated by comparing the mid-point of each binding curve (Table 7), which was taken as half of the highest optical density value.

While single dilution point assessments show that conformation sensitive mouse H53 and MAbs 1, 7, 12, 16 and 20 all exhibited positive reactivity towards H77c Δ123, negligible reactivity towards Con1 and S52 Δ123 was demonstrated, indicating that the epitope integrity of these two strains were altered in a way that rendered the target epitopes of these MAbs unrecognisable, and that these MAbs are type-specific. The contrary was displayed by conformation sensitive human AR3A, where there was positive reactivity towards Con1 and S52 Δ123, but not for H77c (FIG. 5B).

Out of the 11 MAbs that were further tested in direct ELISAs, 8 (AR3B, AR3C, AR3D, CBH-4B, CBH-4D, HC-11, MAbs 10 and 60) showed reduced binding to the HMW form of Δ123 when compared to the monomeric form (Table 7), indicating that their target epitopes were more occluded. Only mouse H52 demonstrated a markedly enhanced ability to bind HMW1 Δ123 for all three strains (Table 7), suggesting improved access to the residue C652.

When comparing the ability of each MAb to bind the HMW forms of Con1 and S52 to that of H77c, 5 (HCV1, AR3B, AR3C, CBH-4D, HC-11) out of the 11 MAbs tested exhibited increased or equivalent levels of binding. Increased binding was also demonstrated by AR3D and H52, but only towards Con1 Δ123, while MAbs 10 and 24 exhibited reduced levels of binding towards both strains (Table 7).

Example 11: Reduction and Refolding of Δ123 Using TCEP and BMOE

The ability to refold Δ123 monomers into monomers by partially reducing monomeric Δ123 to generate free sulfhydryls, followed by re-conjugation of these sulfhydryls into intermolecular disulfide bonds that will mediate multimer formation was assessed.

Small scale reduction of Δ123 using TCEP, a sulfhydryl-free reducing agent, was trialed as a rapid test to determine the optimal concentrations of TCEP required for partial reduction of Δ123 (FIG. 6). This was executed by exposing monomeric H77c Δ123 coated onto an enzyme immunoassay plate, to different concentrations of TCEP (0-500 mM) for 30 min at 37° C., allowing time for the reduction to occur. To determine the extent of structural change resulting from TCEP reduction, a single dilution of the conformation-dependent mouse H53 antibody was applied to the plate, and binding detected with HRP-conjugated anti-mouse antibodies. H77c Δ123 treated with 10-500 mM TCEP exhibited progressively reduced binding to H53, with all optical density values greater than that of the R04 negative control (a human MAb against the human cytomegalovirus). These results show that the conformation of Δ123 was not entirely destroyed as H53 recognition was retained to a degree, indicating that partial reduction was achieved and that reduction was progressively increased with increasing TCEP concentration. Furthermore, positive anti-HIS binding occurred consistently in the presence of different concentrations of TCEP, eliminating the possibility that loss of bound Δ123 could account for reduced H53 binding. Since retention of Δ123 conformation was considered necessary to preserve the antigenic and immunogenic properties of Δ123 and to allow subsequent reformation into HMW Δ123, it was determined that TCEP concentrations between 10-200 mM were suitable for further protein reduction experiments.

Reduction on enzyme immunoassay plate-bound proteins allows rapid testing of numerous reagent concentrations. However, reduction in solution is more appropriate in terms of potential vaccine production. Therefore, H77c Δ123 monomers were prepared in PBS pH 6.8 as TCEP is most effective at a pH range of 6 to 8. Various concentrations of Δ123 were also prepared to investigate whether different amounts of proteins initially present would affect the efficiency of conversion of monomer to HMW forms. TCEP was then added at concentrations guided by the previous small scale reduction experiment. To subsequently transform partially reduced Δ123 monomers into HMW Δ123, reduction was followed by protein refolding, a process that involves disulfide reformation and reshuffling. This was facilitated through the addition of BMOE, a short homobifunctional, maleimide crosslinker that forms thioether bonds with free sulfhydryls at a pH range of 6.5 to 7.5. Sulfhydryl groups are conjugated as a result, thus mimicking disulfide reformation. Furthermore, TCEP is sulfhydryl-free and is thus appropriate for use in conjunction with sulfhydryl-reactive BMOE crosslinkers, justifying the use of TCEP as a reducing agent in this experiment. Refolded Δ123 glycoproteins were analysed via non-reducing SDS-PAGE (FIG. 6B). All samples displayed similar migration patterns to the monomer control and the mock control, which was also subjected to the reduction and refolding procedure but in the absence of TCEP and BMOE (lane 7 on FIG. 6B and Table 8). No bands aligned with that of the HMW Δ123 control, revealing that TCEP reduction and refolding using BMOE were unsuccessful at converting monomeric Δ123 to HMW Δ123.

Example 12: Reduction and Refolding Using the Redox-Shuffling System

The redox-shuffling system was utilised to promote oxidation between reduced sulfhydryls, whereby reduction and refolding was conducted simultaneously in the presence of both a reducing agent (GSH) and an oxidising agent (GSSG). This was carried out by preparing H77c Δ123 monomers in carbonate-bicarbonate buffer pH 9.6 as a high pH environment promotes the reducing and oxidising ability of GSH and GSSG, respectively. To investigate the effect of protein concentration on aggregation efficiency, H77c Δ123 monomers were also prepared at various concentrations (Table 9). A ratio of 5 GSH: 1 GSSG was then added, equating to a final concentration of 2 mM GSH and 0.4 mM GSSG, which are the concentrations typically used in commercial protein refolding kits and have been reported to refold >90% of proteins (information provided by Thermo Fisher Scientific). These Δ123 samples were then incubated at 37° C. for various lengths of time (Table 9), which was immediately followed by a 50 fold dilution with PBS pH 6.8 and removal of glutathione using centrifugal filter units to stop the reaction.

Δ123 samples were analysed via non-reducing SDS-PAGE (FIG. 7A), which revealed successful refolding of monomeric Δ123 into dimeric Δ123 and higher order species, as shown by the appearance of dimer bands and the presence of higher order structures greater in size than a dimer. The monomer and mock controls each produced a band corresponding to the size of monomeric Δ123 as expected. However, a faint dimer band was also observed for the mock control (lane 1 on FIG. 7A). This is consistent with the gel filtration profile for monomeric Δ123 (FIG. 7B), which also displayed a small amount of contaminating dimeric Δ123. The detection of dimers may also suggest spontaneous protein aggregation as a result of exposure to air or higher temperatures as untreated Δ123 monomers were previously stored in capped tubes at 4° C. Additionally, boiling samples prior to loading onto gels can promote aggregation. Quantification of the monomer and dimer band densitometries using the LI-COR Odyssey system showed that the mock control contains 4.65 fold more monomer than dimer. The majority of monomers failed to refold into higher order species when 1 μg/μL of monomeric Δ123 was treated with glutathione, with 6.89 fold more monomer than dimer, higher than recorded for the mock control. In contrast, the use of higher concentrations (5 and 10 μg/μL) resulted in more dimer formation, indicating that refolding in the presence of high amounts of proteins enhanced Δ123 aggregation efficiency. Increasing the incubation time from 2 h to 24 h also induced the formation of more dimers, demonstrated by juxtaposing conditions 3 and 5 on FIG. 7A. Out of all the tested conditions, conversion of monomers into dimers was most efficient when 10 μg/μL of monomeric Δ123 were subjected to glutathione treatment for 24 h. Therefore, a scaled up repeat of the experiment utilising these conditions was performed and analysed by gel filtration chromatography.

The gel filtration profile of Δ123 from the repeat experiment displayed a monomer and dimer peak (FIG. 7C), consistent with results from non-reducing SDS-PAGE (FIG. 7A). A shoulder on the dimer peak was also observed, indicating some formation of higher order species. Quantification of the area under the curve using the UNICORN software revealed that virtually half of the Δ123 monomers were refolded into multimers, with dimers comprising the majority of protein (Table 10). Altogether, these results demonstrated that use of the redox-shuffling system indeed led to intermolecular disulfide bond formation between glutathione-reduced Δ123 monomers. Predominantly these experiments resulted in the formation of dimers.

Example 13: Reduction Using Dithiothreitol (DTT) and Refolding Via Slow Dilution To expand our investigations on Δ123 aggregation, a different reducing agent and refolding technique was employed: DTT and slow dilution, respectively. As with TCEP, small scale DTT reduction of Δ123 in an ELISA format was initially trialed to determine the optimal DTT concentrations required to achieve partial reduction of Δ123 (FIG. 8A). This was executed by exposing H77c Δ123 monomers, coated onto an enzyme immunoassay plate, to different concentrations of DTT (0-10 mM) for 30 min at 37° C. The plate was then washed to remove DTT, thereby stopping further reduction, followed by blocking, addition of the primary antibodies (anti-HIS, H53 and R04) and detection with the appropriate HRP-conjugated secondary antibodies. Virtually complete reduction of Δ123 was achieved with >2 mM DTT. Δ123 treated with 0.1-1.0 mM DTT exhibited progressively reduced H53 binding and therefore, these concentrations were further investigated in subsequent DTT reduction experiments. Consistent anti-HIS binding was observed at all DTT concentrations, eliminating loss of bound Δ123 as a factor for reduced H53 binding.

DTT reduction in solution was then investigated, whereby various concentrations of H77c Δ123 monomers (Table 11) were prepared in carbonate-bicarbonate buffer pH 9.6 and exposed to DTT, which retains its reducing capacity at a pH of >7. Reduced sulfhydryls will eventually undergo spontaneous oxidation in the absence of a reducing agent, leading to reformation of disulfide bonds. To allow this process to occur, reduced Δ123 glycoproteins were subsequently subjected to refolding by means of slow dilution, which involves stepwise additions of PBS pH 6.8 to the Δ123 samples. Furthermore, this procedure dilutes DTT and attenuates its activity by gradually neutralising the pH environment, thereby promoting oxidation of sulfhydryls.

Refolded Δ123 glycoproteins were analysed via non-reducing SDS-PAGE (FIG. 8B). The mock control produced a monomer band as expected, and a faint band at approximately 100 kDa corresponding to dimeric Δ123, indicating low level contamination with dimers or perhaps spontaneous protein aggregation as a dimer band was not observed in the monomer control. Quantification of the monomer and dimer band densitometries showed that the mock control contains 3.41 fold more monomeric protein than dimeric protein (lane 1 on FIG. 8B and Table 11). An increased amount of oligomer was recorded for Δ123 samples subjected to reduction and refolding under all test conditions (FIG. 8B), revealing that proportions of Δ123 monomers were indeed converted into multimers as a result of successful intermolecular disulfide bond formation. A significant drop in the ratio of monomers vs. dimers was recorded for samples incubated for 30 min following DTT addition, which resulted in less than 2 fold more monomeric than dimeric protein. Extending the incubation period failed to enhance Δ123 aggregation as ≥2 h incubations did not give rise to more multimer formation compared to 30 min incubations. Low monomer to dimer ratios were recorded when 1 μg/μL of monomeric Δ123 was treated with DTT, contrasting with the results from glutathione treatment. The lowest value of 1.33 was recorded when 1 μg/μl of monomeric Δ123 was treated with 0.1 mM DTT for 30 min (lane 11 on FIG. 8B and Table 11), indicating that conversion into dimers was most efficient using these conditions. Formation of higher order species was most apparent on non-reducing SDS-PAGE when 1 μg/μL of monomeric Δ123 was treated with 1 mM DTT for 30 min (lane 9 on FIG. 8B).

A scaled up repeat experiment was performed using the optimal conditions for multimer formation (1 mM DTT for 30 min). The refolded Δ123 glycoproteins were then analysed by gel filtration chromatography to corroborate observations on non-reducing SDS-PAGE and to obtain more accurate measurements of each of the oligomeric species produced (FIG. 8C-D). A proportion of monomers were unaffected as shown by retention of the monomer peak after DTT treatment. The gel filtration profile also indicated some formation of dimeric Δ123 as a small amount of the protein eluted within the area that corresponds to dimeric Δ123, which is more prominent than that of the gel filtration profile before treatment. Most importantly, a broad peak corresponding to sizes of over 200 kDa eluted at approximately 59 min, similar to the elution time observed for HMW2

Δ123, verifying successful Δ123 aggregation into larger multimers. Quantification of the area under the peaks revealed that approximately a fifth of the monomers aggregated into HMW 4123. DTT reduction followed by slow dilution was most effective out of the three methods employed to convert monomeric Δ123 into HMW Δ123.

Example 14: Analyzing the Size of the Product Generated from Refolding DTT-Treated Δ123

The following protocol was used analyse the size of the products generated from refolding DTT-treated Δ123.
Materials:
Monomeric Δ123
Carbonate-bicarbonate buffer pH 9.6
Dithiothreitol (DTT)
Phosphate buffered saline (PBS) pH 6.8
To reduce monomeric Δ123 1 mg of monomeric Δ123 was prepared in carbonate-bicarbonate buffer to a total volume of 1 mL in a 5 mL yellow capped tube. If refolding in the presence of protease inhibitors, 5 μg/mL aprotinin, 8 μg/mL leupeptin and 5 μM kifeunensine were also added. DTT was dissolved in Milli-Q water and was added to the tube at a final concentration of 0.3 mM (i.e. 3 μL of 100 mM DTT). Next, the mixture was incubated at 37° C. for 30 min. For two treatments of DTT, after incubation 3 μL of 100 mM DTT was added to the tube and the mixture incubated at 37° C. for 30 min. For three treatments of DTT, after the second incubation 3 uL of 100 mM DTT was added to the tube and the mixture incubated again at 37° C. for 30 min.

For refolding, 0.5 mL PBS was added and the proteins were incubated at room temperature for 15 min. This step was repeated three times. DTT was removed by using Amicon Ultra centrifugal filter units (10k MWCO) and proteins were rinsed twice in PBS.

For size analysis, proteins were transferred into a 1.5 mL Eppendorf tube and centrifuged at 13,000 rpm at 4° C. for 10 min. Gel filtration chromatography was then performed using a 16/600 Superdex 200 prep grade column.

Figure 10:
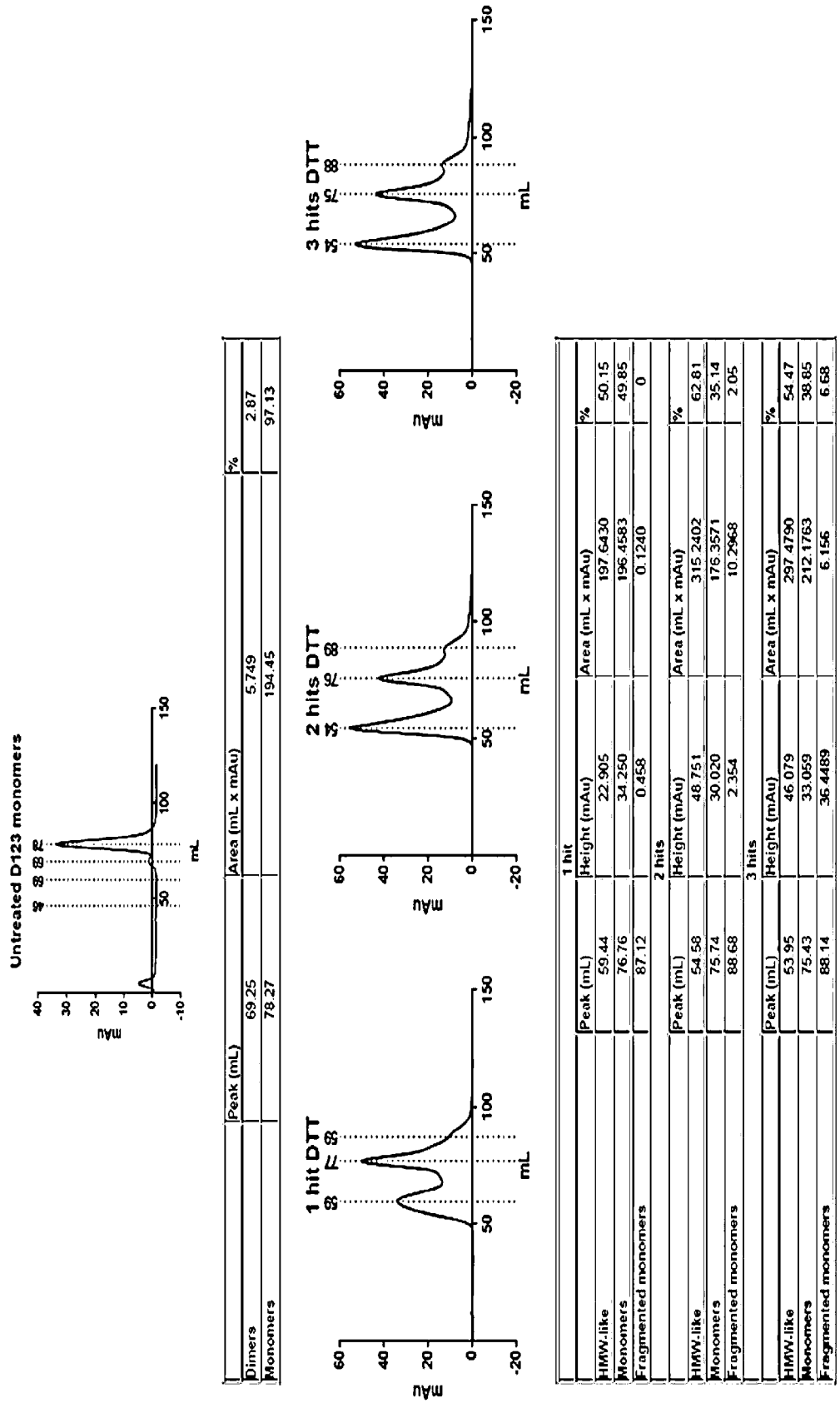
FIG. 10 shows the analysis of products generated from refolding DTT-treated Δ123 using gel filtration chromatography. The profile of untreated monomers is shown, followed by increasing numbers of treatments (1, 2, or 3 hits) with DTT as described in Example 14.

DTT treatment revealed that monomeric Δ123 could refold into higher order species, forming peaks at elution times of 59 and 54 min (FIG. 10). Increasing the number of DTT treatments resulted in a shift of the HMW-like peak to the left; from an elution time of 59 min observed in 1 hit to 54 min after 2 or 3 hits (FIG. 10). Meanwhile, a slight shift to the right was observed for the monomer peak; from an elution time of 77 to 76 to 75 for 1, 2 and 3 hit/s, respectively. Addition of protease inhibitors resulted in the elution of the residual monomer peak at 75 min (FIG. 11, bottom example) and the refolded multimer eluted at 54 min suggesting that protease inhibitors may be beneficial in this process.

To examine whether residual non-refolded monomeric protein was able to be refolded, the residual monomeric species from the examples described above treated with two DTT treatments (pooled gel filtration fractions 72-81 and concentrated using Amicon Ultra centrifugal filter units (10k MWCO) were collected. The samples were retreated as described above twice with DTT, performing refolding and subjecting the proteins to size analysis.

Refolding non-refolded monomeric Δ123 (FIG. 11, top example) resulted in 37% dimer formation and little HMW-like formation, while 63% remained as monomers, indicating that a sub-population of Δ123 monomers are recalcitrant to refolding. The formation of a relatively short peak to the right of the monomer peak was also noted. However, refolding in the presence of protease inhibitors resulted in a reduction to the size of this peak.

The results demonstrate yields of at least 60-70% oligomer (>100 MW or 200MW) can be produced using the present methods.

Example 15: Antigenicity Characterization of DTT-treated Δ123 and ALA7 Δ123

The following protocol was used to compare the antigenicity between DTT-treated Δ123 and ALA7 Δ123 using a panel of the below described antibodies.
Materials:
Reagents:
  Carbonate-bicarbonate buffer pH 9.4
  ELISA wash (PBST)
  ELISA Hydrogen peroxide block (BSA10PBS)
  ELISA diluent (BSA5PBST).
  Phosphate citrate buffer; 3,3',5,5'-Tetramethylbenzidine (TMB)
  Hydrochloric acid (HCl).
Proteins:
  HMW1 Δ123
  Monomeric Δ123 before refolding
  Refolding-resistant Δ123
  Refolded multimericΔ123
  Monomeric ALA7 Δ123 before refolding
  Refolding-resistant ALA7 Δ123
  Refolded multimeric ALA7 Δ123
  BSA
Antibodies:
  Primary antibodies AR3C, CBH4G, HC84.27, HCV1
  Secondary antibodies anti-human HRP conjugated Nunc Maxisorb flat-bottom 96 well plate was coated with 5 μg/mL of the above listed proteins prepared in 50 mM carbonate-bicarbonate buffer pH9.6 and incubated overnight (o/n) at 4° C. The following day the plates were washed 4× with PBST and blocked with 100 μL/well BSA10PBS for 1 h at RT. Next, the plates were washed 4× with PBST and performed half-logarithmic serial dilutions of the 1° antibodies listed in materials and incubated for 1 h at RT. Next, the plates were washed 4× with PBST and added 50 μL/well of the 2° antibodies listed in materials and incubated for 1 h at RT. Next, the plates were washed 4× with PBST and developed with 100 μL/well TMB, followed by the addition of 50 μL/well HCl. Results are as shown in FIG. 9. Refolded Δ123 had reduced binding to AR3C and CBH4G compared to the monomeric Δ123 control and the refolding resistant Δ123 control indicating that target epitopes were more occluded in refolded Δ123, a profile typical of HMW Δ123. Refolded ALA7 Δ123 had reduced binding to AR3C and CBH4G compared to the monomeric ALA7 Δ123 control and the refolding resistant ALA7 Δ123 control indicating that target epitopes were more occluded in refolded ALA7 Δ123, a profile typical of a high molecular weight form of the protein. The decreased reactivity of CBH4G to refolded Δ123 and refolded ALA7Δ123 may indicate that non-neutralizing epitopes are more occluded in the refolded material than in the native HMW material. This may provide an advantage when refolded material is used as an immunogen as it is likely that the generation of non-neutralizing antibody responses will be suppressed.

Example 16: Refolding Experiments

The results of further refolding experiments conducted above are summarized in Tables 13 and 14.

In summary, gel filtration chromatography of affinity-purified Δ123 reveals the presence of a heterogeneous mixture of disulfide linked dimers and higher order HMW multimers in addition to the predominant monomeric form. HMW Δ123 is an attractive vaccine candidate. However, the attractiveness of HMW forms of Δ123 is somewhat mitigated by the relatively low yields of expression and the presence of contaminating proteins. Several methods to improve the yield of HMW Δ123 production which would be beneficial for vaccine manufacture were investigated.

Expression of Δ123 from transient transfections in human-derived FS293F cells was assessed and verified successful Δ123 production and purification through sandwich ELISA, utilising CD81-LEL 113-201 to capture Δ123.

Results obtained from gel filtration chromatography reveal that both the Con1 and S52 strains consistently expressed higher proportions of HMW Δ123, with approximately a 23% and 20% increase for Con1 and S52 respectively, virtually doubling the proportions of HMW Δ123 generated by the H77c strain. Furthermore, these results reveal that different HCV strains produce varying amounts of HMW Δ123. Results were reproducible for both Con1 and S52 Δ123 generated from a second independent round of transfection and purification.

Although affinity chromatography using cobalt-charged TALON beads efficiently purifies secreted Δ123 glycoproteins from cell culture supernatants, cobalt leaching from these beads can cause health issues when used for vaccine production. A safer alternative could be the use of antibody affinity chromatography when purifying Δ123

Although the structure of HMW Δ123 remains undefined, the results described herein suggests that intermolecular disulfide bonds mediate a unique folding arrangement that occludes non- and type-specific neutralising regions that were previously accessible in WT E2 and monomeric Δ123. An immunogenicity study of H77c Δ123 supports this by demonstrating that while monomers failed to generate bNAbs, the HMW form was able to elicit antibodies that could neutralise all 7 HCV genotypes, indicating that these antibody responses were directed away from non-neutralising epitopes by occlusion of these regions, and thus targeted to broadly neutralising epitopes instead (H. Drummer, unpublished data).

Since monomers can be efficiently produced and effectively purified from a heterogeneous mixture of different Δ123 species, strategies were assessed for refolding monomeric Δ123 into HMW forms. It was hypothesised that partial reduction of monomers to generate free sulfhydryls, followed by conjugation or re-oxidation of these sulfhydryls will lead to reshuffling of disulfide bonds in a way that recapitulates the disulfide arrangement in H77c HMW Δ123. Conventionally, reduction and refolding methods are employed to regenerate lower order species (monomers/dimers/trimers) from undesirable protein aggregates, especially from bacterial inclusion bodies (Singh and Panda, 2005).

Homobifunctional BMOE crosslinkers react to free sulfhydryls, resulting in their conjugation. Furthermore, if conjugation occurs between individual Δ123 subunits, intermolecular interactions that mediate aggregation into HMW Δ123 will be established. However, the utilisation of BMOE crosslinkers in the refolding process failed to promote intermolecular disulfide bond formation. This suggests that BMOE did not crosslink Δ123 monomers for the conditions that were trialed, perhaps due to steric hindrance or experimental errors. Furthermore, the absence of a BMOE-treated positive control rendered it extremely difficult to assess the effectiveness of these BMOE refolding experiments. This is not to say that other cross-linking agents will not generate cross-linked multimers and will not be a useful method for their production. Conversely, DTT reduction followed by the slow dilution method, as well as use of the glutathione-based redox-shuffling system resulted in the formation of dimers and higher order species, indicating that free sulfhydryls were oxidised into intermolecular disulfide bonds. Specifically, sulfhydryls at cysteine residues 452, 486, 569 and 597 may be directly involved in bridging individual Δ123 subunits together, as these residues are non-essential to the structural integrity of the E2 RBD.

Reduction using DTT and refolding via slow dilution were most effective method at converting monomeric Δ123 into HMW species out of the three methods trialed. This method allowed the conversion of approximately a fifth of Δ123 monomers into HMW species. Use of the redox-shuffling system achieved refolding in approximately 50% of Δ123 monomers, albeit to dimers.

Example 17: Reduction and Assembly Using Beta-Mercaptoethanol (BME)

Reduction of Δ123 monomers by partial reduction using BME and assembly into high molecular weight oligomers was assessed.

Monomeric Δ123 (20 μg) was prepared in PBS to a total volume of 20 μL in each tube. BME was added such that the final concentrations of 0-100 mM and incubated for 15 min at RT. To reassemble the proteins, 10 μL of PBS was added and the proteins were incubated at RT for 7 min and repeated twice. BME was removed by using Amicon Ultra centrifugal filter units (30k MWCO) and proteins were rinsed twice in PBS. Proteins were analysed in non-reducing SDS-PAGE. Samples of BME-treated Δ12341233 and HMW1 Δ123 and 2 μL of protein standards were separately loaded into the wells, and then gel electrophoresis performed at 120V. Once the dye front had migrated to the top of the separation gel, the voltage was increased to 160V. The gel was stained with Coomassie (0.25% Coomassic Brilliant Blue G-250, 50% methanol and 10% acetic acid) for 1 h, then destained (50% methanol and 10% acetic acid) until the background of the gel turned clear. Finally, the gel was viewed using the Li-CorOdyssey imaging system.

Treated and untreated proteins were analysed in SDS-PAGE under non-reducing conditions. The results (FIG. 15A) show that untreated monomeric Δ123 mostly migrates as a monomer, with a small amount of dimer present, likely a result of boiling samples before addition to SDS-PAGE. At high concentrations of BME, larger HMW oligomers can be observed as indicated in FIG. 15A. To confirm their presence, Δ123 monomers were reduced with 100 mM BME and assembled before analysis on gel filtration chromatography. The results (FIG. 15B) show that a small shoulder was present on the Δ123 monomers treated with 100 mM BME as indicated by the shaded area. This suggests that BME can reassemble Δ123 into higher order oligomers, albeit inefficiently.

Example 18: Immunogenicity of Assembled Glycoproteins

To determine whether the assembled proteins were more immunogenic in animals compared to monomeric antigens, outbred guinea pigs were vaccinated with 100 μg protein four times, three weeks apart using Addavax as an adjuvant (Table 15). Guinea pigs were bled two weeks after their final vaccination and immune serum analysed to determine antibody titres towards Δ123 monomeric protein.

Nunc MaxiSorp flat-bottom 96 well plates were coated with 5 μg/mL of monomeric H77c E2 Δ123 prepared in 50 μL/well 50 mM carbonate-bicarbonate buffer pH 9.6 and incubated overnight at 4° C. The next day, plates were washed 4× with PBST and blocked with 100 μL/well BSA10PBS for 1 h at RT. After washing 4× with PBST, serial half-logarithmic dilutions of guinea pig serum starting at 1/100 were added to plates for 2 hours at room temperature. Plates were washed 4 times with PBST and anti-HIS Antibody at 1/1000 added and incubated for 1 h at RT. Plates were washed 4× with PBST and developed with 100 L/well TMB, followed by the addition of 50 μL/well HCl. Optical density at 450 nm-650 nm was plotted (y-axis) against the serial dilution and the reciprocal dilution required to give an optical density of 0.5 units was used to determine the antibody titre. As groups 4-F and 5-F had four animals each, both receiving monomeric versions of HCV proteins, the results from these groups were combined for comparison with other groups.

The results show that animals vaccinated with refolded Δ123 and 4123A7 protein generated higher antibody titres than animals vaccinated with monomeric forms of these proteins (Δ123-41826, Δ123A7=28686 versus 21756 for the combined Δ123 and Δ123A7 monomer group (FIG. 16). Mean titres for these groups were also higher. In the case of the assembled Δ123 group, the geometric mean antibody titre was higher than the native Δ123 HMW vaccinated group (Table 16). Animals receiving assembled Δ123 had statistically significantly higher antibody titres than animals that received monomeric antigens (p=0.0286) (FIG. 16).

Example 19: Specificity of the Antibody Response

To determine whether the assembled antigens generated different specificities of antibodies, sera were tested against a synthetic peptide representing a major antigenic areas of the E2 glycoprotein that is a target of broadly neutralizing antibodies that prevent infection with HCV. Epitope I spans residues 412-423 and encompasses the epitope of broadly neutralizing antibodies such as mouse AP33 (Owsianka et al., 2001; Owsianka et al., 2005; Tarr et al., 2006); rat 3/11 (Tarr et al., 2006; Flint et al 2009); human HCV1 and 95-2 (Broering et al 2009); human HC33.1 and related antibodies (Keck et al., 2013); H77.39 (Sabo et al., 2011); MRCT10.v362 and hu5B3.v3 (Pantua et al., 2013); and MAb24 (Alhammad et al., 2015). A synthetic peptide was used to detect such specificities and spanned residues 408-428 and has been previously used to characterise polyclonal antibody reactivity in guinea pig serum (Vietheer et al., 2017).

Nunc MaxiSorp flat-bottom 96 well plates were coated with 5 μg/mL of H77c epitope I peptide (408-428) prepared in 50 μL/well 50 mM carbonate-bicarbonate buffer pH9.6 and incubated o/n at 4° C. The next day, the plates were washed 4× with PBST and blocked with 100 μL/well BSA10PBS for 1 h at RT. After washing 4× with PBST, half-logarithmic serial dilutions of guinea pig sera were added starting at 1/5 and allowed to bind for 1 h. After 4× washing with PBST, 50 μL/well of anti-guinea pig HRP antibody was added and incubated for 1 h at RT. Plates were washed 4× with PBST and developed with 100 μL/well TMB, followed by the addition of 50 μL/well HCl.

The results show that animals vaccinated with assembled Δ123 and Δ123A7 had significantly higher titres of antibody than animals vaccinated with monomeric forms of these antigens (FIG. 17). In the case of assembled Δ123, mean titres were 15 times higher than the monomeric group and 1.15 times higher than the native Δ123 vaccinated group. In the case of assembled 4123A7 mean titres were 5 times high than the monomeric group. The data suggest that assembling antigens from a natively folded state which, in this example, was a monomer of HCV E2 into a higher order oligomer significantly improved the immunogenicity of the antigen by increasing titres of antibodies directed to broadly neutralizing antibody epitopes.

Example 20: Specificity of the Antibody Response-Epitope III

To determine whether the assembled antigens generated different specificities of antibodies, sera were tested against a synthetic peptide representing the CD81 binding loop spanning residues 523-549. This antigenic region comprises part of antigenic region 3 and is a target for neutralizing antibodies.

Nunc MaxiSorp flat-bottom 96 well plates were coated with 5 μg/mL of H77c epitope III peptide (523-549) prepared in 50 μL/well 50 mM carbonate-bicarbonate buffer pH9.6 and incubated o/n at 4° C. The next day, the plates were washed 4× with PBST and blocked with 100 μL/well BSA10PBS for 1 h at RT. After washing 4× with PBST, half-logarithmic serial dilutions of guinea pig sera were added starting at 1/5 and allowed to bind for 1 h. After 4× washing with PBST, 50 μL/well of anti-guinea pig HRP antibody was added and incubated for 1 h at RT. Plates were washed 4× with PBST and developed with 100 μL/well TMB, followed by the addition of 50 μL/well HCl.

The results (FIG. 18) show that animals that received assembled Δ123 and 4123A7 generated high titres of antibodies to H77c epitope III with the mean and geometric mean of animals vaccinated with Δ123 being higher than those receiving the natively folded monomeric material (Table 18). In addition, antibody titres in animals that receiving the assembled Δ123 and Δ123A7 protein were consistently high as opposed to the wide spread in antibody titres observed in animals receiving the monomeric material 5-6 fold range in titres for Δ123 and Δ123A7 versus 200 fold for monomer). This suggests that the assembled proteins were able to induce a consistent immune response in vaccinated animals, whereas the monomeric starting material inconsistently generated antibodies specific to this region.

Example 21: Cross Reactivity of Antibody Responses to Epitope I

To determine if the antibodies generated to H77c epitope I were cross-reactive with the equivalent sequence of a different genotype, an ELISA was performed using the genotype 2a J6 peptide spanning residues 408-428.

Nunc MaxiSorp flat-bottom 96 well plates were coated with 5 μg/mL of J6 epitope I peptide prepared in 50 μL/well 50 mM carbonate-bicarbonate buffer pH9.6 and incubated o/n at 4° C. The next day, the plates were washed 4× with PBST and blocked with 100 μL/well BSAnoPBS for 1 h at RT. After washing 4× with PBST, half-logarithmic serial dilutions of guinea pig sera were added starting at 1/5 and allowed to bind for 1 h. After 4× washing with PBST, 50 μL/well of anti-guinea pig HRP antibody was added and incubated for 1 h at RT. Plates were washed 4× with PBST and developed with 100 μL/well TMB, followed by the addition of 50 μL/well HCl.

The results (FIG. 19) show that antibodies generated in animals vaccinated with Δ123 and Δ123A7 were cross-reactive with the genotype 2a strain J6 sequence of epitope I and the mean and geometric mean titres of antibodies in these groups was higher than those achieved by vaccination with the native monomeric form of these antigens (Table 19). The mean antibody titre of animals vaccinated with Δ123 were almost 2-fold higher than those achieved through vaccination with the native high molecular weight form of Δ123 harvested directly from 293 FS cells transfected with plasmids that express the Δ123 protein (Table 19).

Example 22: Characterization of HCV E2 CD81 Inhibition

HCV E2 attaches to cells using the cellular receptor CD81. In our laboratory we have previously employed an assay to determine the ability of antibodies present in immune serum to prevent binding of soluble E2 to recombinant CD81.

Nunc MaxiSorp flat-bottom plates were coated with 5 μg/mL MBP-CD81LEL prepared in 50 mM carbonate-bicarbonate buffer pH 9.6 and stored at 4° C. o/n. The next day, plates were blocked with 100 μL/well BSA10PBS for 1 h and washed ×4 in PBST. 50 μL of serial half-logarithmic dilutions of guinea pig immune serum starting at 1/5 in BSAsPBST was added to 50 μL of unfractionated E2 RBD (G1a H77c and G2a JFH1 separately) at 1 μg/mL to all wells then incubated for 1 h at RT. 80 μL of the E2 RBD-sera mix was added to CD81-coated plates and incubated 4° C. o/n. Plates were washed 4× with PRST before addition of 50 μL/well mouse anti-HIS at 1/500 and incubated for 1 h at RT. Plates were washed 4× with PBST and developed with 100 μL/well TMB and reactions stopped with addition of 50 μL/well 1M HCl. The results show that animals vaccinated with assembled Δ123 and Δ123A7 generated high titres of antibodies able to prevent the interaction between H77c G1a E2 and CD81 and were present at similar levels to those present in mice that received the native Δ123 HMW protein and similar to the mean levels achieved in mice vaccinated with monomeric forms of these antigens (FIG. 20A and Table 20).

The ability of the immune serum to inhibit the binding of G2a E2 binding to CD81 was assessed (FIG. 20B). Antibody titres in animals vaccinated with assembled Δ123 and Δ123A7 were similar to animals vaccinated with the monomeric forms of these antigens and animals vaccinated with the native Δ123 HMW. These data suggest that assembled forms of Δ123 and Δ123A7 are more favourable at generating cross reactive antibodies that prevent heterologous genotypes of HCV binding to cell surface receptor CD81.

Example 23: Neutralization of Homologous Genotype 1a Virus

To determine if the antibodies generated resulted in the ability to prevent infection of liver cell lines with HCV, a neutralization assay was performed using homologous genotype 1a pseudotyped viruses.

Expression vectors for the production of HCVpp incorporating E1E2 heterodimers from G1a were pE1E2H77c (Drummer et al., 2003). pNL4-3.Luc.R-. E-(pNL43) was obtained from the NIH AIDS Reagent Program, Division of AIDS, NIAID, NIH from Dr. Nathaniel Landau (Connor et al., 1995; He et al., 1995). 6 μg of E1E2H77c DNA was mixed with 6 μg pNL. 43 DNA in a 1.5 mL Eppendorf tube. For the empty vector control, 1 μg pcDNA4c was mixed with 1 μg pNL43 DNA. 312 μL FuGENE 6 was added to 5200 μL Opti-MEM (+glutamax) then incubated at RT for 5 min and 600 μL of this mixture was added to the DNA mixtures. 100 μL was added to the empty control. These were incubated at RT for 20 min. In a PC3 laboratory, contents of the 8 tubes were added drop-wise to separate 293T cell-containing dishes from step 1. The empty control was added to one well of the 293T cell-containing plate from step 1. Fugene 6/Optimem/DNA mixtures were incubated at 37° C. and 5% $CO_2$ for 20 minutes before drop-wise addition to 293T cells. Cells were incubated at 37° C. in 5% $CO_2$ for 3 days. After 3 days, supernatant fluid containing infectious E1E2 pseudotyped viruses (HCVPP) or empty vector pseudotyped viruses (Emptypp) were removed and filtered through 0.45 uM filters ready for use in neutralization assays.

Half-logarithmic serial dilutions of heat inactivated guinea pig serum beginning at 1/20 were performed. 250 μL of the serum was added to 250 μL HCVpp and incubated for 1h. 150 μL/well of the sera-virus mixture was added to the Huh7.5 cells in triplicates. 150 μL/well of the empty control was added to the bottom row of a no antigen group plate in triplicate. Plates were then incubated at 37° C. and 5% $CO_2$.

42 h later media was removed from the Huh7.5 cells, which were then washed once in 1× PBS. 50 μL/well of 1× cell culture lysis reagent was added and cell lysates were transferred into u-bottom 96 well plates. 5 μL of lysate was transferred to 384 well white plates and read on a CLARIOstar plate reader. The average of triplicate values was plotted against the serum dilution, curve fitted using non-linear regression analysis and the reciprocal dilution of serum required to achieve a 50% inhibitory dose of virus infecting cells was calculated (Prism v7).

The results (FIG. 21) show that 8/8 animals vaccinated with assembled Δ123 and Δ123A7 generated antibodies able to prevent infection with G1a HCVpp. By contrast only 7/8 animals in the group that received monomeric antigen generated neutralizing antibodies. Mean and geometric mean antibody titres in the group that received Δ123A7 were higher than those achieved using monomeric antigen suggesting that increasing the size of the antigen through the method of assembly improves its immunogenicity (Table 22). Antibody neutralization titres achieved through assembly were in a similar range to those achieved using the native HMW form of the antigen (Table 22) suggesting that this method produces an antigen with at least an equivalent ability to generate neutralizing antibodies effective against the homologous strain of HCV and improved over the monomeric antigen.

Example 24: Ability of Immune Serum to Inhibit Binding of Human Monoclonal Antibodies to E2

To further interrogate the specificity of the antibody response in regard to whether the antibodies generated in guinea pigs recognise similar epitopes to those of known human broadly neutralizing antibodies a competitive enzyme immunoassay was performed.

Human antibodies HCV-1 (Broering et al., 2009), HC84-27 (Krey et al., 2013)], AR3C (Law et al., 2008) and 2A12 (Khan et al., 2014) were produced by synthesis of the VH and VL regions (Geneart) and cloning into pcDNA3-tPA-LC and pcDNA3-tPA-HC, respectively, for the expression of IgG1 under the direction of a tissue plasminogen activator (tPA) leader. Heavy and light chain encoding plasmids were transfected into FS293F cells for IgG production.

A constant amount of MAh and a half log dilution series of each guinea pig serum were simultaneously added to blocked wells and incubated for 2 hours at room temperature before addition to plate bound monomeric Δ123. Residual MAb binding was detected with anti-human Fab$_2$. Curves were fitted by non-linear regression and used to determine the ID50 for each serum sample. Where a serum sample failed to achieve an ID50 at the highest concentration tested (1:10 dilution, log 101) a value of log 100.5 was assigned to that serum.

The results show that animals vaccinated with assembled Δ123 and Δ123A7 had higher mean and geometric mean titres of antibodies that overlap with the epitope of the antibody HCV1 that recognises the 412-423 region (epitope I) (Table 23 and FIG. 22A). HCV1 antibodies have been shown to prevent and treat HCV in chimpanzees (Morin et al., 2012). In addition, the titres were similar to those achieved using native HMW Δ123 showing that this method produces an equivalent antigen. Antibody titres in animals receiving Δ123 were statistically higher than those in the monomeric vaccinated group (FIG. 22A).

The results show that compared to monomeric vaccines or native HMW vaccines, animals vaccinated with assembled Δ123 had higher mean and geometric mean titres of antibodies that overlap with the epitope of the antibody HC84-27 that recognises the 430-446 region of E2 and comprises part of the region in contact with cellular receptor CD81 (Table 24 and FIG. 22B). This antibody specificity is broadly neutralizing and prevents the generation of HCV escape mutants (Krey et al., 2013; Keck et al., 2012). This data shows that the assembly method produces an improved antigen with respect to generation of antibodies that overlap with the epitope recognised by HC84.27. Antibody titres in animals receiving Δ123 were statistically higher than those in the monomeric vaccinated group (FIG. 22B).

The results show that compared to monomeric vaccines, animals vaccinated with assembled Δ123 and Δ123A7 had higher mean and geometric mean titres of antibodies that overlap with the epitope of the antibody AR3C (Table 25 and FIG. 22C). In the case of Δ123, mean and geometric mean titres were higher than those generated with the equivalent native HMW antigen (Table 25).

The results show that compared to monomeric vaccines, animals vaccinated with assembled Δ123 and Δ123A7 had lower mean and geometric mean titres of antibodies able to prevent the binding of non-neutralizing antibody 2A12 (Table 26 and FIG. 22D). The data suggest that assembly of monomeric Δ123 and 4123A7 occludes non-neutralizing epitopes that have been shown to obstruct neutralization of HCV (Zhang et al., 2009) and the generation of neutralizing antibodies (Vietheer et al., 2017).

Example 25: Use of Assembled Proteins to Detect E2 Specific B cells

To determine if assembled HCV proteins can be used to identify immune cells with antibodies specific to an antigen, the following was performed using PBMCs isolated from a chronically infected person.

Enrichment of B Cells from Frozen PBMCs

Reagents

| | | |
|---|---|---|
| MiniMACS Separator | Miltenyi Biotec | Cat. # 130-042-102 |
| MACS MultiStand | Miltenyi Biotec | Cat. # 130-042-303 |
| MS Columns | Miltenyi Biotec | Cat. # 130-042-201 |

-continued

| | | |
|---|---|---|
| Dead Cell Removal Kit | Miltenyi Biotec | Cat. # 130-090-101 |
| B Cell Isolation Kit II (human) | Miltenyi Biotec | Cat. # 130-091-151 |

PBMCs from an HCV infected individual were thawed at room temperature. Dead cells were removed using the Dead Cell Removal kit (#130-090-101 Miltenyi Biotec). Per $10^7$ total cells, dilute 0.25 ml of 20× Binding Buffer Stock Solution with 4.75 ml of sterile water. 100 ul of Dead Cell Removal Microbeads was added per $10^7$ total cells, mixed and incubated for 15 mins at room temperature. Dead cells were removed on a MACS Separator. Cells were resuspended in MACS Buffer (PBS, 0.5% BSA, 2 mM EDTA): 50 mls of cold PBS+0.25 g of BSA and 0.2 ml of 0.5M EDTA. 40 ul of MACS buffer per $10^7$ total cells and 10 ul of Biotin-Antibody Cocktail was added per $10^7$ total cells, and incubated for 10 mins in the refrigerator. Add 30 ul of MACS buffer per $10^7$ total cells. Add 20 ul of Anti-Biotin Microbeads for 20 mins in the refrigerator. Resuspend to 500 ul of MACS Buffer and remove non-B cell population on an MS column on a MACS Separator. Cells were staining cells for FACS Aria Sort as follows:

| | | |
|---|---|---|
| CD19 Pe-Cy7 Mouse Anti-Human (SJ25C1) | BD Pharmingen | Cat. # 557835 |
| Purified CD81 Mouse Anti-Human (JS-81) | BD Pharmingen | Cat. # 555675 |
| CD81 APC Mouse Anti-Human (JS-81) | BD Pharmingen | Cat. #551112 |
| Delta 3 E2-HIS Protein 0.59 mg/ml | Drummer Lab | |
| Penta-HIS Alexa Fluor 488 | Qiagen | Cat. # 35310 |
| Alexa Fluor 488 Goat Anti-Mouse IgG | Life Tech | Cat. # A11001 |

FACS Buffer (PBS, 2% FCS, 1 mM EDTA): 50 mls cold PBS + 1 ml FCS + 0.1 ml 0.5M EDTA Cells were labelled with 100 ul of CD19 PE-Cy7 antibody (1:50) in FACS Buffer. Mix well and incubate for 30 mins in refrigerator. After two washes in FACS buffer, the resuspend cell pellet was stained with in 100 ul of purified CD81 antibody (1:50) in FACS Buffer for 30 mins at 4° C. After two washes, the resuspend cell pellet was incubated with 20 μg of Delta3 protein in 100 ul of FACS Buffer for 30 mins at 4° C. Cells were washed twice with 500 ul of FACS buffer at 300 g for 5 mins. The resuspended cell pellet was stained with 100 ul of CD81 APC antibody (1:50) and Penta-HIS 488 (1:100) in FACS Buffer for 30 mins at 4° C. After washing cells twice with 500 ul of FACS buffer at 300 g for 5 mins, cells were resuspended with 200 ul of FACS buffer and proceed onto FACS Sort immediately.

| RPMI-1640 media supplemented with 10% FCS, 1% NEAA, 2 mM L-Glutamine, 0.1 mg/ml Gentamicin, 1 ug/ml minocycline. | | |
|---|---|---|
| R848 (1 mg/ml) | Invivogen | Cat. # tlrl-r848 |
| IL-2 human | GenScript | Cat. # Z00368 |

The results (FIG. 23) show that the assembled Δ123 that contains multiple copies of the C-terminal his tag can efficiently detect E2-reactive B cells. Approximately 0.5% of the B cell population were E2 specific. This demonstrates the use of assembled proteins to act as multivalent proteins for immune marker detection.

Example 26: Size of Assembled Proteins

SEC-MALS analysis was used to determine the molar mass of assembled Δ123A7 and assembled Δ123 proteins.

Prior to sample loading a Wyatt WTC-030-N5 4.6/300 column was equilibrated with MT-PBS. The flow rate was 0.2 ml/min. A DAWN Heleos MALS detector was used in series with an Agilent 1200 series UV diode array detector and an Optilab T-rEx RI detector. The MALS detector was normalised using BSA.

The assembled Δ123A7 sample is polydispersed, containing MW species over the range of 262 to 675 kDa. The weight average molar mass is 409 kDa. The assembled Δ123 sample is polydispersed, containing MW species over the range of 210 to 744 kDa. The weight average molar mass is 408.7 kDa. The range of E2 protomers in the assembled Δ123A7 sample was 5-15 and in Δ123 was 4-16 with an average of 9 in each case.

Example 27: Assembly of Proteins

To examine the range of assembly that can be achieved using reducing agent DTT, multiple independent assembly experiments were performed. The results show that the monomeric 4123A7 can be refolded at an efficiency of up to 80% while up to 71% of Δ123 can be assembled into HMW forms.

It was assessed whether the residual monomeric species could be treated with DTT and assembled into HMW forms. A 1 mg/ml solution of monomeric Δ123A7, that was not assembled into HMW forms from a previous experiment, was treated with a final concentration of 0.6 mM DTT at 37° C. for 30 min. A further 3 ul of 100 mM DTT was added to the protein preparation, mixed and incubated for another 30 minutes at 37° C. 250 ul of 1xPBS pH6.8 was then added and incubated at room temperature for 15 minutes and repeated two more times. The proteins were then buffer exchanged and concentrated using a 4 ml Amicon ultracentrifugal device (30K MWCO), and washed 2× with 1xPBS pH6.8 until a volume of 500 ul was achieved and transferred to an eppendorf tube. The treated protein was analysed using gel filtration chromatography. The results showed that 30% of the residual monomeric Δ123A7 could be assembled into HMW forms (FIG. 25). This suggests there is no limit to the ability to assemble monomeric HCV E2 proteins into HMW forms using this method and in practice up to 100% of the monomeric form can be converted to assembled HMW forms.

Example 28: Assembly of Other Proteins

It was examined whether other forms of HCV E2 could be assembled into HMW species using the same method. Monomeric H77c E2 comprising residues 384-661 was treated with DTT as described in example 25 and assembled into HMW forms. Gel filtration chromatography revealed that approximately 40% had assembled into HMW forms (FIG. 26). The same process was performed using the RBDA7 protein wherein the Monomeric H77c E2 comprising residues 384-661 containing Cys-Ala mutations at C581, C585, C652, C677, C494, C486, C459, C452, C564, C597, and C569 (A7) was treated in the same way. In this example approximately 10% was assembled into HMW forms (FIG. 27).

To investigate whether the method is broadly applicable to assembling higher order species from other proteins, largely monomeric HIV envelope protein truncated to remove the C-terminal transmembrane domain and cytoplasmic tail from the AD8 sequence using the above method (Env) were used. Following treatment with DTT and assembly, a small shift in the gel filtration profile was observed corresponding to the formation of HMW species of env (FIG. 28). The formation of higher order oligomers, in particular trimers, is desirable for HIV as these have been shown to retain binding of broadly neutralizing antibodies and are favoured vaccine candidates for the production of broadly neutralizing antibodies (de Taeye et al., 2015). This data suggests that the method can be applied to other proteins where formation of higher-order oligomers from monomers or lower order species is desired for antigen production.

Many modifications will be apparent to those skilled in the art without departing from the scope of the present invention.

TABLE 1

| Transfection volume | Total number of cells | Amount of DNA | DNA dilution volume (in Opti-MEM) | Amount of 293fectin | 293fectin dilution volume (in Opti-MEM) |
|---|---|---|---|---|---|
| 150 mL | $1.5 \times 10^8$ | 150 μg | 3 mL | 150 uL | 3 mL |

TABLE 2

| Antibody | Species | NAb activity[1] | Epitope type[2] | Residues[3] | E2-CD81[4] |
|---|---|---|---|---|---|
| Anti-HIS | Rabbit | No | C | C-terminal 6xHIS | No |
| HCV1 | Human | Yes | C | L413, N415, W420 | Yes |
| AR3A | Human | Yes | DC | S424, G523, P525, G530, D535, V538, N540 | No |
| AR3B | Human | Yes | DC | Q412, T416, G418, N423, S424, G523, P525, G530, D535, N540 | Yes |
| AR3C | Human | Yes | DC | S424, H488, G523, P525, G530, D535, V538, N540 | Yes |
| AR3D | Human | Yes | DC | Q412, S424, G523, G530, D535 | Yes |
| CBH-4B | Human | No | DC | R587-R596 | No |
| CBH-4D | Human | No | DC | V536, P612, L615, R587-R596 | No |
| HC-11 | Human | Yes | DC | S424, T425, A426, L427, N428, C429, Y527, W529, D535, V536 | Yes |
| H52 | Murine | No | C | C652 | No |
| H53 | Murine | No | DC | N540, W549 | No |
| 1 | Murine | No | DC | N/D | Yes |
| 7 | Murine | No | DC | N/D | Yes |
| 10 | Murine | Yes | DC | N/D | Yes |
| 12 | Murine | No | DC | N/D | Yes |
| 16 | Murine | No | DC | N/D | Yes |
| 20 | Murine | No | DC | N/D | Yes |
| 24 | Murine | Yes | C | N/D | Yes |
| 60 | Murine | | | N/D | |

[1]Ability of MAbs to induce at least type-specific neutralisation.
[2]Target epitopes are either continuous/conformation-independent (C) or discontinuous/conformation-dependent (DC).
[3]Target amino acid residues. Not determined is abbreviated by N/D.
[4]Ability of MAbs to block E2-CD81 interactions.

TABLE 3

| | Concentration of monomeric H77 Δ123 (μg/μL) | Concentration of DTT (mM) | Incubation time (h) | Temperature (° C.) |
|---|---|---|---|---|
| 1. | 1 | 0.00 | 24.0 | 37 |
| 2. | 10 | 0.10 | 24.0 | 37 |
| 3. | 5 | 1.00 | 24.0 | 37 |
| 4. | 5 | 0.50 | 24.0 | 37 |
| 5. | 5 | 0.10 | 24.0 | 37 |
| 6. | 5 | 0.10 | 2.0 | 37 |
| 7. | 5 | 0.10 | 0.5 | 37 |
| 8. | 1 | 0.10 | 2.0 | 37 |
| 9. | 1 | 1.00 | 0.5 | 37 |
| 10. | 1 | 0.30 | 0.5 | 37 |
| 11. | 1 | 0.10 | 0.5 | 37 |
| 12. | 1 | 0.05 | 0.5 | 37 |

TABLE 4

| | Concentration of monomeric H77c Δ123 (μg/μL) | Concentration of GSH and GSSG, respectively (mM) | Incubation time (h) | Temperature (° C.) |
|---|---|---|---|---|
| 1. | 1 | 0.0, 0.0 | 24 | 37 |
| 2. | 10 | 2.0, 0.4 | 24 | 37 |
| 3. | 5 | 2.0, 0.4 | 24 | 37 |
| 4. | 1 | 2.0, 0.4 | 24 | 37 |
| 5. | 5 | 2.0, 0.4 | 2 | 37 |

TABLE 5

| | Concentration of monomeric H77c Δ123 (μg/μL) | Concentration of TCEP (mM) |
|---|---|---|
| 1. | 1 | 10 |
| 2. | 1 | 50 |
| 3. | 1 | 100 |
| 4. | 1 | 200 |
| 5. | 5 | 50 |
| 6. | 5 | 200 |
| 7. | 1 | 0 |

TABLE 6

| Strain | Round | % Monomers | % Dimers | % HMW2 | % HMW1 | Total % HMW |
|---|---|---|---|---|---|---|
| H77 | N/A | 64.90 | 11.67 | 18.90 | 4.23 | 23.13 |
| Con1 | 1 | 25.46 | 28.52 | 40.62 | 5.40 | 46.02 |
| Con1 | 2 | 14.37 | 38.64 | 44.56 | 2.42 | 46.98 |
| S52 | 1 | 35.29 | 19.05 | 36.74 | 8.14 | 44.88 |
| S52 | 2 | 34.81 | 23.59 | 39.77 | 1.79 | 41.56 |

TABLE 7

| Antibody | NAb activity[1] | Epitope type[2] | Binding relative to monomeric Δ123 of corresponding strain[3] | | | Binding relative to H77c HMW1 Δ123[4] | |
|---|---|---|---|---|---|---|---|
| | | | H77c | Con1 | S52 | Con1 | S52 |
| HCV1 | Yes | C | 1.21 | 1.46 | 0.92 | 2.05 | 2.08 |
| AR3B | Yes | DC | <0.37 | 0.17 | <0.09 | <6.58 | <1.68 |
| AR3C | Yes | DC | 0.18 | 0.13 | 0.54 | 3.92 | 6.17 |
| AR3D | Yes | DC | <0.17 | 0.08 | — | 4.73 | N/A |
| CBH-4B | No | DC | <0.27 | <0.24 | <0.62 | <1.00 | <1.00 |
| CBH-4D | No | DC | <0.27 | <0.11 | <0.07 | <1.23 | <1.68 |
| HC-11 | Yes | DC | 0.21 | 0.28 | <0.20 | 6.97 | 1.00 |
| H52 | No | C | <9.53 | <11.19 | <6.14 | 1.47 | 0.56 |
| 10 | Yes | DC | <0.07 | <0.07 | <0.25 | <0.45 | <0.45 |
| 24 | Yes | C | 3.03 | 0.82 | 0.52 | 0.67 | 0.28 |
| 60 | | | <0.47 | <0.57 | — | <1.00 | N/A |

[1]Ability of MAbs to induce at least type-specific neutralisation.
[2]Target epitopes are either continuous/conformation-independent (C) or discontinuous/conformation-dependent (DC).
[3]Binding of MAbs to HMW1 Δ123 relative to monomeric Δ123. Refer to FIG. 6A for original ELISA results. Blue represents results from single dilution point assessments (FIG. 6B) and discontinued testing on ELISA, where + indicates positive reactivity and − indicates negligible reactivity.
[4]Binding of MAbs to Con1 and S52 HMW1 Δ123 relative to H77c HMW1 Δ123.
Not applicable is abbreviated N/A.

TABLE 8

| | Concentration of monomeric H77c Δ123 (μg/μL) | Concentration of TCEP (mM) | Concentration of BMOE (mM) |
|---|---|---|---|
| 1. | 1 | 10 | 0.2 |
| 2. | 1 | 50 | 0.2 |
| 3. | 1 | 100 | 0.2 |
| 4. | 1 | 200 | 0.2 |
| 5. | 5 | 50 | 0.2 |
| 6. | 5 | 200 | 0.2 |
| 7. | 1 | 0 | 0.2 |

TABLE 9

| | Concentration of monomeric H77c Δ123 (μg/μL) | Concentration of GSH and GSSG, respectively (mM) | Incubation time (h) | Temperature (° C.) | Ratio of monomers vs. dimers |
|---|---|---|---|---|---|
| 1. | 1 | 0.0, 0.0 | 24 | 37 | 4.65 |
| 2. | 10 | 2.0, 0.4 | 24 | 37 | 2.51 |
| 3. | 5 | 2.0, 0.4 | 24 | 37 | 2.99 |
| 4. | 1 | 2.0, 0.4 | 24 | 37 | 6.89 |
| 5. | 5 | 2.0, 0.4 | 2 | 37 | 3.36 |

TABLE 10

| H77c Δ123 | % of monomers | % of multimers | Ratio of monomers vs. multimers |
|---|---|---|---|
| Untreated | 87.52 | 2.59 | 33.82 |
| GSH/GSSG | 52.68 | 43.13 | 1.22 |

TABLE 11

| | Concentration of monomeric H77c Δ123 (μg/μL) | Concentration of DTT (mM) | Incubation time (h) | Temperature (° C.) | Ratio of monomers vs. dimers |
|---|---|---|---|---|---|
| 1. | 1 | 0.00 | 24.0 | 37 | 3.41 |
| 2. | 10 | 0.10 | 24.0 | 37 | 3.02 |
| 3. | 5 | 1.00 | 24.0 | 37 | 2.35 |
| 4. | 5 | 0.50 | 24.0 | 37 | 2.32 |
| 5. | 5 | 0.10 | 24.0 | 37 | 2.55 |
| 6. | 5 | 0.10 | 2.0 | 37 | 2.66 |
| 7. | 5 | 0.10 | 0.5 | 37 | 1.91 |
| 8. | 1 | 0.10 | 2.0 | 37 | 2.16 |
| 9. | 1 | 1.00 | 0.5 | 37 | 1.51 |
| 10. | 1 | 0.30 | 0.5 | 37 | 1.45 |
| 11. | 1 | 0.10 | 0.5 | 37 | 1.33 |
| 12. | 1 | 0.05 | 0.5 | 37 | 1.95 |

TABLE 12

| H77c Δ123 | % of monomers | % of multimers | Ratio of monomers vs. multimers |
|---|---|---|---|
| Untreated | 87.52 | 2.59 | 33.82 |
| DTT | 69.51 | 28.84 | 2.41 |

TABLE 13

| Reducing agent | Refolding method | Antigen | Analytical method (SDS-PAGE and/or Gel Filtration) | Generation of refolded proteins (Yes/No) |
|---|---|---|---|---|
| 0-500 mM TCEP | 0.2 mM BMOE crosslinker | Δ123 | SDS-PAGE | No |
| 2.00 mM GSH | redox-shuffling system w. 0.4 mM GSSG | Δ123 | SDS-PAGE and Gel Filtration | Yes |
| 0-1.00 mM DTT | slow dilution | Δ123 | SDS-PAGE and Gel Filtration | Yes |

TABLE 14

| Reducing agent | Antigen | Elution time (min) | % refolded | Antigenicity characterisation available (Yes/No) |
|---|---|---|---|---|
| 2.0 mM GSH | Δ123 | 69.00 | 43.13 | No |
| 1 hit of 0.3 mM DTT | Δ123 | 59.44 | 50.15 | No |
| 2 hits of 0.3 mM DTT | Δ123 | 54.48 | 62.81 | Yes |
| | Δ123 (repeat 1) | 53.93 | 50.13 | No |
| | D123 w. protease inhibitors | 54.55 | 52.67 | No |
| | RBD | 57.77 | 39.75 | No |
| | ALA7 Δ123 | 52.97 | 47.41 | Yes |
| | ALA7 RBD | 59.46 | 10.38 | No |
| 3 hits of 0.3 mM DTT | Δ123 | 53.95 | 54.47 | No |

TABLE 15

| Group name | Antigen# | Number of animals |
|---|---|---|
| 1-F | Native Δ123 HMW | 8 |
| 2-F | Assembled Δ123 | 8 |
| 3-F | Assembled Δ123A7 | 8 |
| 4-F* | Monomeric Δ123 | 4 |
| 5-F* | Monomeric Δ123A7 | 4 |
| 6-F | No antigen | 6 |

100 μg antigen administered with equal volume of Addavax, 4 times three weeks apart. Final bleed two weeks after last immunization.
*For analysis of data, results from groups 4 and 5 were combined to create evenly sized groups of animals.

TABLE 16

| | 1-F | 2-F | 3-F | 4-F + 5-F |
|---|---|---|---|---|
| Geometric mean | 30162 | 41866 | 28686 | 21756 |
| Mean | 34701 | 44460 | 32444 | 24898 |

TABLE 17

| | 1-F | 2-F | 3-F | 4-F + 5-F |
|---|---|---|---|---|
| Geometric mean | 3756 | 2176 | 1339 | 232 |
| Mean | 4588 | 5289 | 1763 | 344.4 |

TABLE 18

| | 1-F | 2-F | 3-F | 4-F + 5-F |
|---|---|---|---|---|
| Geometric mean | 3051 | 4627 | 1888 | 1191 |
| Mean | 3638 | 5413 | 2150 | 3599 |
| Minimum | 600 | 1800 | 900 | 90 |
| 25% Percentile | 2125 | 3250 | 1200 | 400 |
| Median | 4500 | 4250 | 1950 | 1000 |
| 75% Percentile | 5000 | 8000 | 2400 | 4375 |
| Maximum | 5000 | 12000 | 5000 | 18000 |

TABLE 19

| | 1-F | 2-F | 3-F | 4-F + 5-F |
|---|---|---|---|---|
| Geometric mean | 483.3 | 439.8 | 100.4 | 26.24 |
| Mean | 587.5 | 1100 | 162.5 | 52.5 |

TABLE 20

|  | 1-F | 2-F | 3-F | 4-F + 5-F |
|---|---|---|---|---|
| Geometric mean | 308.3 | 246.4 | 188.1 | 238.2 |
| Mean | 326.3 | 261.3 | 215 | 307.5 |

TABLE 21

|  | 1-F | 2-F | 3-F | 4-F + 5-F |
|---|---|---|---|---|
| Geometric mean | 39.92 | 51.36 | 41.33 | 39.94 |
| Mean | 41.25 | 58.75 | 45 | 46.25 |

TABLE 22

|  | 1-F | 2-F | 3-F | 4-F + 5-F |
|---|---|---|---|---|
| Geometric mean | 692.1 | 266.6 | 342.6 | 278.6 |
| Mean | 773.1 | 361.7 | 484.6 | 430.6 |
| Minimum | 220.3 | 43.31 | 102.1 | 20 |
| Maximum | 1231 | 627.5 | 1521 | 1122 |

TABLE 23

|  | 1-F | 2-F | 3-F | 4-F |
|---|---|---|---|---|
| Geometric mean | 118 | 104 | 79 | 45 |
| Mean | 121 | 106 | 81 | 47 |
| Minimum | 55 | 54 | 47 | 21 |
| Maximum | 195 | 191 | 129 | 155 |

TABLE 24

|  | 1-F | 2-F | 3-F | 4-F + 5-F |
|---|---|---|---|---|
| Geometric mean | 18 | 20 | 12 | 14 |
| Mean | 19 | 20 | 12 | 14 |
| Minimum | 10 | 16 | 10 | 10 |
| Maximum | 35 | 27 | 17 | 39 |

TABLE 25

|  | 1-F | 2-F | 3-F | 4-F + 5-F |
|---|---|---|---|---|
| Geometric mean | 46 | 50 | 38 | 33 |
| Mean | 48 | 51 | 39 | 35 |
| Minimum | 17 | 26 | 28 | 14 |
| Maximum | 87 | 102 | 56 | 110 |

TABLE 26

|  | 1-F | 2-F | 3-F | 4-F + 5-F |
|---|---|---|---|---|
| Geometric mean | 119 | 207 | 222 | 353 |
| Mean | 124 | 213 | 228 | 362 |
| Minimum | 46 | 71 | 105 | 191 |
| Maximum | 303 | 432 | 814 | 756 |

TABLE 27

|  | Retention time (min) | Molar Mass Range kDa | Units of E2 Range | Molar Mass kDa Mw | Av Units of E2 |
|---|---|---|---|---|---|
| Δ123A7 | 12-14.5 | 674.8-262.2 | 5-15 | 408.7 | 9 |
| Δ123 | 12.5-15.5 | 744-210 | 4-16 | 408.7 | 9 |

REFERENCES

Alhammad et al (2015) J Virol. 2015; 89 (24): 12245-61. doi: 10.1128/JVI. 02070-15. PubMed PMID: 26378182; PubMed Central PMCID: PMC4665232.
Altman et al (1996) Science 274 (5284): 94-96.
Broering et al (2009) J Virol. 2009; 83 (23): 12473-82. Epub 2009 Sep. 18. doi: 10.1128/JVI.01138-09 JVI.01138-09 [pii]. PubMed PMID: 19759151; PubMed Central PMCID: PMC2786766.
Connor et al (1995) Virology. 206 (2): 935-44. doi: 10.1006/viro.1995.1016. PubMed PMID: 7531918.
de Taeye et al (2015) Cell; 163 (7): 1702-15. doi: 10.1016/j.cell.2015.11.056. PubMed PMID: 26687358; PubMed Central PMCID: PMC4732737.
Dolton et al (2015) Immunolog.y 146 (1): 11-22/
Drummer et al (2003) FEBS Lett. 546 (2-3): 385-90. PubMed PMID: 12832074.
Flint et al (1999) J Virol. 73 (8): 6235-44. PubMed PMID: 10400713; PubMed Central PMCID: PMCPMC112700.
He et al (1995) J Virol. 69 (7): 4587-92. PubMed PMID: 7769729.
Keck et al (2012) PLoS Pathog. 8 (4): e1002653. Epub 2012 Apr. 19. doi: 10.1371/journal.ppat. 1002653 PPATHOGENS-D-11-02162 [pii]. PubMed PMID: 22511875; PubMed Central PMCID: PMC3325216.
Khan et al (2014) Nature. 2014. doi: 10.1038/nature13117. PubMed PMID: 2455313.
Krey et al (2013) 9 (5): e1003364. doi: 10.1371/journal.ppat.1003364. PubMed PMID: 23696737; PubMed Central PMCID: PMC3656090.
Keck et al (2013) J Virol. 2013; 87 (1): 37-51. Epub 2012 Oct. 26. doi: 10.1128/JVI.01941-12 JVI.01941-12 [pii]. PubMed PMID: 23097455; PubMed Central PMCID: PMC3536422.
Law et al (2008) Nat Med. 2008; 14 (1): 25-7. Epub 2007 Dec. 8. doi: nm1698 [pii] 10.1038/nm1698. PubMed PMID: 18064037.
McCaffrey et al (2007) J Virol 81:9584-9590.
Morin et al (2012) PLoS Pathog. 8 (8): e1002895. Epub 2012 Sep. 7. doi: 10.1371/journal.ppat. 1002895PPATHOGENS-D-12-01073 [pii]. PubMed PMID: 22952447; PubMed Central PMCID: PMC3431327.
Owsianka et al (2001) J Gen Virol.82 (Pt 8): 1877-83. Epub 2001 Jul. 18. PubMed PMID: 11457993.
Owsianka et al (2005) J Virol. 79 (17): 11095-104. PubMed PMID: 16103160.
Pantua et al (2013) J Mol Biol. 2013; 425 (11): 1899-914. Epub 2013 Mar. 6. doi: 10.1016/j.jmb.2013.02.025 S0022-2836 (13) 00127-7 [pii]. PubMed PMID: 23458406.
Petrovsky et al (2004) Immunol Cell Biol.Oct; 82 (5): 488-96.
Sabo et al (2011) J Virol. 2011; 85 (14): 7005-19. Epub 2011 May 6. doi: 10.1128/JVI.00586-11 JVI.00586-11 [pii]. PubMed PMID: 21543495; PubMed Central PMCID: PMC3126585.

Tarr et al (2006) Hepatology. 43 (3): 592-601. Epub 2006 Feb. 24. doi: 10.1002/hep.21088. PubMed PMID: 16496330.

Vietheer et al (2017) Hepatology. 2017; 65 (4): 1117-31. doi: 10.1002/hep.28989. PubMed PMID: 27997681; PubMed Central PMCID: PMCPMC5408392.

Vollers et al (2008) Immunology. 123 (3): 305-313.

Wilson-Welder et al (2009) J Pharm Sci. Apr; 98 (4): 1278-316. doi: 10.1002/jps.21523.

Zhang et al (2009) Proc Natl Acad Sci USA. 106 (18): 7537-41. Epub 2009 Apr. 22. doi: 0902749106 [pii] 10.1073/pnas.0902749106. PubMed PMID: 19380744; PubMed Central PMCID: PMC2670884.

The invention claimed is:

1. A method of preparing extracellularly assembled higher order antigen from a native lower order antigen, the method comprising the following steps:
   (i) enriching a solution for a lower order antigen comprising hepatitis C virus envelope glycoprotein 2 (HCV E2) comprising one or more native cysteines relative to the amount of higher order antigen in the solution, wherein said enriching is prior to and does not comprise contacting the solution with a reducing which converts higher order antigen to lower order antigen;
   (ii) contacting the lower order antigen of step (i) with a solution comprising a thiol-containing reducing agent for a time and under conditions sufficient to reduce one or more of the one or more native cysteines of the lower order antigen; and
   (iii) removing or diluting the reducing agent or contacting the reduced lower order antigen with an oxidising agent, thereby resulting in assembly of the lower order antigen from (ii) into an assembled higher order antigen;
   wherein the higher order antigen is a trimer or above and the lower order antigen is a monomer or a dimer.

2. The method of claim 1 wherein steps (ii) and (iii) are repeated with a solution comprising residual lower order antigen from step (iii) in order to improve the efficiency of the method of assembly of lower order antigen into higher order antigen.

3. The method of claim 1 wherein at least 80% of the lower order antigen is converted into higher order antigen.

4. The method of claim 1 wherein the assembled higher order antigen lacks one or more of hypervariable region 1 (HVR1) or a part thereof, the hypervariable region 2 (HVR2) or a part thereof and/or the intergenotypic variable region (igVR/VR3) or a part thereof.

5. The method of claim 1 wherein the assembled higher order antigen comprises a non-cysteine substitution or mutation in one or more of amino acid residues selected from the group comprising: C581, C585, C652, C677, C494, C486, C459, C452, C564, C597, and C569.

6. A method of producing a vaccine composition comprising the method of claim 1 and wherein the assembled higher order antigen is admixed with a pharmaceutically or physiologically acceptable diluent, carrier or adjuvant.

7. The method of claim 1 wherein step (ii) is repeated prior to step (iii) in order to improve the efficiency of the method of assembly of lower order antigen into higher order antigen.

8. The method of claim 5, wherein the modified HCV E2 comprises a deletion of part or all of HVR1, HVR2 and/or igVR/VR3.

* * * * *